US009524417B2

(12) United States Patent
Behrend et al.

(10) Patent No.: US 9,524,417 B2
(45) Date of Patent: *Dec. 20, 2016

(54) SYSTEMS, DEVICES, AND METHODS FOR DETECTION OF MALARIA

(71) Applicant: Tokitae LLC, Bellevue, WA (US)

(72) Inventors: Matthew R. Behrend, Bellevue, WA (US); Michael C. Hegg, Seattle, WA (US); Matthew P. Horning, Redmond, WA (US); Benjamin K. Wilson, Kirkland, WA (US)

(73) Assignee: Tokitae LLC, Bellevue, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/307,724

(22) Filed: Jun. 18, 2014

(65) Prior Publication Data

US 2014/0294280 A1 Oct. 2, 2014

Related U.S. Application Data

(63) Continuation of application No. 12/925,650, filed on Oct. 25, 2010, now Pat. No. 8,781,184, which is a
(Continued)

(51) Int. Cl.
*G06K 9/00* (2006.01)
*A61B 3/12* (2006.01)
(Continued)

(52) U.S. Cl.
CPC ......... *G06K 9/00147* (2013.01); *A61B 3/1233* (2013.01); *A61B 5/0059* (2013.01); *A61B 5/0062* (2013.01); *A61B 5/14546* (2013.01); *G01N 21/49* (2013.01); *G06K 9/6212* (2013.01); *G06T 7/0014* (2013.01); *A61B 5/05* (2013.01);
(Continued)

(58) Field of Classification Search
CPC ............... A61B 2562/0238; A61B 3/1233; A61B 5/0059; A61B 5/0062; A61B 5/05; A61B 5/14546; A61B 8/06; G01N 21/49; G01N 2333/445; G06K 9/00147; G06K 9/6212; G06T 2207/20076; G06T 2207/30024; G06T 7/0014
See application file for complete search history.

(56) References Cited

U.S. PATENT DOCUMENTS 4,291,938 A 9/1981 Wagner
4,476,519 A 10/1984 Hayamizu
(Continued)

FOREIGN PATENT DOCUMENTS

WO 2008056171 5/2008
WO WO 2008/105695 A1 9/2008
(Continued)

OTHER PUBLICATIONS

Cai et al.; "Applications of gold nanoparticles in cancer nanotechnology"; Nanotechnology, Science and Applications 2008:I; 2008; pp. 17-32; Dove Medical Press Ltd.
(Continued)

*Primary Examiner* — Tom Y Lu
(74) *Attorney, Agent, or Firm* — Daniel J. Honz; Advent, LLP

(57) ABSTRACT

Systems, devices, and methods are described for providing a monitor or treatment device configured to, for example, detect hemozoin, as well as to monitor or treat a malarial infection.

28 Claims, 44 Drawing Sheets

Related U.S. Application Data continuation-in-part of application No. 12/658,619, filed on Feb. 10, 2010, now Pat. No. 8,467,842, which is a continuation-in-part of application No. 12/658,580, filed on Feb. 10, 2010, now Pat. No. 8,504,129, which is a continuation-in-part of application No. 12/658,617, filed on Feb. 10, 2010, now Pat. No. 8,840,536, which is a continuation-in-part of application No. 12/658,638, filed on Feb. 10, 2010, now Pat. No. 8,585,567, which is a continuation-in-part of application No. 12/658,589, filed on Feb. 10, 2010, now Pat. No. 8,388,509, which is a continuation-in-part of application No. 12/658,607, filed on Feb. 10, 2010, now abandoned.

(51) Int. Cl.
| | |
|---|---|
| A61B 5/00 | (2006.01) |
| A61B 5/145 | (2006.01) |
| G01N 21/49 | (2006.01) |
| G06K 9/62 | (2006.01) |
| G06T 7/00 | (2006.01) |
| A61B 5/05 | (2006.01) |
| A61B 8/06 | (2006.01) |

(52) U.S. Cl.
CPC .......... *A61B 8/06* (2013.01); *A61B 2562/0238* (2013.01); *G01N 2333/445* (2013.01); *G06T 2207/20076* (2013.01); *G06T 2207/30024* (2013.01)

(56) References Cited

U.S. PATENT DOCUMENTS

| | | | |
|---|---|---|---|
| 4,585,315 A | 4/1986 | Sincerbox et al. | |
| 5,099,756 A | 3/1992 | Franconi et al. | |
| 5,123,898 A | 6/1992 | Liboff et al. | |
| 5,170,202 A | 12/1992 | Bell | |
| 5,224,922 A | 7/1993 | Kurtz | |
| 5,570,228 A | 10/1996 | Greenberg | |
| 5,580,163 A | 12/1996 | Johnson, II | |
| 5,690,109 A | 11/1997 | Govind et al. | |
| 5,734,498 A | 3/1998 | Krasieva et al. | |
| 6,246,896 B1 | 6/2001 | Dumoulin et al. | |
| 6,272,235 B1 | 8/2001 | Bacus et al. | |
| 6,614,596 B2 | 9/2003 | Gladnick | |
| 6,621,568 B1 | 9/2003 | Yonezawa | |
| 6,675,047 B1 | 1/2004 | Konoplev | |
| 6,721,583 B1 | 4/2004 | Durkin et al. | |
| 6,739,342 B1 | 5/2004 | Fredriksson et al. | |
| 6,822,790 B2 | 11/2004 | Knoblich | |
| 6,922,279 B2 | 7/2005 | Sun et al. | |
| 6,961,599 B2 | 11/2005 | Lambert et al. | |
| 7,142,294 B2 | 11/2006 | Shibata et al. | |
| 7,326,170 B1 | 2/2008 | Miller | |
| 7,338,766 B2* | 3/2008 | Chakrabarty | C07K 14/195 424/185.1 |
| 7,344,279 B2 | 3/2008 | Mueller et al. | |
| 7,351,194 B2 | 4/2008 | Gleich | |
| 7,362,449 B2 | 4/2008 | Dubois et al. | |
| 7,388,668 B2 | 6/2008 | Potma et al. | |
| 7,461,961 B2 | 12/2008 | Li | |
| 7,510,290 B2 | 3/2009 | Pohlert et al. | |
| 7,731,648 B2 | 6/2010 | Ivkov | |
| 7,831,106 B2 | 11/2010 | Elsner et al. | |
| 7,884,998 B2 | 2/2011 | Armstrong | |
| 8,073,551 B2 | 12/2011 | McCann et al. | |
| 8,170,643 B2 | 5/2012 | Turner et al. | |
| 8,221,970 B2* | 7/2012 | Chau | C12Q 1/6886 435/5 |
| 8,311,641 B2 | 11/2012 | Zhu et al. | |
| 8,331,020 B2 | 12/2012 | Soppelsa et al. | |
| 8,388,509 B2 | 3/2013 | Hegg et al. | |
| 8,705,017 B2* | 4/2014 | Hyde | A01M 1/026 356/28 |
| 8,774,884 B2 | 7/2014 | Behrend et al. | |
| 8,781,184 B2* | 7/2014 | Behrend et al. | 382/128 |
| 2001/0034478 A1 | 10/2001 | Lambert et al. | |
| 2002/0155630 A1 | 10/2002 | Iwabuchi | |
| 2003/0030902 A1 | 2/2003 | Fukushima et al. | |
| 2003/0032995 A1 | 2/2003 | Handy et al. | |
| 2003/0194589 A1 | 10/2003 | Pratt et al. | |
| 2003/0215867 A1 | 11/2003 | Gulati | |
| 2004/0135998 A1 | 7/2004 | Chin | |
| 2004/0228515 A1 | 11/2004 | Okabe et al. | |
| 2005/0043636 A1 | 2/2005 | Gaeta et al. | |
| 2005/0059852 A1 | 3/2005 | Rioux et al. | |
| 2005/0087601 A1 | 4/2005 | Gerst, III et al. | |
| 2005/0280808 A1 | 12/2005 | Backhauss et al. | |
| 2005/0288564 A1 | 12/2005 | Iuliano | |
| 2006/0012778 A1 | 1/2006 | Vaughnn | |
| 2006/0036301 A1 | 2/2006 | Eggers et al. | |
| 2006/0169314 A1 | 8/2006 | Horio et al. | |
| 2007/0115461 A1 | 5/2007 | Fairley et al. | |
| 2007/0128642 A1* | 6/2007 | Vodyanoy | G01N 33/5002 435/6.18 |
| 2007/0179576 A1 | 8/2007 | Nagano et al. | |
| 2007/0236785 A1 | 10/2007 | Matsumoto | |
| 2007/0253227 A1 | 11/2007 | James et al. | |
| 2008/0100834 A1 | 5/2008 | Kung et al. | |
| 2008/0133766 A1 | 6/2008 | Luo | |
| 2008/0181221 A1 | 7/2008 | Kampmann et al. | |
| 2008/0228063 A1 | 9/2008 | Turner et al. | |
| 2008/0249350 A1 | 10/2008 | Marchitto et al. | |
| 2008/0297783 A1 | 12/2008 | Urano et al. | |
| 2009/0041808 A1 | 2/2009 | Akira et al. | |
| 2009/0093713 A1 | 4/2009 | Hyde et al. | |
| 2009/0109285 A1 | 4/2009 | Tobiason et al. | |
| 2009/0116551 A1 | 5/2009 | Nilsson et al. | |
| 2009/0149726 A1 | 6/2009 | Hyde et al. | |
| 2009/0192383 A1 | 7/2009 | Pananakis et al. | |
| 2009/0227044 A1 | 9/2009 | Dosev et al. | |
| 2009/0312637 A1 | 12/2009 | Raju et al. | |
| 2009/0318784 A1 | 12/2009 | Newman et al. | |
| 2010/0120132 A1 | 5/2010 | Koo | |
| 2010/0145420 A1 | 6/2010 | Zhu et al. | |
| 2010/0179625 A1 | 7/2010 | Kao et al. | |
| 2010/0196920 A1 | 8/2010 | Lee et al. | |
| 2010/0197993 A1 | 8/2010 | Vasishta | |
| 2010/0222662 A1 | 9/2010 | Hegg et al. | |
| 2010/0222774 A1 | 9/2010 | Hegg et al. | |
| 2010/0256467 A1 | 10/2010 | Hegg et al. | |
| 2011/0077451 A1 | 3/2011 | Marchitto et al. | |
| 2011/0130618 A1 | 6/2011 | Edoute et al. | |
| 2011/0196222 A1 | 8/2011 | Behrend et al. | |
| 2011/0204257 A1 | 8/2011 | Wiseman et al. | |
| 2012/0157749 A1 | 6/2012 | Lee et al. | |
| 2012/0190911 A1 | 7/2012 | McKenna et al. | |
| 2012/0190912 A1 | 7/2012 | McKenna et al. | |
| 2012/0238945 A1 | 9/2012 | Hyde et al. | |
| 2012/0238948 A1 | 9/2012 | Hyde et al. | |
| 2012/0259154 A1 | 10/2012 | Hong et al. | |
| 2013/0053619 A1 | 2/2013 | McKenna et al. | |
| 2013/0053620 A1 | 2/2013 | Susedik et al. | |
| 2013/0123885 A1 | 5/2013 | Zhu et al. | |
| 2013/0158634 A1 | 6/2013 | Edoute et al. | |

FOREIGN PATENT DOCUMENTS

| | | |
|---|---|---|
| WO | 2009009899 | 1/2009 |
| WO | 2012012800 | 1/2012 |

OTHER PUBLICATIONS

PCT International Search Report; International Application # PCT/US11/00259; Published Aug. 18, 2011; pp. 1-5.
PCT International Search Report; International Application # PCT/US11/00260; Published Aug. 18, 2011; pp. 1-5.
PCT International Search Report; International Application # PCT/US11/01815; Published May 10, 2012; pp. 1-2.

(56) References Cited

OTHER PUBLICATIONS

Andressen et al.; "Infrared Multiphoton Microscopy; Subcellular-Resolved Deep Tissue Imaging"; Science Direct, Current Opinion in Biotechnology; bearing a date of 2009; pp. 1-9; vol. No. 20; Elsevier Ltd.; could be located at: www.sciencedirect.com.

Arambage et al.; "Research: Malaria Ookinetes Exhibit Multiple Markers for Apoptosis-Like Programmed Cell Death in vitro"; BioMed Central, Parasites & Vectors; bearing a date of 2009; pp. 1-16; vol. 2, No. 32; BioMed Central Ltd.; located at http://www.parasitesandvectors.com/content/2/1/32.

Bahadur et al.; "Biomaterials and Magnetism"; Sadhana; bearing dates of Jun./Aug. 2003; pp. 639-656; vol. 28, Parts 3 & 4; Printed in India.

Balasubramanian et al.; "Photoacoustic Spectroscopy and its Use in Biology"; Bioscience Reports; bearing a date of 1993; pp. 981-995; vol. 3; The Biochemical Society.

Barcinski et al.; "Apoptosis in Parasites and Parasite-Induced Apoptosis in the Host Immune System: A New Approach to Parasite Diseases"; Brazilian Journal of Medical and Biological Research; bearing a date of 1999; pp. 395-401; vol. 32, No. 4.

Belisle et al.; "Sensitive Detection of Malaria Infection by Third Harmonic Generation Imaging"; Biophysical Journal: Biophysical Letters; bearing a date of 2008; pp. L26-L28; The Biophysical Society.

Biagini et al.; "The Digestive Food Vacuole of the Malaria Parasite is a Dynamic Intracellular Ca2+ Store"; The Journal of Biological Chemistry; bearing a date of Jul. 25, 2003; pp. 27910-27915; vol. 278, No. 30; The American Society for Biochemistry and Molecular Biology, Inc.; could be located at: www.jbc.org.

Chen et al.; "Epi-Third and Second Harmonic Generation Microscopic Imaging of Abnormal Enamel"; Optics Express; bearing a date of Jul. 21, 2008; pp. 11670-11679; vol. 16, No. 15; OSA.

Chu et al.; "Functional THG Microscopy with Plasmon-Resonance Enhancement in Silver Nanoparticles"; CThPDD7; bearing a date of 2003; pp. 1-2; Optical Society of America.

Clay et al.; "Spectroscopy of Third-Harmonic Generation: Evidence for Resonances in Model Compounds and Ligated Hemoglobin"; J. Opt. Soc. Am. B; bearing a date of May 2006; pp. 932-950; vol. 23, No. 5; Optical Society of America.

Clay et al.; "Ultrafast Third Harmonic Micro-Spectroscopy Reveals a Two-Photon Resonance in Human Hemoglobin"; Photonics West; bearing a date of Jan. 22-25, 2006; pp. 1-8; vol. 6108, No. 6108-8.

Cui, et al.; "Cytotoxic Effect of Curcumin on Malaria Parasite *Plasmodium falciparum*: Inhibition of Histone Acetylation and Generation of Reactive Oxygen Species"; Antimicrobial Agents and Chemotherapy; bearing a date of Feb. 2007; pp. 488-494; vol. 51, No. 2; American Society for Microbiology.

De Villiers, et al.; "Oriented Nucleation of B-Hematin Crystals Induced at Various Interfaces: Relevance to Hemozoin Formation"; Crystal Growth & Design; bearing a date of 2009; pp. 626-632; vol. 9, No. 1; American Chemical Society.

Debarre et al.; "Quantitative Characterization of Biological Liquids for Third-Harmonic Generation Microscopy"; Biophysical Journal; bearing a date of Jan. 2007; pp. 603-612; vol. 92; The Biophysical Society.

Debarre et al.; "Signal Epidetection in Third-Harmonic Generation Microscopy of Turbid Media"; Optics Express; bearing a date of Jul. 9, 2007; pp. 8913-8924; vol. 15, No. 14; OSA.

Ding, et al.; "ELF Magnetic Fields Promote H2O2-Induced Apoptosis and Necrosis and Its Molecular Mechanism"; 3rd International EMF Seminar in China; Electromagnetic Fields and Biological Effects; bearing dates of Oct. 13-17, 2003; pp. 114 (plus cover page), Session 8-7.

Egan; "Physico-chemical aspects of hemozoin (malaria pigment) structure and formation"; Journal of Inorganic Biochemistry; bearing a date of 2002; pp. 19-26; vol. 91; Elsevier Science Inc.

Feagin, et al.; "Effects of Alternating Magnetic Fields on Malaria Parasites"; 3rd International EMF Seminar in China; Electromagnetic Fields and Biological Effects; bearing dates of Oct. 13-17, 2003; pp. 116 (plus cover page), Session 9-1.

Galanzha, et al.; "In Vivo, Noninvasive, Label-Free Detection and Eradication of Circulating Metastatic Melanoma Cells Using Two-Color Photoacoustic Flow Cytometry with a Diode Laser"; Cell, Tumor, and Stem Cell Biology; bearing a date of Oct. 15, 2009; pp. 7926-7934; vol. 69, No. 20; American Association for Cancer Research.

Halpern, et al.; "Oxymetry Deep in Tissues with Low-Frequency Electron Paramagnetic Resonance"; PNAS, Physiology; bearing a date of Dec. 20, 1994; pp. 13047-13051; vol. 91, No. 26; JSTOR.

Hothi, et al.; "Kinetic Isotope Effects and Ligand Binding in PQQ-Dependent Methanol Dehydrogenase"; Biochem. J.; bearing a date of 2005; pp. 123-133; vol. 388; Biochemical Society.

Lamikanra, et al.; "Hemozoin (Malaria Pigment) Directly Promotes Apoptosis of Erythroid Precursors"; PLos One, Open Access; bearing a date of Nov. 6, 2009; pp. 1-12; vol. 4, Issue 12, No. e8446.

Lyke, et al.; "Association of Intraleukocytic Plasmodium Falciparum Malaria Pigment with Disease Severity, Clinical Manifestations, and Prognosis in Severe Malaria"; Am. J. Trop. Med. Hyg.; bearing a date of 2003; pp. 253-259; vol. 69, No. 3; The American Society of Tropical Medicine and Hygiene.

Mao, et al.; "Third Harmonic Generation in Self-Focused Filaments in Liquids"; bearing a date of 2007; pp. 1-5; Optical Society of America.

Mungthin, et al.; "Central Role of Hemoglobin Degradation in Mechanisms of Action of 4-Aminoquinolines, Quinoline Methanols, and Phenanthrene Methanols"; Antimicrobial Agents and Chemotherapy; bearing a date of Nov. 1998; pp. 2973-2977; vol. 42, No. 11; American Society for Microbiology.

Newman, et al.; "A Magneto-Optic Route Toward The In Vivo Diagnosis for Malaria: Preliminary Results and Preclinical Trial Data"; Biophysical Journal; bearing a date of Jul. 2008; pp. 994-1000; vol. 95; Biophysical Society.

Orjih; "Heme Polymerase Activity and the Stage Specificity of Antimalarial Action of Chloroquine"; The Journal of Pharmacology and Experimental Therapeutics; bearing a date of Mar. 6, 1997; pp. 108-112; vol. 282, No. 1; The American Society for Pharmacology and Experimental Therapeutics.

Orjih; "On the Mechanism of Hemozoin Production in Malaria Parasites: Activated Erythrocyte Membranes Promote B-Hematin Synthesis"; Exp Bio Med; bearing a date of 2001; pp. 746-752; vol. 226, No. 8; The Society for Experimental Biology and Medicine.

Oron, et al.; "Harmonic Generation with Temporally Focused Ultrashort Pulses"; J. Opt. Soc. Am. B; bearing a date of Dec. 2005; pp. 2660-2663; vol. 22, No. 12; Optical Society of America.

Oron, et al.; "Third-Harmonic Generation with Cylindrical Gaussian Beams"; J. Opt. Soc. Am. B; bearing a date of Nov. 2004; pp. 1964-1968; vol. 21, No. 11; Optical Society of America.

Pandey, et al.; "Mechanism of Malarial Haem Detoxification Inhibition by Chloroquine"; Biochem. J.; bearing a date of Aug. 22, 2000; pp. 333-358; vol. 355; Biochemical Society.

Parroche, et al.; "Malaria Hemozoin is Immunologically Inert but Radically Enhances Innate Responses by Presenting Malaria DNA to Toll-Like Receptor 9"; PNAS; bearing a date of Feb. 6, 2007; pp. 1919-1924 (plus cover page); vol. 104, No. 6; The National Academy of Sciences of the USA; located at: www.pnas.org/cgi/doi/10.1073/pnas.0608745104.

Ribaut, et al.; "Methodology: Concentration and Purification by Magnetic Separation of the Erythrocytic Stages of all Human Plasmodium Species"; BioMed Central, Malaria Journal; bearing a date of Mar. 5, 2008; 5 pgs.; vol. 7, No. 45; BioMed Central Ltd.

Sheetz, et al,.; "Ultrafast Optics: Imaging and Manipulating Biological Systems"; Journal of Applied Physics, Applied Physics Reviews-Focused Review; bearing a date of 2009; pp. 051101-1 through 051101-17; vol. 105, No. 051101; American Institute of Physics.

Sienkiewicz, et al.; "Multi-Frequency High-Field EPR Study of Iron Centers in Malarial Pigments"; JACS Communications; bearing a date of 2006; pp. 4534-4535; vol. 128; American Chemical Society.

Squier, et al.; "Third Harmonic Generation Microscopy"; Optics Express; bearing a date of Oct. 26, 1998; pp. 315-324; vol. 3, No. 9; Optical Society of America.

(56) References Cited

OTHER PUBLICATIONS

Tai, et al.; "In vivo Optical Biopsy of Hamster Oral Cavity with Epi-Third-Harmonic-Generation Microscopy"; Optics Express; bearing a date of Jun. 26, 2006; pp. 6178-6187; vol. 14, No. 13; Optical Society of America.

Tai, et al.; "In vivo Molecular-Resonant Third Harmonic Generation Microscopy of Hemoglobin"; CTuF4.pdf; bearing a date of 2007; pp. 1-2; Optical Society of America.

Tekwani, et al.; "Targeting the Hemozoin Synthesis Pathway for New Antimalarial Drug Discovery: Technologies for in vitro B-Hematin Formation Assay"; Combinatorial Chemistry & High Throughput Screening; bearing a date of 2005; pp. 63-79; vol. 8; Bentham Science Publishers Ltd.

"Third Harmonic Generator"; Del Mar Photonics, Instruction Manual; pp. 1-17; Model ATsG800-7.

Wang, et al.; "Evaluation of a Multi-Wavelength Reflectance System for Determination of Tissue Optical Properties in the UVA-VIS"; CFC5.pdf; bearing a date of 2007; pp. 1-2; Optical Society of America.

Yelin, et al.; "Third-Harmonic Microscopy with a Titanium-Sapphire Laser"; Applied Physics B, Lasers and Optics; bearing a date of 2002; pp. S97-S101; vol. 74; Springer-Verlag.

Yelin, et al.; "Laser Scanning Third-Harmonic-Generation Microscopy in Biology"; Optics Express; bearing a date of Oct. 11, 1999; pp. 169-175; vol. 5, No. 8; Optical Society of America.

Zheng, et al.; "Multichannel Multiphoton Imaging of Metal Oxides Particles in Biological System"; Proceeding of SPIE; bearing a date of 2004; pp. 5323-5355.

Zimmerman, et al.; "Diagnosis of Malaria by Magnetic Deposition Microscopy"; Am. J. Trop. Med. Hyg.; bearing a date of 2006; pp. 568-572; vol. 74, No. 4; The American Society of Tropical Medicine and Hygiene.

Zoueu, et al.; "Optical Microscope Based on Multispectral Imaging Applied to Plasmodium Diagnosis"; Journal of Applied Sciences; bearing a date of 2008; pp. 2711-2717; vol. 8, No. 15; Asian Network for Scientific Information.

Jamjoom; "Dark-field microscopy for detection of malaria in unstained blood films"; Journal of Clinical Microbiology; bearing a date of May 1983; pp. 717-721 (plus cover page); vol. 17, No. 5; American Society for Microbiology.

"Magnetic fields may hold key to malaria treatment, UW researches find"; UW Today; bearing a date of Mar. 30, 2000; pp. 1-2; University of Washington News Archives.

European Patent Office, Supplementary European Search Report, Pursuant to Rule 62 EPC; App. No. EP 11838344; Jul. 25, 2014 (received by our Agent on Aug. 7, 2014); 11 pages.

European Patent Office, Supplementary European Search Report, Pursuant to Rule 62 EPC; App. No. 11742583; Jul. 23, 2014 (received by our Agent on Aug. 7, 2014); 8 pages.

European Patent Office, Extended European Search Report, Pursuant to Rule 62 EPC; App. No. EP 10 80 2974; Jan. 26, 2015 (received by our Agent on Jan. 30, 2015); pp. 1-7.

* cited by examiner

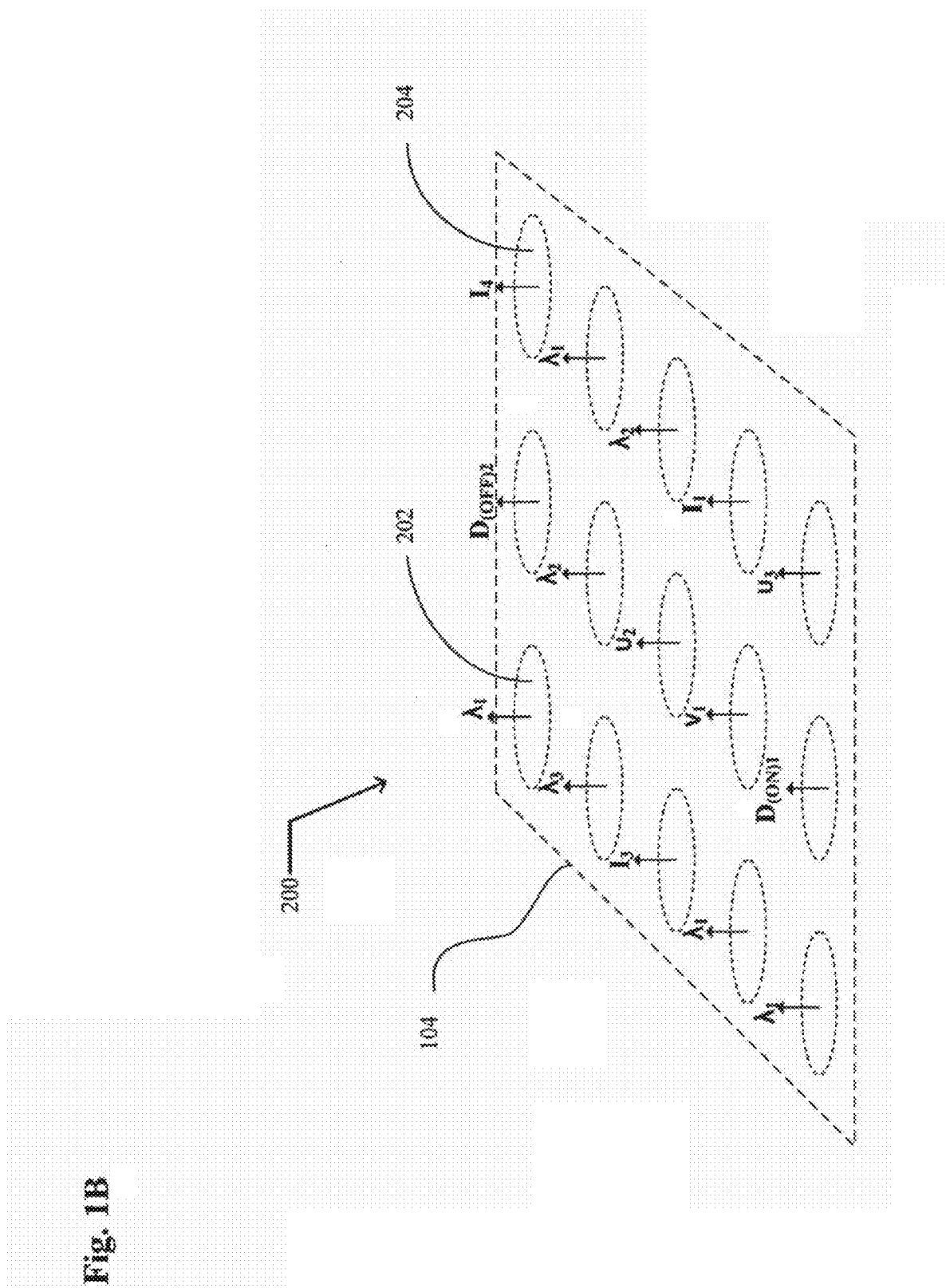

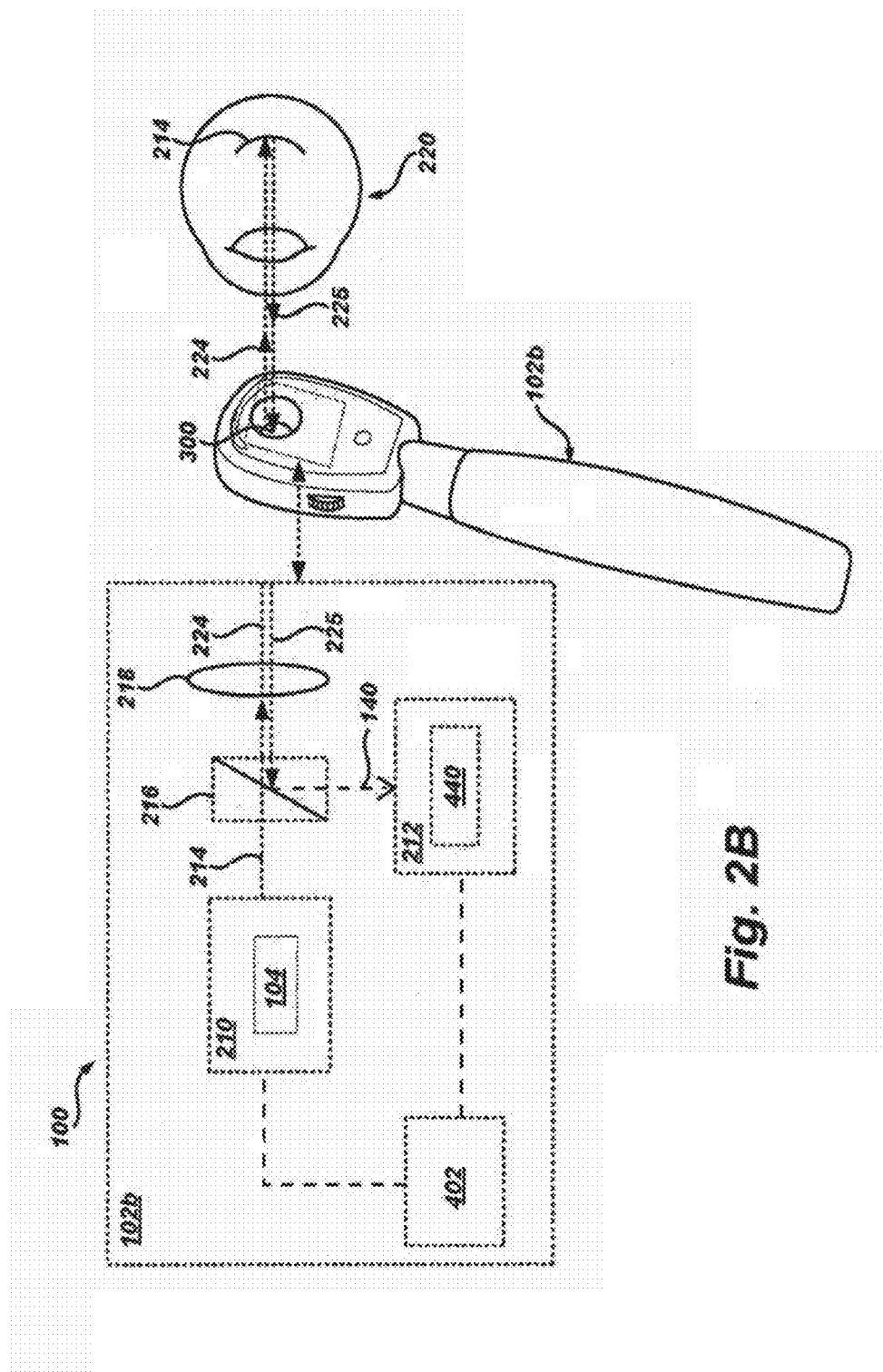

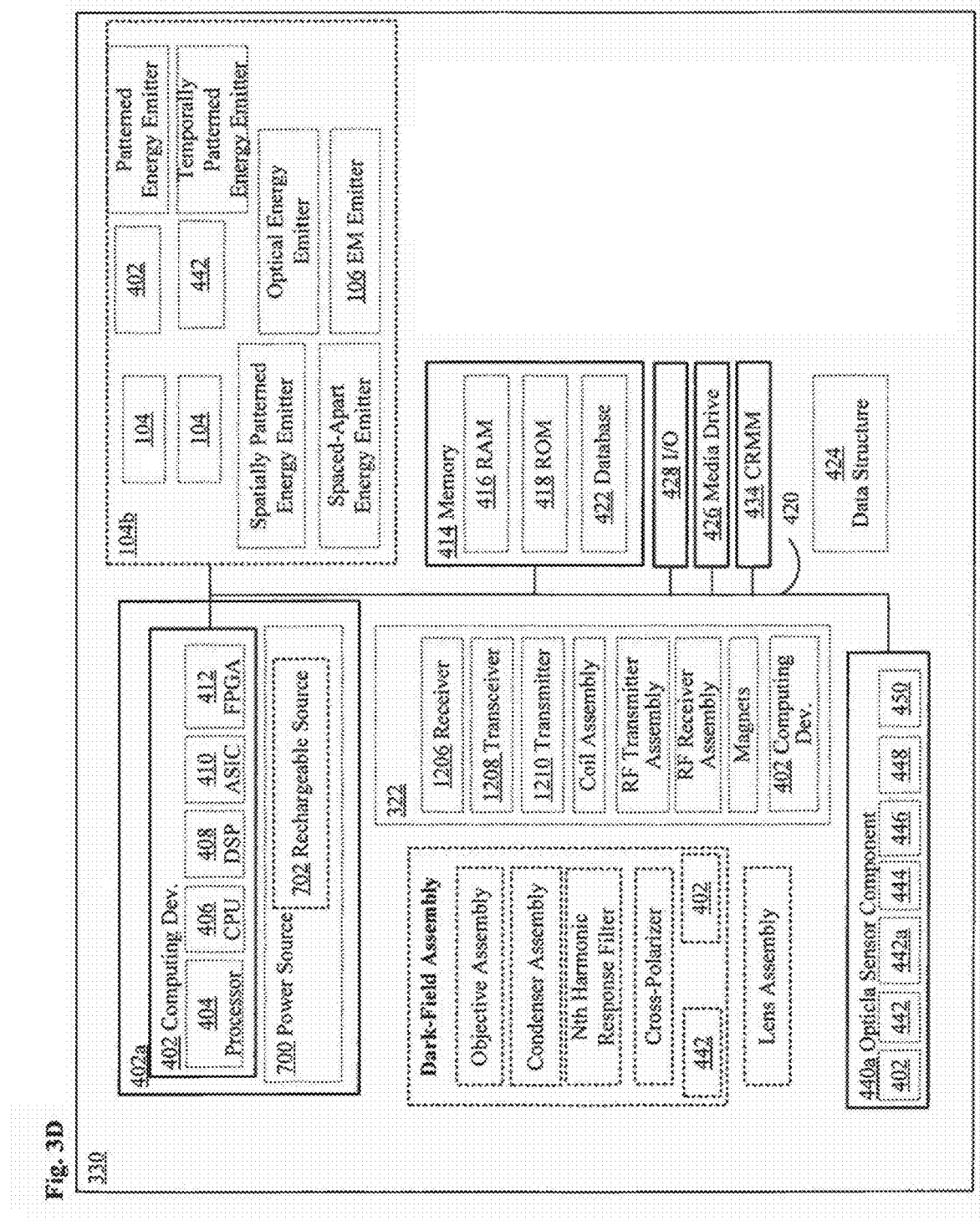

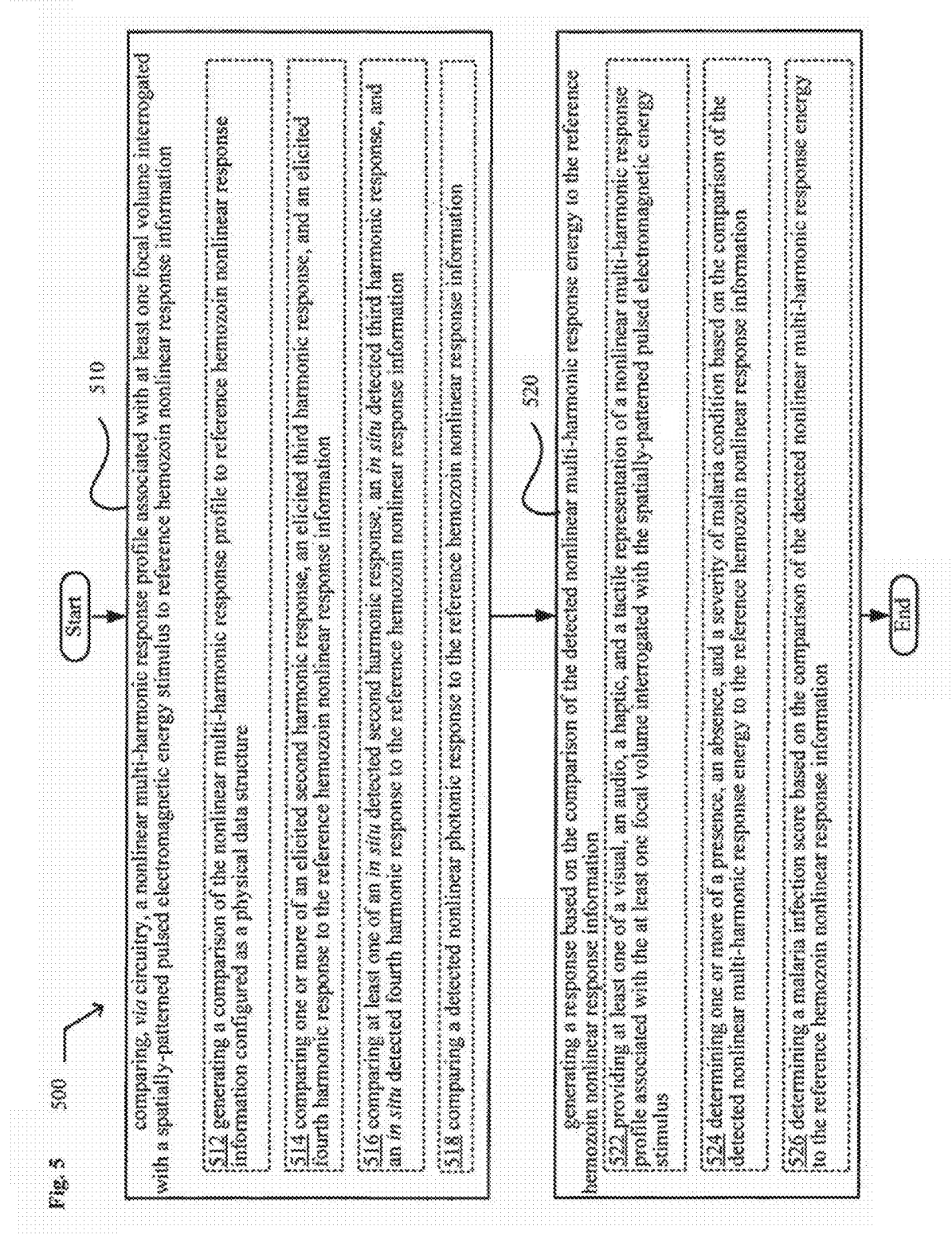

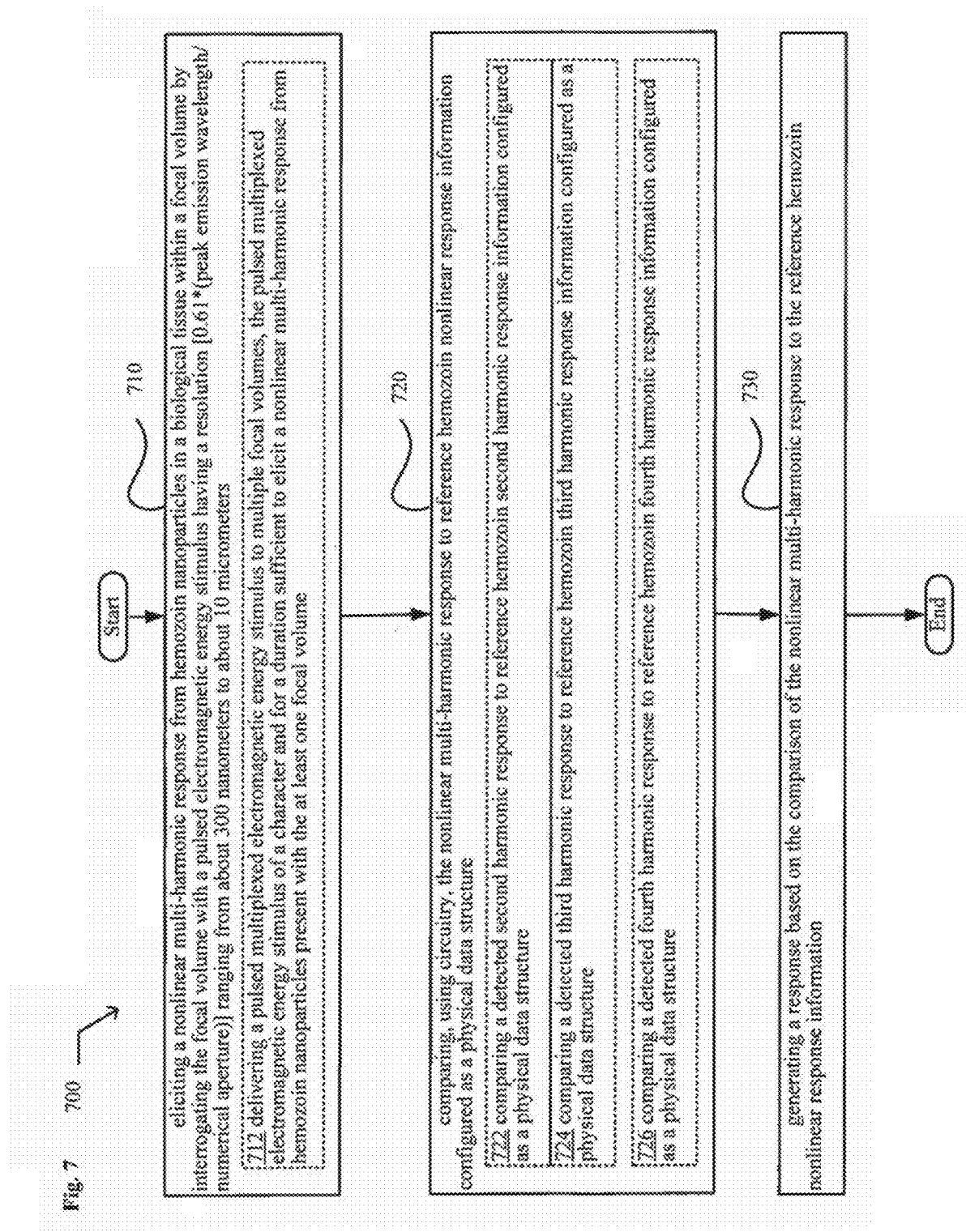

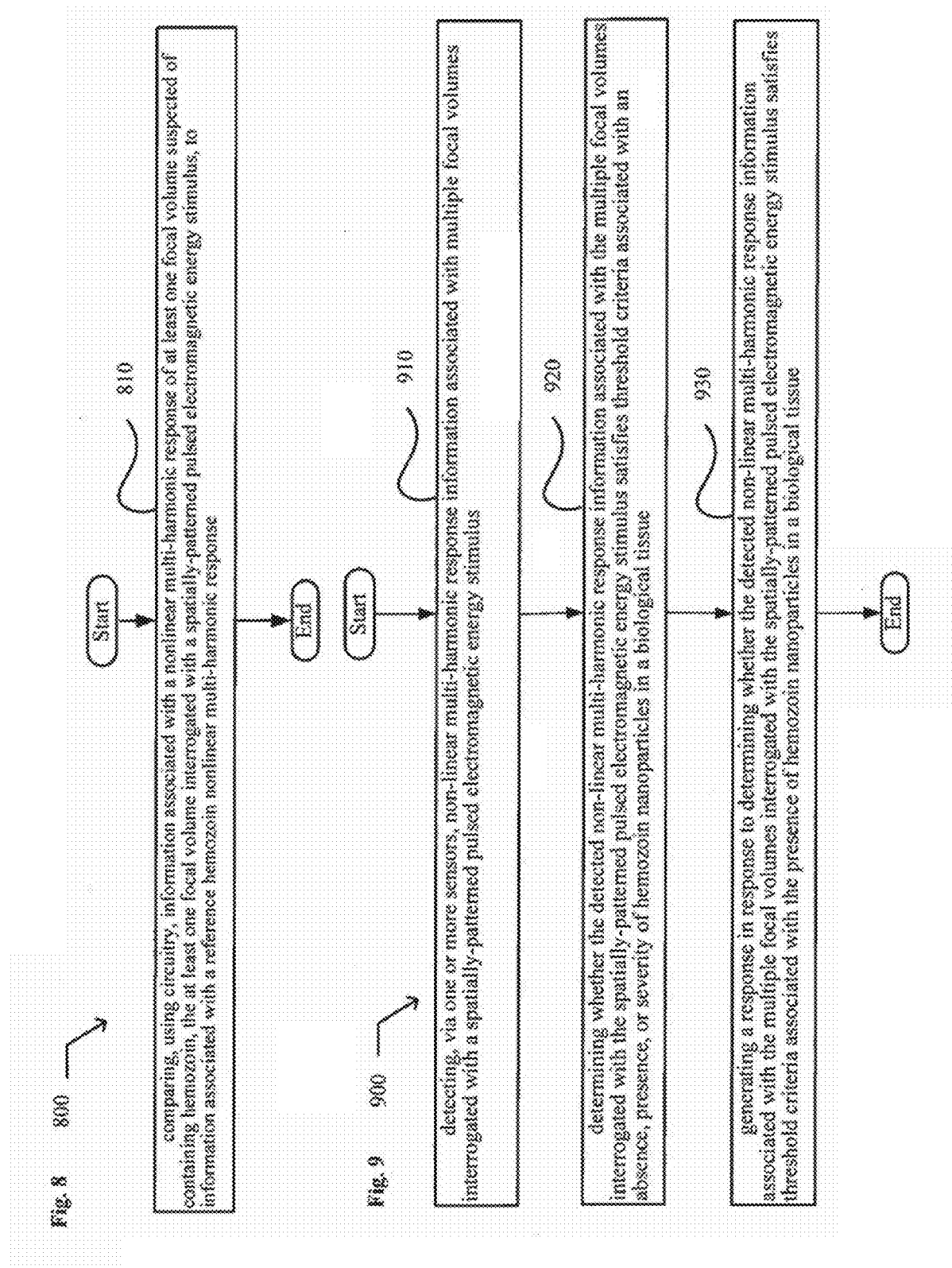

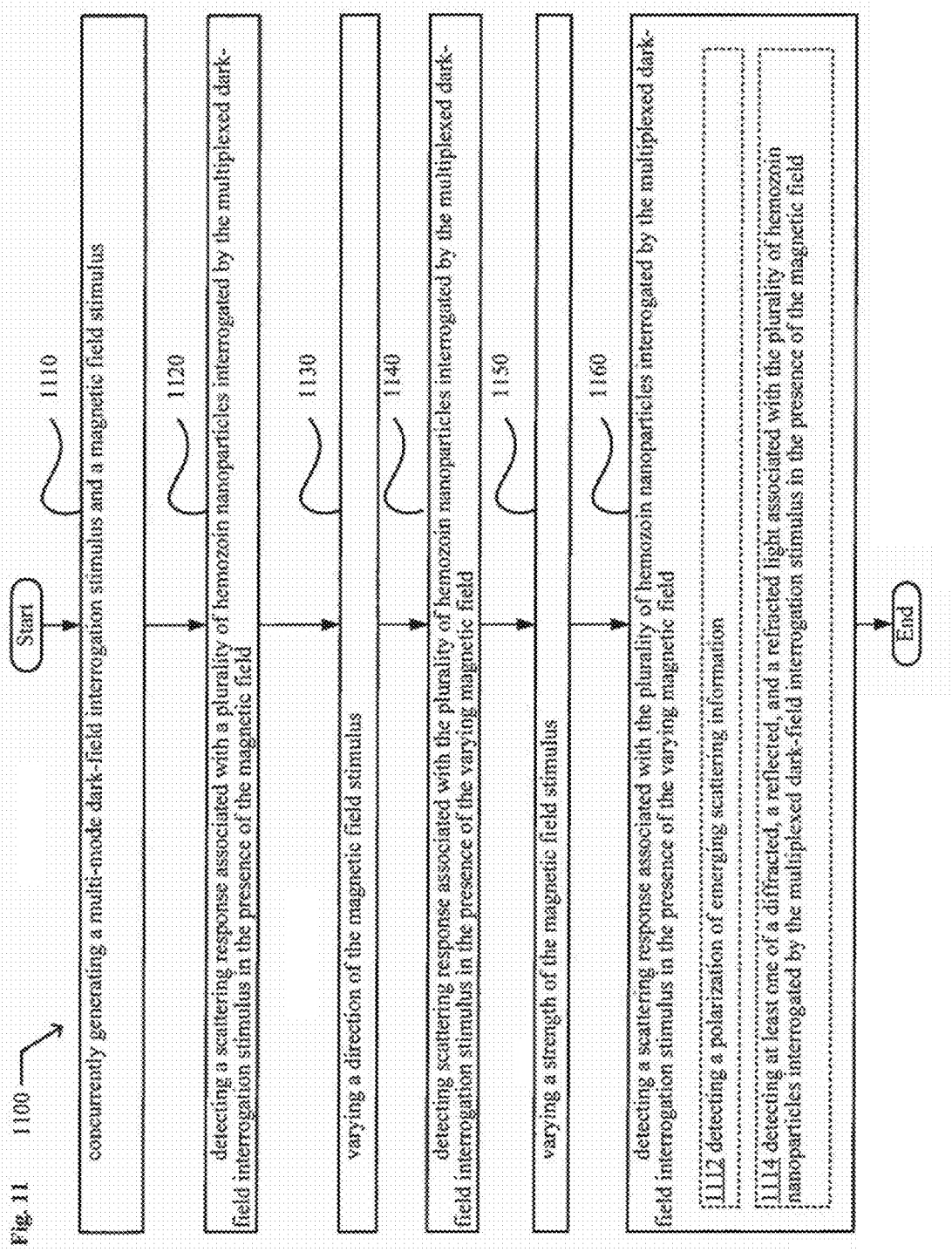

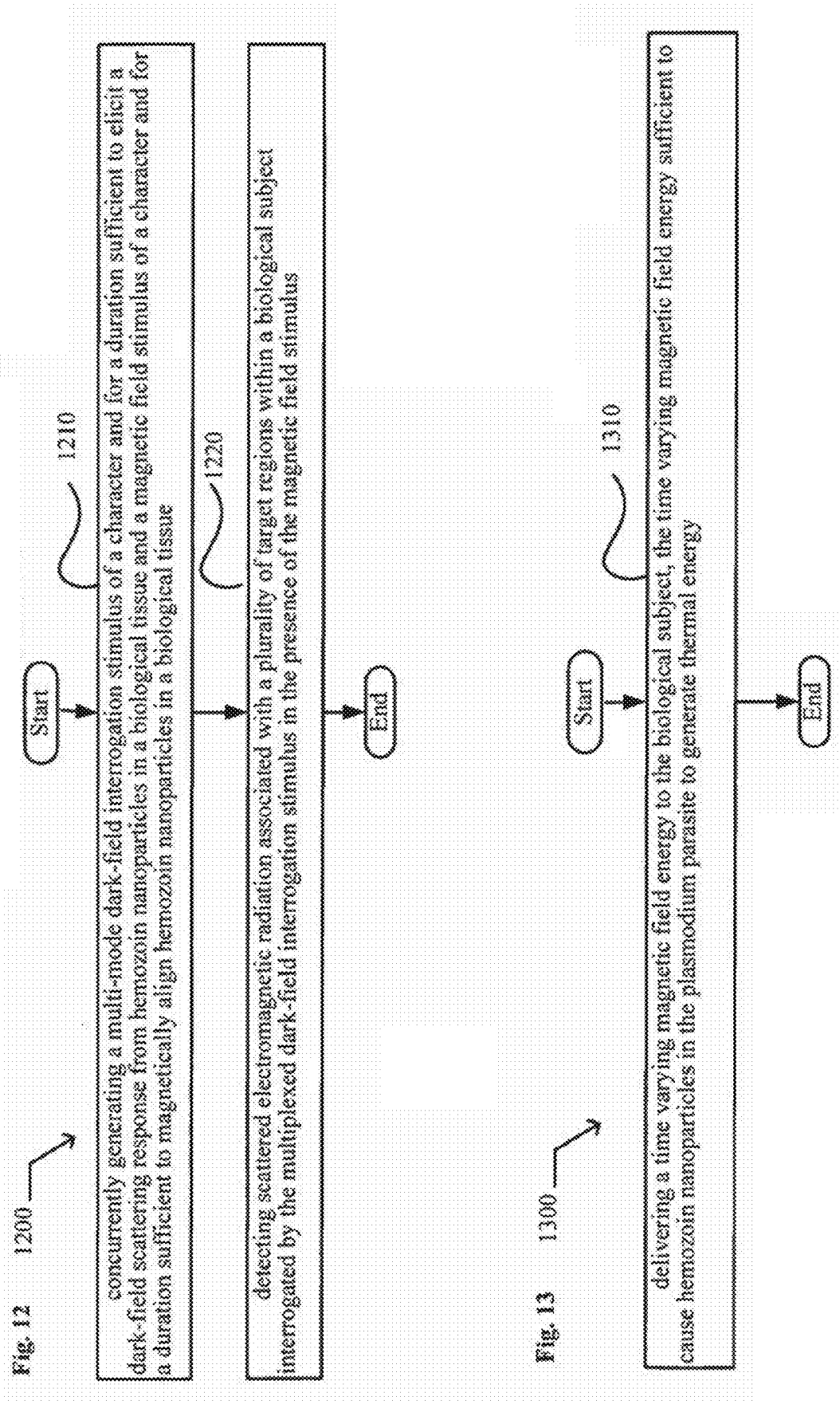

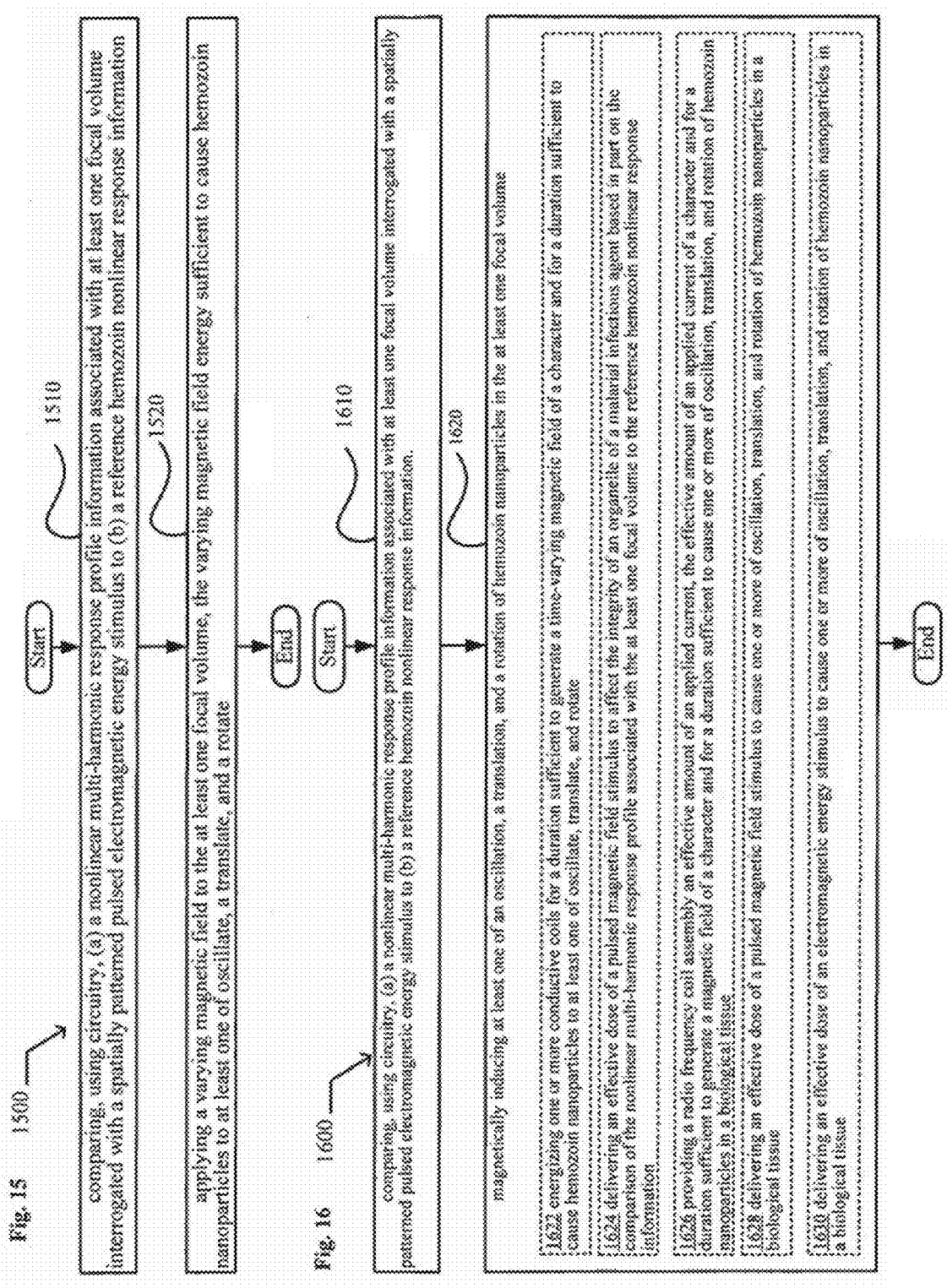

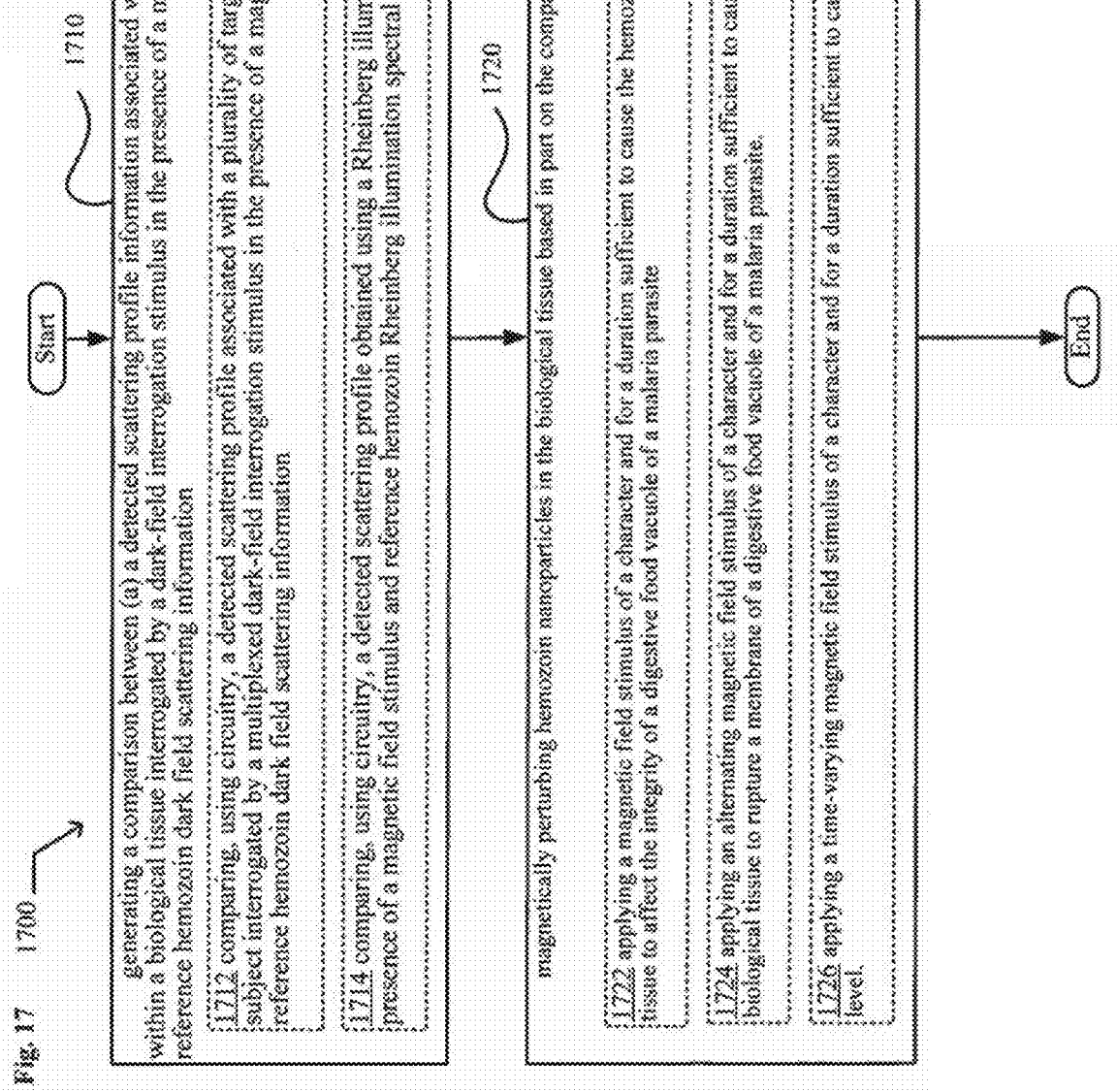

Fig. 18A 1800

1810: eliciting a nonlinear multi-harmonic response from hemozoin nanoparticles in a biological tissue by interrogating a pl

1826 irradiating hemozoin nanoparticles in a biological tissue within one or more of the plurality of focal volumes with electromagnetic energy having a peak emission wavelength of about 788 nanometers 1828 irradiating the hemozoin nanoparticles in a biological tissue within one or more of the plurality of focal volumes with electromagnetic energy of a character and for a duration to cause a portion of the hemozoin nanoparticles in a biological tissue to generate a nonlinear multi-harmonic response having a wavelength ranging from about 233 nanometers to about 434 nanometers

1830

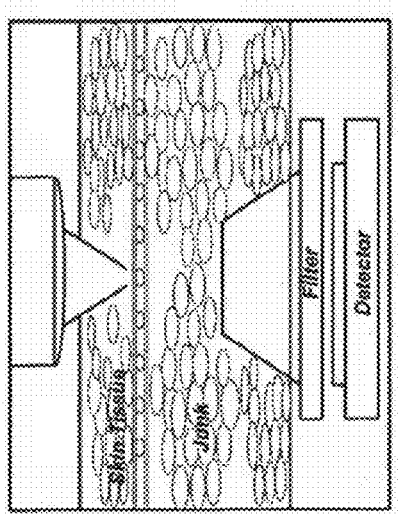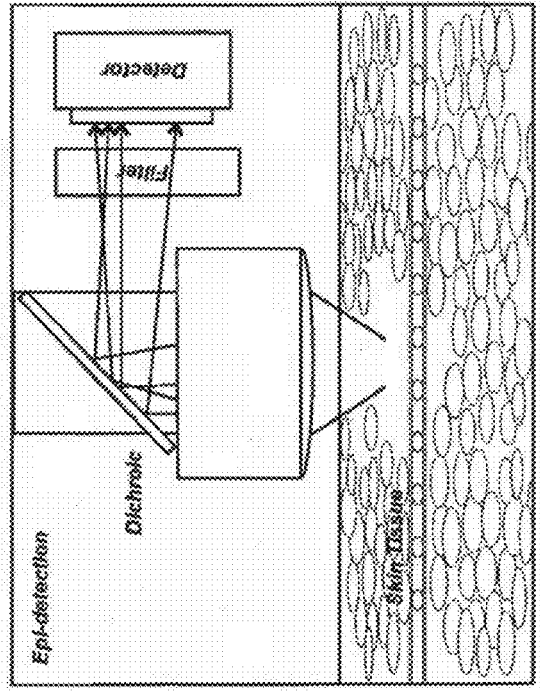
Fig. 31A
Fig. 31B

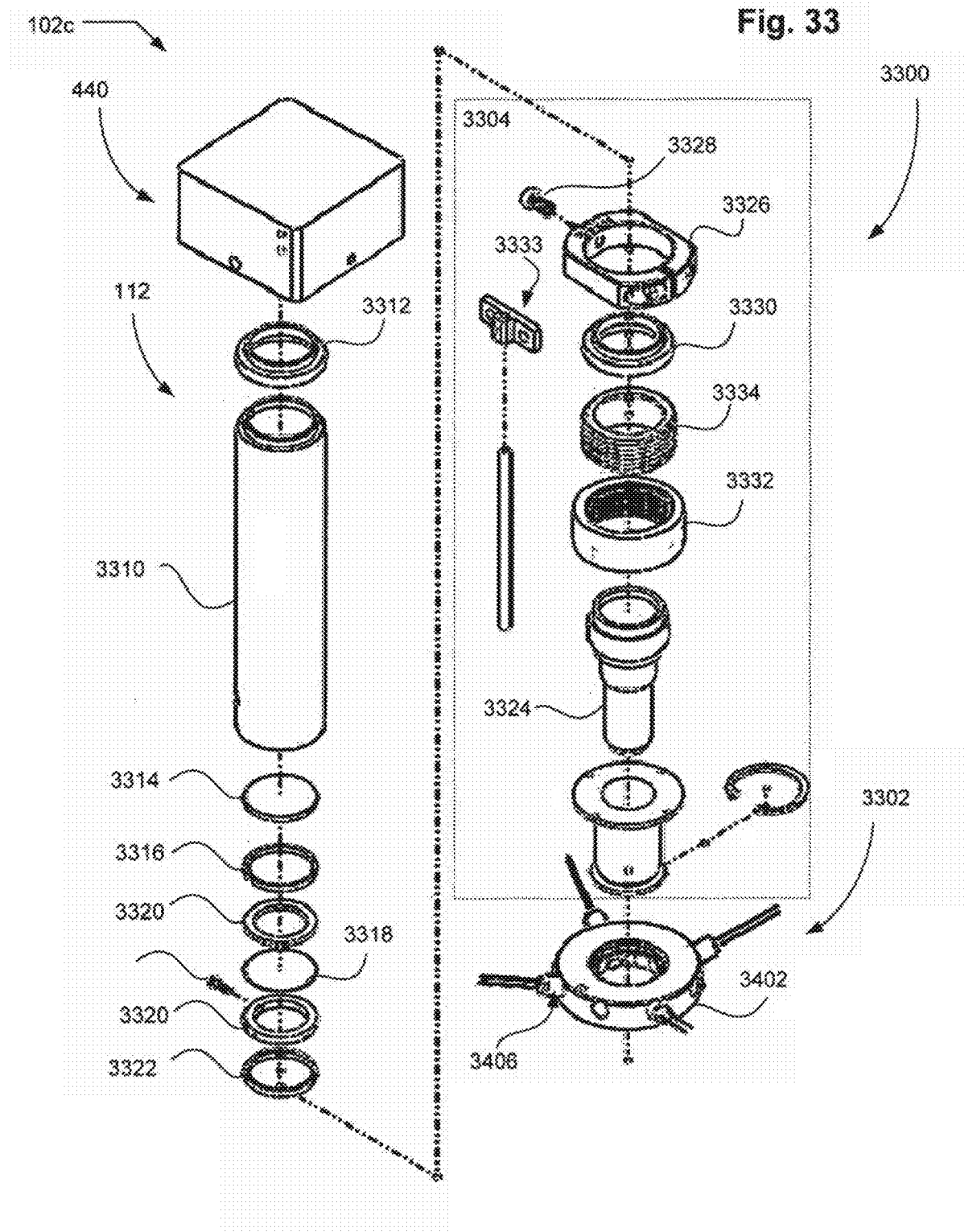

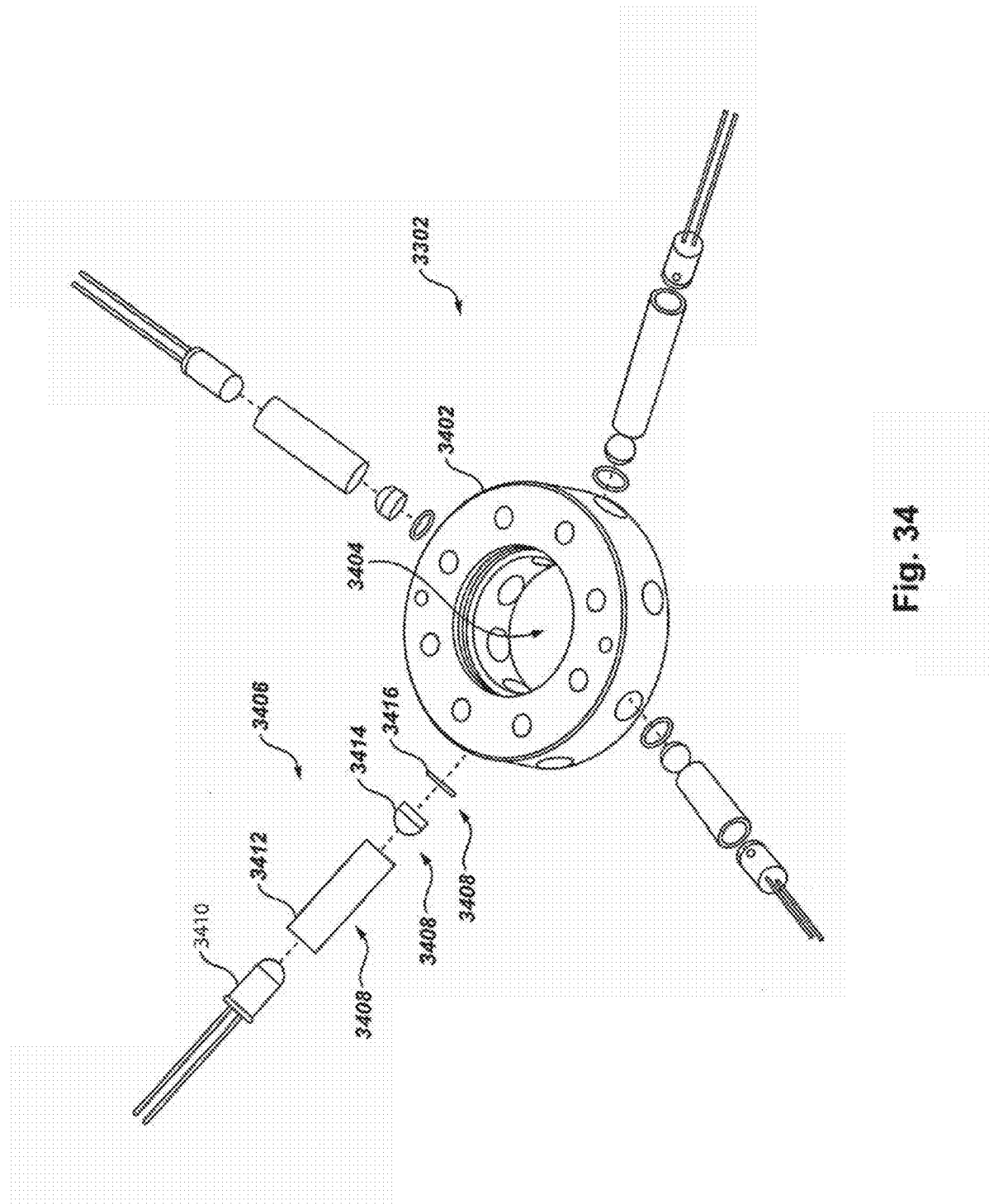

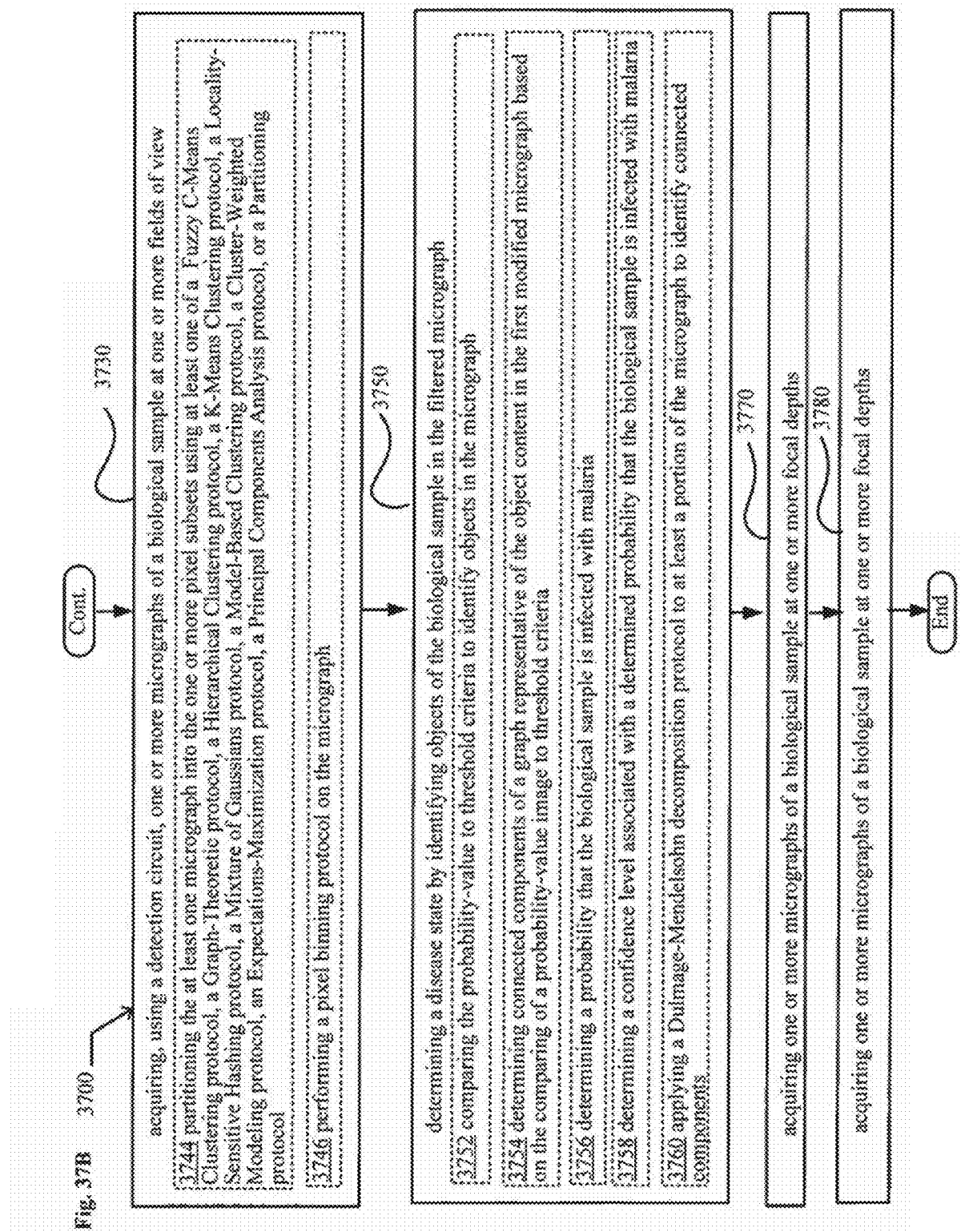

SYSTEMS, DEVICES, AND METHODS FOR DETECTION OF MALARIA

CROSS-REFERENCE TO RELATED APPLICATIONS

All subject matter of the Related Applications and of any and all parent, grandparent, great-grandparent, etc. applications of the Related Applications is incorporated herein by reference to the extent such subject matter is not inconsistent herewith.

RELATED APPLICATIONS

For purposes of the USPTO extra-statutory requirements, the present application constitutes a continuation-in-part of U.S. patent application Ser. No. 12/925,650, entitled SYSTEMS, DEVICES, AND METHODS FOR DETECTION OF MALARIA, naming MATTHEW R. BEHREND, MICHAEL C. HEGG, MATTHEW P. HORNING, and BENJAMIN K. WILSON as inventors, filed 25 Oct. 2010, which is currently co-pending or is an application of which a currently co-pending application is entitled to the benefit of the filing date.

For purposes of the USPTO extra-statutory requirements, the present application constitutes a continuation-in-part of U.S. patent application Ser. No. 12/658,619, titled SYSTEMS, DEVICES, AND METHODS INCLUDING MULTI-HARMONIC OPTICAL DETECTION OF HEMOZOIN NANOPARTICLES, naming MICHAEL C. HEGG, MATTHEW P. HORNING, JORDIN T. KARE, NATHAN P. MYHRVOLD, CLARENCE T. TEGREENE, BENJAMIN K. WILSON, LOWELL L. WOOD, JR, as inventors, filed 10, Feb., 2010, which is currently co-pending or is an application of which a currently co-pending application is entitled to the benefit of the filing date.

For purposes of the USPTO extra-statutory requirements, the present application constitutes a continuation-in-part of U.S. patent application Ser. No. 12/658,580, titled SYSTEMS, DEVICES, AND METHODS INCLUDING ENHANCED DARK FIELD DETECTION OF HEMOZOIN NANOPARTICLES naming MICHAEL C. HEGG, MATTHEW P. HORNING, JORDIN KARE, NATHAN P. MYHRVOLD, CLARENCE, T. TEGREENE, BENJAMIN K. WILSON, LOWELL L. WOOD, JR. as inventors, filed 10, Feb., 2010, which is currently co-pending or is an application of which a currently co-pending application is entitled to the benefit of the filing date.

For purposes of the USPTO extra-statutory requirements, the present application constitutes a continuation-in-part of U.S. patent application Ser. No. 12/658,617, titled SYSTEMS, DEVICES, AND METHODS INCLUDING PARAMAGNETIC OSCILLATION, POTATION AND TRANSLATION OF HEMOZOIN ASYMMETRIC NANOPARTICLES IN RESPONSE TO MULTI-HARMONIC OPTICAL DETECTION OF THE PRESENCE OF HEMOZOIN, naming MICHAEL C. HEGG, MATTHEW P. HORNING, JORDIN T. KARE, NATHAN P. MYHRVOLD, CLARENCE T. TEGREENE, BENJAMIN K. WILSON, LOWELL L. WOOD, JR. as inventors, filed 10 Feb. 2010, which is currently co-pending or is an application of which a currently co-pending application is entitled to the benefit of the filing date.

For purposes of the USPTO extra-statutory requirements, the present application constitutes a continuation-in-part of U.S. patent application Ser. No. 12/658,638, titled SYSTEMS, DEVICES, AND METHODS INCLUDING PARAMAGNETIC OSCILLATION, ROTATION AND TRANSLATION OF HEMOZOIN ASYMMETRIC NANOPARTICLES IN RESPONSE TO MULTI-HARMONIC OPTICAL DETECTION OF THE PRESENCE OF HEMOZOIN, naming MICHAEL C. HEGG, MATTHEW P. HORNING, JORDIN T. KARE, NATHAN P. MYHRVOLD, CLARENCE T. TEGREENE, BENJAMIN K. WILSON, LOWELL L. WOOD. JR. as inventors, filed 19, Feb., 2010, which is currently co-pending or is an application of which a currently co-pending application is entitled to the benefit of the filing date.

For purposes of the USPTO extra-statutory requirements, the present application constitutes a continuation-in-part of U.S. patent application Ser. No. 12/658,589, titled SYSTEMS, DEVICES, AND METHODS INCLUDING PARAMAGNETIC OSCILLATION, ROTATION, AND TRANSLATION OF HEMOZOIN ASYMMETRIC NANOPARTICLES IN RESPONSE TO DARK-FIELD OR RHEINBERG DETECTION OF THE PRESENCE OF HEMOZOIN, naming MICHAEL C. HEGG, MATTHEW P. HORNING, JORDIN T. KARE, NATHAN P. MYHRVOLD, CLARENCE T. TEGREENE, BENJAMIN K. WILSON, LOWELL L. WOOD, JR. as inventors, filed 10, Feb., 2010, which is currently co-pending or is an application of which a currently co-pending application is entitled to the benefit of the filing date.

For purposes of the USPTO extra-statutory requirements, the present application constitutes a continuation-in-part of U.S. patent application Ser. No. 12/658,607, titled SYSTEMS, DEVICES, AND METHODS FOR INDUCING ULTRAVIOLET ENERGY GENERATION VIA HEMOZOIN NANOPARTICLES IN A BIOLOGICAL TISSUE, naming MICHAEL C. HEGG, MATTHEW P. HORNING, JORDIN T. ARE NATHAN P. MYHRVOLD, CLARENCE T. TEGREENE, BENJAMIN K. WILSON, LOWELL L. WOOD, JR. as inventors, filed 10, Feb., 2010, which is currently copending or is an application of which a currently co-pending application is entitled to the benefit of the tiling date.

The USPTO has published a notice to the effect that the USPTO's computer programs require that patent applicants reference both a serial number and indicate whether an application is a continuation or continuation-in-part. Stephen G. Kunin, Benefit of Prior-Filed Application, USPTO Official Gazette Mar. 18, 2003, available at http://www.uspto.gov/web/offices/com/sol/og/2003/week11/patbene.htm.
The present Applicant Entity (hereinafter "Applicant") has provided above a specific reference to the application(s) from which priority is being claimed as recited by statute. Applicant understands that the statute is unambiguous in its specific reference language and does not require either a serial number or any characterization, such as "continuation" or "continuation-in-part," for claiming priority to U.S. patent applications. Notwithstanding the foregoing. Applicant understands that the USPTO's computer programs have certain data entry requirements, and hence Applicant is designating the present application as a continuation-in-pan of its parent applications as set forth above, but expressly points out that such designations are not to be construed in any way as any type of commentary and/or admission as to whether or not the present application contains any new matter in addition to the matter of its parent application(s).

All subject matter of the Related Applications and of any and all parent, grandparent, great-grandparent etc. applications of the Related Applications is incorporated herein by reference to the extent such subject matter is not inconsistent herewith.

SUMMARY

In an aspect, the present disclosure is directed to among other things, a dark-field reflected-illumination apparatus. In an embodiment, the dark-field reflected-illumination apparatus includes a dark-field illuminator and means for adjusting a dark-field illuminator distance relative to an optical assembly. In an embodiment, the dark-field illuminator includes a body structure having an aperture and a plurality of waveguide assemblies. In an embodiment, the plurality of waveguide assemblies include one or more electromagnetic energy waveguides configured to be coupled to at least one electromagnetic energy emitter. In an embodiment, the plurality of waveguide assemblies are oriented to focus electromagnetic energy onto at least one focal region within the aperture and at one or more angles of incidence relative to an optical axis of an optical assembly.

In an aspect, the present disclosure is directed to, among other things, malaria detection apparatus, in an embodiment, the malaria detection apparatus includes an optical assembly having a sample side, a detector side, and an optical axis therethrough. In an embodiment, the malaria, detection apparatus includes a dark-field illuminator and a detector. In an embodiment, the malaria detection apparatus includes means for adjusting a dark-field illuminator distance relative to the optical assembly along an axis substantially parallel to an optical axis of the optical assembly. In an embodiment, the dark-field illuminator includes a plurality of waveguide assemblies, and a body structure having an aperture aligned along an axis substantially parallel to an optical axis. In an embodiment, the optical assembly is configured to receive scattered electromagnetic energy from a ample interrogated by the dark-field illuminator. In an embodiment, the detector includes one or more sensor 442 that capture one or more micrographs associated with the scattered electromagnetic energy from the sample interrogated by the dark-field illuminator.

In an aspect, the present disclosure is directed to among other things, a system. In an embodiment, the system includes a detection circuit configured to acquire one or more micrographs of a biological sample at one or more fields of view. In an embodiment, the system includes a resolution modification circuit configured to modify a pixel count of at least one micrograph and to generate at least a first modified micrograph. In an embodiment, the system includes a filter-kernel generation circuit configured to generate a kernel for filtering a plurality of pixels forming the first modified micrograph based on a filtering characteristic, and to generate at least a first significance image representative of the at least one modified micrograph. In an embodiment, the system includes an object identification circuit configured to identify groups of pixels in the first significance image indicative of one or more objects imaged in the at least one micrograph, and to generate one or more connected components of a graph representative of groups of pixels indicative of the one or more objects imaged in the at least one micrograph.

In an aspect, the present disclosure is directed to, among other things, a method including acquiring, using a detection circuit, one or more micrographs of a biological sample at one or more fields of view, in an embodiment, the method includes modifying a resolution of at least one of the one or more micrographs and generating at least a first modified micrograph. In an embodiment, the method includes generating a first filtered micrograph by filtering the at least first modified micrograph based on a filtering protocol. In an embodiment, the method includes determining a disease state by identifying objects of the biological sample in the filtered micrograph.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

FIG. 1B is a top plan view of a portion of a monitor or treatment device including at least one energy emitting component delivering a patterned electromagnetic energy stimulus, according to one embodiment.

FIG. 2B is a perspective view of a system for monitoring/modulating a plasmodium parasitic activity according to one embodiment.

FIG. 3D is a perspective view of an in situ hemozoin-monitoring device according to one embodiment.

FIG. 5 is a flow diagram of a method according to one embodiment.

FIG. 7 is a flow diagram of a method according to one embodiment.

FIG. 8 is a flow diagram of a method according to one embodiment.

FIG. 9 is a flow diagram of a method according to one embodiment.

FIG. 11 is a flow diagram of a method according to one embodiment.

FIG. 12 is a flow diagram of a method according to one embodiment.

FIG. 13 is a flow diagram of a method according to one embodiment.

FIG. 15 is a flow diagram of a method according to one embodiment.

FIG. 16 is a flow diagram of a method according to one embodiment.

FIG. 17 is a flow diagram of a method according to one embodiment.

FIGS. 18A and 18B show a flow diagram of a method according to one embodiment.

FIG. 31A is a prospective view of a monitor or treatment device according to one embodiment.

FIG. 31B is a prospective view of a monitor or treatment device using epi-detection according to one embodiment.

FIG. 33 is an exploded view of a monitor gar treatment device using Dark field detection according to one embodiment.

FIG. 34 is an exploded view of a Dark-field illuminator according to one embodiment.

FIGS. 37A and 37B show a flow diagram of a method according to one embodiment.

DETAILED DESCRIPTION

Figure 1A:
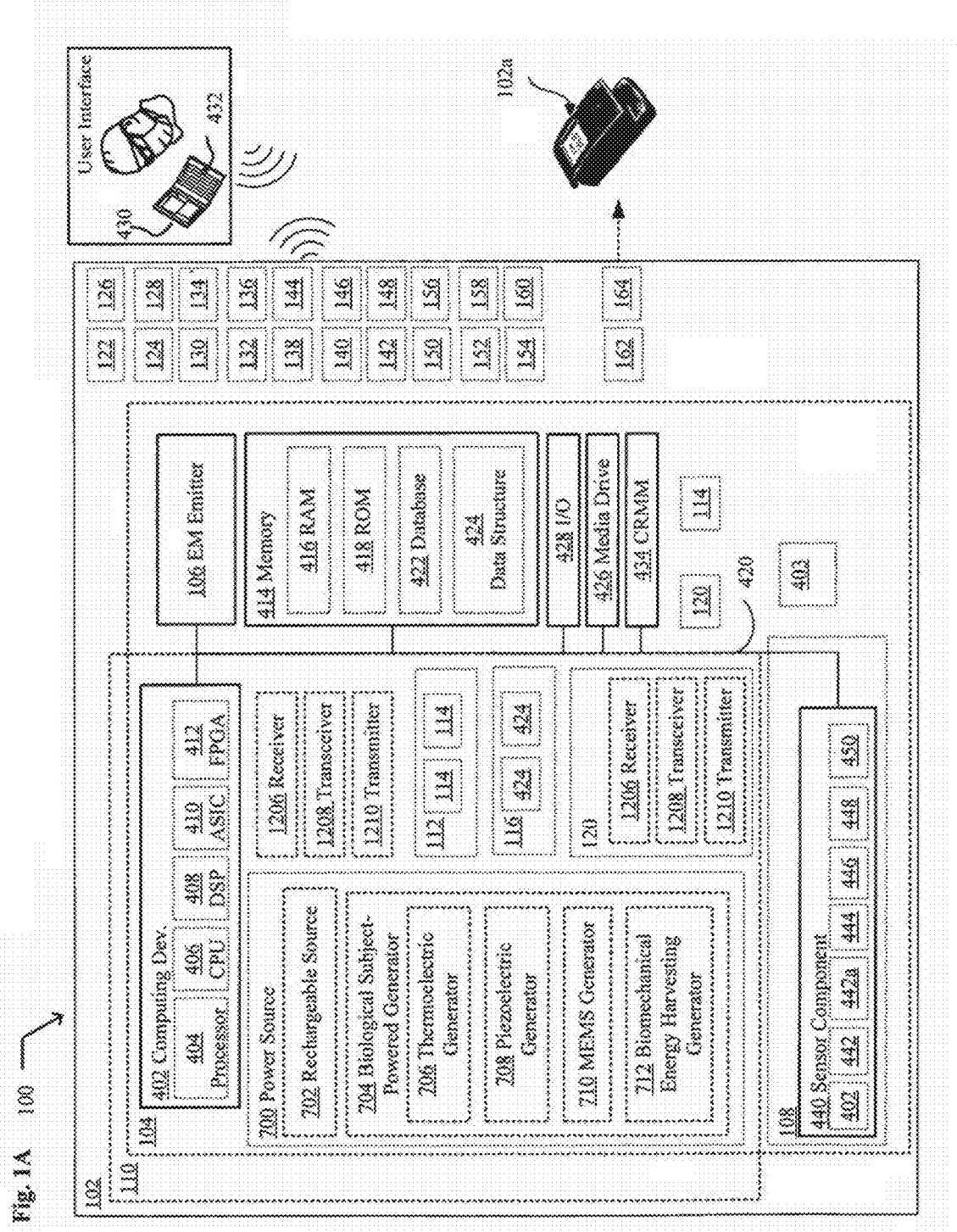
FIG. 1A is a perspective view of a system according to one embodiment.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

An aspect of the disclosure includes systems, devices, and methods for detecting (e.g., assessing, calculating, evaluating, determining, gauging, identifying, measuring, monitoring, quantifying, resolving, sensing, or the like) an agent marker present m, for example, as biological sample blood, bone, muscle, skin, adipose tissue, fluid, tendons, organs, ventricles, or the like, either in vivo or in vitro). Agent markers can include markers indicating the presence of an infectious agent, for example. A non-limiting example includes systems, devices, and methods of actively monitoring a biological subject suspected of being infected with a plasmodium parasite. A non-limiting example includes systems, devices, and methods including dark-field or Rheinberg detection technologies and methodologies.

Malaria remains one of the most important communicable diseases in the world. The World Health Organization estimates that about half of the world's population lives in areas having some risk of exposure to malaria. See, e.g., World Health Organization, *World Malaria Report* 2008, WHO: Geneva 9 (2008). Malaria is a vector-borne infectious disease caused by a eukaryotic protist of the genus *Plasmodium* Among *Plasmodium* species that can infect humans, examples include *Plasmodium falciparum, Plasmodium knowlesi, Plasmodium malariae, Plasmodium ovale*, and *Plasmodium vivax*. A 2006 World Health Organization estimate indicates that about 247 million cases of malaria occur annually of which 230 million are due to *Plasmodium falciparum*. See, e.g., World Health Organization, *World Malaria Report* 2008, WHO: Geneva 10 (2008).

The protozoan *Plasmodium* parasite, the agent of malaria, produces hemozoin (a birefringent heme crystal) while inside the hemoglobin-laden erythrocyte. See e.g., Lamikanra et al, *Hemozoin (Malarial Pigment) Directly Promotes Apoptosis of Etythroid Precursors*. PLoS ONE 4(12) (2009): e8446, doi:101371/journal.pone.0008446. Hemozoin, a biomarker for malaria, is synthesized during the degradation of hemoglobin and is found in the digestive food vacuole of intraerythrocytic *Plasmodium* parasites.

An aspect of the disclosure includes systems, devices, and methods including multi-harmonic optical detection of hemozoin nanoparticles. A non-limiting example includes systems, devices, and methods including enhanced dark field detection of hemozoin nanoparticles. An aspect of the disclosure includes systems, devices, methods, and compositions for actively detecting and treating a malarial infection. A non-limiting example includes systems, devices, and methods for heat-shocking malaria infected erythrocytes. A non-limiting example includes systems, devices, and methods including paramagnetic oscillation, rotation, and translation of hemozoin asymmetric nanoparticles in response to multi-harmonic optical detection of the presence of hemozoin. A non-limiting example includes systems, devices, and methods including ultraviolet energy generation via hemozoin nanoparticles in a biological tissue.

FIG. 1A shows a system 100, in which one or more methodologies or technologies can be implemented such as, for example, actively detecting or treating a malarial infection. In an embodiment, the system 100 includes, among other things, one or more monitor or treatment devices 102. Nonlimiting examples of monitor or treatment devices 102 include hemozoin-monitoring devices, spectrometers, antimalarial therapeutic devices, malarial retinal diagnostic devices, transcutaneous diagnostic devices 102a, ophthalmoscopes 102b (e.g., ophthalmoscopes employing nonlinear optics, dark-field, or Rheinberg detection configurations, technologies, and methodologies), parasitemia detectors, malaria detection apparatuses 102c, or the like.

In an embodiment, the system 100 includes, among other things, an energy-emitting component 104 configured to interrogate one or more focal volumes with an electromagnetic energy stimulus. Non-limiting examples of energy-emitting components 104 include electromagnetic radiation emitters, electric circuits, electrical conductors, cavity resonators, electro-mechanical components, electro-opto components, lasers, quantum dots, laser diodes, light-emitting diodes (e.g., organic light-emitting diodes, polymer light-emitting diodes, polymer phosphorescent light-emitting diodes, microcavity light-emitting diodes, high-efficiency light-emitting diodes, or the like), arc flashlamps, incandescent emitters, continuous wave bulbs, or the like. In an embodiment, the energy-emitting component 104 includes at least one two-photon excitation component, in an embodiment, the energy-emitting component 104 includes one or more lasers, laser diodes, and light-emitting diodes. In an embodiment, the energy-emitting component 104 includes one or more quantum dots, organic light-emitting diodes, microcavity light-emitting diodes, and polymer light-emitting diodes. In an embodiment, the energy-emitting component 104 includes at least one of an exciplex laser, a diode-pumped solid state laser, or a semiconductor laser. In an embodiment, the energy-emitting component 104 includes one or more tunable ultrafast lasers. In an embodiment, the energy-emitting component 104 includes one or more femtosecond lasers. In an embodiment, the energy-emitting component 104 includes one or more Ti:sapphire lasers. In an embodiment, the energy-emitting component 104 interrogates at least one focal volume with a spatially-patterned electromagnetic energy stimulus having at least a first region and a second region different from the first region. In an embodiment, the energy-emitting component 104 interrogates at least one focal volume with a spatially patterned electromagnetic energy stimulus having at least a first region and a second region, the second region having at least one of an illumination intensity, an energy emitting pattern, a peak emission wavelength, an ON-pulse duration, an OFF-pulse duration, or a pulse frequency different from the first region. In an embodiment, the energy-emitting component 104 interrogates at least one focal volume with a spatially patterned pulsed multiplexed electromagnetic energy stimulus. In an embodiment, the energy-emitting component 104 generates a multiplexed electromagnetic energy stimulus having, for example, two or more peak emission wavelengths.

In an embodiment, the electromagnetic energy-emitting component 104 is configured to direct (e.g., via one or more waveguides) electromagnetic radiation toward a biological sample (e.g., tissue, blood capillaries underneath the skin, or the like). If the biological sample is infected with malaria parasites, the hemozoin within them will emit a characteristic optical response back through the skin.

In an embodiment, by adjusting the wavelength of the electromagnetic stimulus generated by the energy emitting component 104, it is possible to control the wavelength of light that emerges from the hemozoin (i.e., it is possible to control the wavelength of the emerging nonlinear optical response of the hemozoin). In an embodiment, one or more peak emission wavelengths of the electromagnetic stimulus generated by the energy-emitting component 104 are chosen to elicit a nonlinear optical response of hemozoin to emit within a wavelength range that damages genetic material.

In an embodiment, the energy-emitting component 104 delivers a spatially-patterned pulsed multiplexed electromagnetic energy stimulus having a peak power ranging from about 400 gigawatts to about 8 terawatts. In an embodiment, the energy-emitting component 104 generates a spatially-patterned pulsed multiplexed electromagnetic energy stimulus having a peak irradiance of less than about 200 gigawatts/cm^2. In an embodiment, the energy-emitting component 104 generates a spatially-patterned pulsed multiplexed electromagnetic energy stimulus having an average power ranging from about 1 miliwatt to about 1 watt. In an embodiment, the energy-emitting component 104 generates a spatially-patterned pulsed multiplexed electromagnetic energy stimulus having one or more peak emission wavelengths ranging from about 690 nanometers to about 2000 nanometers. In an embodiment, the energy-emitting component 104 generates spatially-patterned pulsed multiplexed electromagnetic energy stimulus having a resolution [0.61* (peak emission wavelength/numerical aperture)] ranging from about 300 nanometers to about 10 micrometers. Energy-emitting components 104 forming part of a monitor or treatment device 102, can take a variety of forms, configurations, and geometrical patterns including for example, but not limited to, a one-, two-, or three-dimensional arrays, a pattern comprising concentric geometrical shapes, a pattern comprising rectangles, squares, circles, triangles, polygons, any regular or irregular shapes, or the like, or any combination thereof. One or more of the energy-emitting components 104 may have a peak emission wavelength in the x-ray, ultraviolet, visible, infrared, near infrared, terahertz, microwave, or radio frequency spectrum. In an embodiment, the energy-emitting component 104 includes a patterned energy-emitting source. In an embodiment, the energy-emitting component 104 includes a patterned light-emitting source.

In an embodiment, the energy-emitting component 104 concurrently or sequentially interrogates multiple focal volumes with the spatially-patterned pulsed multiplexed electromagnetic energy stimulus. In an embodiment, the energy-emitting component 104 concurrently or sequentially interrogates multiple focal volumes with a spatially-patterned, multifocal depth, electromagnetic energy stimulus.

In an embodiment, the energy-emitting component 104 delivers an electromagnetic energy stimulus having at least a first peak emission wavelength and a second peak emission wavelength different from the first peak emission wavelength. In an embodiment, the energy-emitting component 104 includes at least one of a first energy emitter and at least one of a second energy emitter, the at least one second energy emitter having a peak emission wavelength different from the at least one first energy emitter. In an embodiment, the energy-emitting component 104 concurrently or sequentially delivers a fast pulsed electromagnetic energy stimulus and a second pulse electromagnetic energy stimulus, the second pulsed energy stimulus having at least one of a pulse duration, a pulse frequency, a pulse intensity, a pulse ratio, or a pulse repetition rate different from the first pulsed electromagnetic energy stimulus. In an embodiment, the energy-emitting component 104 concurrently or sequentially delivers a first pulsed electromagnetic energy stimulus and a second pulse electromagnetic energy stimulus, the second pulsed electromagnetic energy stimulus baying a focal depth different from the first pulsed electromagnetic energy stimulus. In an embodiment, the energy-emitting component 104 concurrently or sequentially delivers a first pulsed electromagnetic energy stimulus and a second pulse electromagnetic energy stimulus, the second pulsed electromagnetic energy stimulus having a resolution different from the first pulsed electromagnetic energy stimulus. In an embodiment, at least a portion of the energy-emitting component. 104 is configured for removable attachment to a biological surface of a biological subject.

In an embodiment, the energy-emitting component 104 is configured to deliver a spatially-focused electromagnetic energy stimulus.

In an embodiment, the energy-emitting component 104 includes to lens array configured to deliver a spaced-apart energy stimuli having at least a first region and at least a second region, the second region having a focal depth different from the first region. In an embodiment, the second region has a peak emission wavelength different from the first region. In an embodiment, the second region has a peak irradiance different from the first region. In cm embodiment, the second region has at least one of an intensity, frequency, pulse intensity, pulse duration, pulse ratio, and pulse repetition rate different from an intensity, frequency, pulse intensity, pulse duration, pulse ratio, and pulse repetition rate of the first region. In an embodiment, the energy-emitting component 104 includes one or more orthogonal (or crossed) polarizers. In an embodiment, the sensor component 440 includes one or more orthogonal (or crossed) polarizers.

In an embodiment, the energy-emitting component 104 includes a plurality of selectively-actuatable electromagnetic energy waveguides that direct an emitted spatially-patterned pulsed multiplexed electromagnetic, energy stimulus to one or more regions of the at least one focal volume, in an embodiment, the energy-emitting component 104 includes a dark field electromagnetic energy emitting component to deliver a multi-mode dark-field interrogation stimulus to at least one blood vessel.

Referring to FIG. 1B, in an embodiment, the energy-emitting component 104 provides an illumination pattern 200 comprising at least a first region 202 and a second region 204. In an embodiment, the second region 204 of the illumination pattern 200 comprises at least one of an illumination intensity ($I_n$), an energy-emitting pattern, a peak emission wavelength ($\lambda_n$), an ON-pulse duration ($D_{(ON)}$), an OFF-pulse duration ($D_{(OFF)}$), or a pulse frequency ($v_n$) different from the first region 202. The energy-emitting component 104 can be configured to provide a spatially patterned electromagnetic energy stimulus having a peak emission wavelength in at least one of an x-ray, an ultraviolet, a visible, an infrared, a near infrared, a terahertz, microwave, or a radio frequency spectrum, or combinations thereof, to at least a portion of tissue proximate an monitor of treatment device 102. In an embodiment, the energy-emitting component 104 provides a spatially patterned optical energy stimulus. In an embodiment, the monitor or treatment device 102 includes, among other things, a patterned-light emitting source. In an embodiment, the patterned-light emitting source provides a spatially patterned energy stimulus to one or more region of a biological subject.

With continued reference to FIG. 1A, in an embodiment, the system 100 includes, among other things, circuitry 108 configured to detect (e.g. assess, calculate, evaluate, determine, gauge, measure, monitor, quantify, resolve, sense, or the like) a nonlinear optical response (e.g., a nonlinear multi-harmonic response, nonlinear multi-harmonic response energy associated with hemozoin nanoparticles within the at least one focal volume interrogated by an electromagnetic energy stimulus, or the like). In an embodiment, circuitry includes one or more components operably coupled (e.g., communicatively coupled, electromagnetically, magnetically, ultrasonically, optically, inductively, electrically capacitively coupleable, or the like) to each other. In an embodiment, circuitry includes one or more remotely located components. In an embodiment, remotely located components can be operably coupled via wireless communication. In an embodiment, remotely located components can be operably coupled via one or more receivers, transmitters, transceivers, or the like.

In an embodiment, circuitry includes, among other things, one or more computing devices 402 such as a processor (e.g., a microprocessor) 404, a central processing unit (CPU) 406, a digital signal processor (DSP) 408, an application-specific integrated circuit (ASIC) 410, a field programmable gate array (FPGA) 412, or the like, or any combinations thereof, and may include, discrete digital or analog circuit elements or electronics, or combinations thereof, in an embodiment, circuitry includes, among, other things, one or more field programmable gate arrays 412 having a plurality of programmable logic, components. In an embodiment, circuitry includes, among other things, one or more of an application specific integrated circuits having a plurality of predefined logic components. In an embodiment, at least one computing device 402 is operably coupled to one or energy-emitting components 104. In an embodiment, circuitry includes one or more computing devices 402 configured to concurrently or sequentially operate multiple energy-emitting components 104. In an embodiment, one or more computing devices 402 are configured to automatically control at least one waveform characteristic (e.g., intensity, frequency, pulse intensity, pulse duration, pulse ratio, pulse repetition rate, or the like) associated with the delivery of one or more energy stimuli. For example, pulsed waves may be characterized by the fraction of time the enemy stimulus is present over one pulse period. This fraction is called the duty cycle and is calculated by dividing the pulse time ON by the total time of a pulse period (e.g., time ON plus time OFF). In an embodiment, a pulse generator 403 may be configured to electronically generate pulsed periods and non-pulsed (or inactive) periods. In an embodiment, circuitry includes a computing device 402 operably coupled to the energy-emitting component 104, the computing device configured to control at least one parameter associated with a delivery of the spatially-patterned pulsed multiplexed electromagnetic energy stimulus.

In an embodiment, the computing device 402 is configured to control at least one of a delivery regimen, a spaced-apart delivery pattern, a spatial modulation, a temporal modulation, a magnitude, a spatial-pattern configuration, or a spatial distribution associated with the delivery of the spatially-patterned multiplexed electromagnetic energy stimulus. In an embodiment, the computing device 402 includes one or more processors 404 configured to control one or more parameter associated with one or more of a spatial illumination modulation, a spatial illumination intensity, or a spatial illumination delivery pattern associated with a delivery of the spatially-patterned pulsed multiplexed electromagnetic energy stimulus. In an embodiment, the computing device 402 includes one or more processors 404 configured to control one or more parameters associated a pulse frequency, a pulse intensity, a pulse ratio, or a pulse repetition rate associated with a delivery of the spatially-patterned pulsed multiplexed electromagnetic energy stimulus. In an embodiment, the computing device 402 includes one or more processors 404 configured to control one or more parameters associated a focal depth distribution associated with a delivery of the spatially-patterned pulsed multiplexed electromagnetic energy stimulus. In an embodiment, the computing device 402 includes one or more processors 404 operably coupled to the energy-emitting component and configured to control a spatial distribution of the spatially-patterned pulsed multiplexed electromagnetic energy stimulus. In an embodiment, the system 100 includes at least one processor 404 operable to cause a storing of information associated with magnetically inducing at least one of an oscillation, translation, and rotation of hemozoin nanoparticles in a biological tissue. In an embodiment, the system 100 at least one processor 404 operable to cause a storing of information associated with comparing a nonlinear multi harmonic response information to reference hemozoin response information on one or more computer-readable storage media.

In an embodiment, the computing device 402 includes one or more processors 404 for generating a control signal associated with actively controlling at least one of a duty cycle, a pulse train frequency, and pulse repetition rate associated with a magnetic field applied to the biological sample. In an embodiment, the computing device 402 includes one or more processors 404 for generating a control signal associated with actively controlling a magnetic field orientation. In an embodiment, the computing device 402 includes one or more processors 404 for generating a control signal associated with actively controlling a magnetic field strength. In an embodiment, the computing device 402 includes one or more processors 404 for generating a control signal associated with actively controlling a magnetic field spatial distribution. In an embodiment, the computing device 402 includes one or more processors 404 for generating a control signal associated with actively controlling a magnetic field temporal pattern. In an embodiment, the computing device 402 includes one or more processors 404 for generating a control signal associated with actively controlling a magnetic field ON duration. In an embodiment, the computing device 402 includes one or more processors 404 for generating a control signal associated with actively controlling a polarization of a generated magnetic field.

In an embodiment, the computing device 402 is configured to actuate the actively-controllable magnetic field generator in response to a comparison of a detected nonlinear multi-harmonic response profile to one or more reference hemozoin nonlinear response profiles. In an embodiment, the computing device 402 is configured to change at least one of a magnetic field ON duration, a magnetic field strength, a magnetic field frequency, or a magnetic field in response to the sensor's detection of a nonlinear multi-harmonic response profile associated with hemozoin nanoparticles in the biological sample. In an embodiment, the computing device 402 is configured to change a magnetic field spatial distribution pattern in response to the sensor's detection of a nonlinear multi-harmonic response profile associated with hemozoin nanoparticles in the biological sample, in an embodiment, the computing device 402 is configured to change a magnetic field temporal pattern in response to the sensor's detection of a nonlinear multi-harmonic response profile associated with hemozoin nanoparticles in the biological sample.

In an embodiment, circuitry includes, among other things, one or more memories 414 that, for example, store instructions or data, for example, volatile memory (e.g., Random Access Memory (RAM) 416, Dynamic Random Access Memory (DRAM), or the like), non-volatile memory (e.g., Read-Only Memory (ROM) 418, Electrically Erasable Programmable Read-Only Memory (EEPROM), Compact Disc Read-Only Memory (CD-ROM), or the like), persistent memory, or the like. Further non-limiting examples of one or more memories 414 include Erasable Programmable Read-Only Memory (EPROM), flash memory, or the like. The one or more memories 414 can be coupled to, for example, one or more computing devices 402 by one or more instruction, data, or power buses 420.

In an embodiment, circuitry includes, among other things, one or more databases 422. In an embodiment, a database 422 includes at least one of reference hemozoin spectral response information, reference hemozoin nonlinear optical response information, heuristically determined parameters associated with at least one in vivo or in vitro determined metric. In an embodiment, a database 422 includes at least one of absorption coefficient data, extinction coefficient data, scattering coefficient data, or the like. In an embodiment, a database 422 includes at least one of stored reference data such as infectious agent marker data, or the like. In a embodiment, a database 422 includes reference object information, in an embodiment, a database 422 includes at least one of erythrocyte graph information, malaria-infected erythrocyte graph information, or hemozoin graph information.

In an embodiment, a database 422 includes information associated with a disease state of a biological subject. In an embodiment, a database 422 includes measurement data. In an embodiment, a database 422 includes at least one of cryptographic, protocol information, regulatory compliance protocol information (e.g., FDA regulatory compliance protocol information, or the like), regulatory use protocol information, authentication protocol information, authorization protocol information, delivery regimen protocol information, activation protocol information, encryption protocol information, decryption protocol information, treatment protocol information, or the like. In an embodiment, a database 422 includes at least one of electromagnetic energy stimulus control delivery information, electromagnetic energy emitter control information, power control information, or the like.

In an embodiment, the system 100 is configured to compare an input associated with at least one characteristic associated with a biological subject to a database 422 of stored reference values, and to generate a response based in part on the comparison. In an embodiment, the system 100 is configured to compare an input associated with at least one characteristic associated the presence of hemozoin to a database 422 of stored reference values, and to generate a response used in part on the comparison.

In an embodiment, the system 100 includes, among other things, circuitry 108 configured to detect a nonlinear multi-harmonic spectral response resulting from interrogating a biological sample suspected of having hemozoin with an electromagnetic energy stimulus.

The behavior of electric fields, magnetic fields, charge density, and current density can be described, for example, by Maxwell's equations. See e.g., Saleh et al., *Fundamentals of Photonics*, pp. 152-170 ($2^{nd}$ Edition; 2007). Nonlinear optical phenomena include, among other things, those interactions of electromagnetic radiation with matter where the response of the matter (e.g., polarization, power absorption, or the like) is not linearly proportional (i.e., the amount of the response does not scale linearly) to the variables describing the electromagnetic radiation (e.g., irradiance, electric field strength, energy flux, fundamental wavelength, fundamental frequency, or the like). In an embodiment, the energy-emitting component 104 delivers an electromagnetic energy stimulus to one or more focal volumes suspected of containing hemozoin. Depending on the character and duration of the electromagnetic energy, the interaction of the electromagnetic stimulus with hemozoin within one or more focal volumes results in the generation of a nonlinear optical response that is detected via, for example, scattered radiation.

Nonlinear optical phenomena include, among other things, second harmonic generation (generation of light with a doubled frequency; one-half the wavelength of a fundamental wavelength emitted by an electromagnetic energy source), third harmonic generation (generation of light with a tripled frequency; one-third the wavelength of a fundamental wavelength emitted by an electromagnetic energy source), fourth harmonic generation, difference frequency generation, high harmonic generation, optical parametric amplification, optical parametric generation, optical parametric oscillation, optical rectification, spontaneous parametric down conversion, sum frequency generation, or the like. Further non-limiting examples of nonlinear optical phenomena include Brillouin scattering, multiple photo-ionization, optical Kerr effect, two-photon absorption, or the like.

The polarization density relationship describing the interaction of electromagnetic radiation with matter can be approximated (for sufficiently weak fields, assuming no permanent dipole moments are present) by the following sum of linear and nonlinear parts (see e.g., Saleh et al., *Fundamentals of Photonics*, pp. 871-935 (2$^{nd}$ Edition; 2007):

$$P_i(E) = (\epsilon_0 \chi_{ij}^{(1)} E_j + 2\chi_{ijk}^{(2)} E_j E_k + 4\chi_{ijkl}^{(3)} E_j E_k E_l + \ldots) \quad (eq. 1)$$

where, $\epsilon_0 \chi_{ij}^{(1)} E_j$ describes the linear first order optical phenomena including absorption and refraction;

$2\chi_{ijk}^{(2)} E_j E_k$ describes the second order nonlinear phenomena including electro-optic Rectification, Pockets electro-optic effect, and second-harmonic generation (e.g., frequency doubling); and $4\chi_{ijkl}^{(3)} E_j E_k E_l$ describes the third order nonlinear phenomena including electric field-induced optical rectification, four-wave mixing, intensity-dependent refractive index, quadratic Kerr effect, self-focusing, and third-harmonic generation (e.g., frequency tripling).

In an embodiment, the circuitry 108 configured to detect the nonlinear multi-harmonic response energy includes a sensor component 440 including one or more sensors. In an embodiment, the sensor component 440 is configured to detect a nonlinear multi-harmonic response profile associated with hemozoin nanoparticles interrogated by an electromagnetic energy stimulus, and configured to compare the detected nonlinear multi-harmonic response profile to one or more reference hemozoin nonlinear response profiles. In an embodiment, the reference hemozoin response profile includes one or more heuristically determined parameters associated with at least one in vivo or in vitro determined metric. In an embodiment, the one or more heuristically determined parameters include at least one of a threshold level or a target parameter. In an embodiment, the one or more heuristically determined parameters include threshold information.

In an embodiment, the sensor component 440 includes an optical energy sensor component configured to detect scattered optical energy from the plurality of hemozoin nanoparticles interrogated by the multi-mode dark-field interrogation stimulus in the presence of the magnetic field.

In an embodiment, the sensor component 440 includes an electromagnetic energy sensor component configured to detect, via a dark-field detection configuration, response energy associated with hemozoin nanoparticles interrogated by the multi-mode dark-field stimulus in the presence of the first electromagnetic energy stimulus, in an embodiment, the system 100 includes, among other things, circuitry 110 configured to generate at least one of a multi-mode dark-field interrogation stimulus or a multi-mode Rheinberg Interrogation stimulus.

In practice, a dark-field detection configuration includes blocking out of central electromagnetic energy rays (via, for example, a dark-field stop or an opaque object) along, an optical axis at an objective lens assembly 114, which ordinarily pass through and around a sample. Blocking the central electromagnetic energy rays allows only those oblique, rays originating at large angles (i.e., only light scattered by the biological sample within the focal volume) to reach the detector. In an embodiment, the dark-field detection configuration includes a compound microscope assembly including a condenser system enabling electromagnetic energy rays emerging from a focal region in all azimuths to form an inverted hollow cone of illumination having an apex centered in the specimen plane. Dark-field illumination detection techniques can be further enhanced in contrast and selectivity by adding polarizers (e.g., orthogonal (or crossed) polarizers, etc.) to the illuminator and detector. Cross polarization limits detection to scattering events that depolarize the illumination, greatly reducing false positives and unwanted signal from healthy tissue. This is relevant for both imaging and spectroscopic, in viva and in vitro system, devices, and methods.

In an embodiment, the sensor component 440 includes an electromagnetic energy sensor component configured to detect, via a Rheinberg detection configuration, response energy associated with hemozoin nanoparticles interrogated by the multi-mode dark-field stimulus in the presence of the first electromagnetic energy stimulus. In practice, a Rheinberg detection configuration resembles a dark-field detection configuration, but rather that using a dark-field stop, an opaque object, etc., along an optical axis; the Rheinberg detection configuration includes a Rheinberg filter of at least two different colors. In an embodiment, the central area, were the dark-field stop would typically reside, is one color (e.g., green) and the outer ring (annulus) a contrasting color (e.g., red). Unmodified light (light that does not impinge on the sample) fills the background with uniform light the color of the central circle, while modified light (light that impinges on the sample and is refracted, scattered, etc.,) would have the color of the outer annulus.

In an embodiment, the electromagnetic energy sensor component includes at least one Rheinberg filter, in an embodiment, the electromagnetic energy sensor component is configured to detect scatter energy associated with hemozoin nanoparticles interrogated by the multi-mode dark-field stimulus in the presence of a first electromagnetic energy stimulus or a second electromagnetic energy stimulus, in an embodiment, the electromagnetic energy sensor component includes at least one spectrometer. In an embodiment, the electromagnetic energy sensor component is configured to detect a spectral response associated with hemozoin nanoparticles interrogated by the multi mode dark-field stimulus in the presence of the first electromagnetic energy stimulus or the second electromagnetic energy stimulus.

In an embodiment, the electromagnetic energy sensor component is configured to detect scatter energy associated with hemozoin nanoparticles interrogated by the multi-mode dark-field stimulus in the presence of the first electromagnetic energy stimulus or the second electromagnetic energy stimulus.

In an embodiment, the system 100 includes, among other things, a sensor component 440 including at least one sensor 442 configured to detect nonlinear multi harmonic response energy associated with hemozoin nanoparticles within at least one focal volume of a biological tissue interrogated by an electromagnetic energy stimulus, in an embodiment, the system 100 includes, among other things, a computing device 402 operably coupled to at least one sensor of the sensor component 440 and the energy-emitting component 104, the computing device 402 configured to provide a control signal to an energy-emitting component.

In an embodiment, the system 100 includes, among other things, an energy-emitting component 104 configured to deliver an effective amount of a electromagnetic energy stimulus to elicit a nonlinear optical response from hemozoin nanoparticles within the biological tissue, the elicited nonlinear response of a character and for a duration sufficient to modulate a biological activity of a malarial infectious agent within the biological tissue, in an embodiment, the elicited nonlinear response includes one or more peak emission wavelengths ranging, from about 175 nanometers to about 650 nanometers. In an embodiment, the elicited nonlinear response includes one or more peak emission wavelengths ranging from about 250 nanometers to about 270 nanometers, in an embodiment, the elicited nonlinear response includes a peak emission wavelengths of about 260 nanometers.

In an embodiment, the elicited nonlinear response is of a character and for a duration sufficient to induce programmed cell death of a plasmodium parasite that includes the hemozoin nanoparticles. Many eukaryotic cells, including, some unicellular organisms, undergo one or more forms of programmed cell death. Programmed cell death can be induced, either by a stimulus such as, for example, non-repairable damage to the cell, infection, starvation, exposure to ionizing radiation, heat or toxic chemicals, or by removal of a repressor agent initiation of programmed cell death in response to specific stimuli may represent to favorable adaptation by the organism and may confer advantage during an organisms life-cycle, in the case of plasmodium parasite, for example, programmed cell death of to subset of the parasite population could be a means for preventing early death of the infected host, providing the parasite sufficient time to develop and be transmitted to another vector or host (see, e.g. Deponte & Becker, *Trends Parasitol.*, 20:165-169, 2004, which is incorporated herein by reference). By contrast, necrosis is defined as uncontrolled cell death that results from extreme physical or chemical insult to the cell. Necrosis can be induced by mechanical damage, hypoxia, complement-mediated cell lysis, high temperature, and exposure to highly toxic agents. Necrosis is more likely to provoke an inflammatory response in the host as a result of catastrophic disruption of the cell.

Various types of programmed cell death have been described including, but not limited to apoptosis, autophagy, oncosis, pyroptosis and paraptosis. Apoptosis is characterized by a series of biochemical events leading to changes in cell morphology and ultimately cellular death. The characteristic changes in cell morphology associated with apoptosis include but not limited to blebbing and fragmentation of the nucleus, formation of apoptotic bodies, changes to the cell membrane such as loss of membrane asymmetry and attachment, cell shrinkage and rounding, changes in cytoplasm density, nuclear fragmentation, chromatin condensation, chromosomal DNA fragmentation, oxidative stress, the release of proteins (e.g., cytochrome c) from the mitochondria into the cytosol, the selective cleavage of proteins by proteases (especially caspases), and the activity of the proteases themselves, in contrast, autophagy is a catabolic process involving the degradation of a cell's own components through the lysosomal machinery, characterized by the formation of large vacuoles which digest away the cellular organelles in a specific sequence prior to destruction of the nucleus. Oncosis is a regulated response to severe DNA damage leading to energy depletion, organelle swelling and cell membrane disruption. Pyroptosis is a pro-inflammatory cell death pathway induced by intracellular bacteria in phagocytic cells and differs from the anti-inflammatory pathways of apoptosis. Paraptosis is morphologically similar to necrosis with formation of cytoplasmic vacuoles and mitochondrial swelling, but requires new RNA and protein synthesis, consistent with a programmed biochemical event. See, e.g., Durand & Coetzer, *Bioinform. Biol. Insights* 2:101-117, 2008, which is incorporated herein by reference.

Programmed cell death akin to apoptosis has been observed in plasmodium parasites. For example, cultured ookinetes of *Plasmodium berghei* exhibit multiple markers for apoptosis-like programmed cell death including loss of mitochondrial membrane potential, nuclear chromatin condensation, DNA fragmentation, translocation of phosphatidylserine to the outer surface of the cell membrane and caspase-like activity (see, e.g., Arambage, et al., *Parasit. Vectors* 2:32, 2009, which is incorporated herein by reference). While the genomes of plasmodium parasites appear to lack homologs of the mammalian caspases, other proteases including metacaspases and calpain may play a role in mediating programmed cell death in plasmodium parasites (see, e.g., Wu et al., *Genome Res.*, 13:601-616, 2003; Chat et al., *Mol. Biochem. Parasitol.*, 153:41-47, 2007, which are incorporated herein by reference).

Programmed cell death akin to autophagy has also been observed in plasmodium parasites. For example, treatment of blood stage *Plasmodium falciparum* with S-nitroso-N-acetyl-penicillamine (SNAP), staurosporine, and chloroquine inhibits parasitemia and induces autophagy-like morphology with vacuolization of cellular components (see, e.g., Totino, et al., *Exp. Parasitol.*, 118:478-486, 2008, which is incorporated herein by reference).

Programmed cell death can be induced by heat-shock or acute exposure to temperatures above the normal physiological range of the organism. Hyperthermia therapy between 40° C. and 60° C. can result in disordered cellular metabolism and membrane function and in many instances, cell death. In general, at temperatures below 60° C., hyperthermia is more likely to induce programmed cell death without substantially inducing necrosis. At temperatures greater than about 60° C., the likelihood of inducing coagulation necrosis of cells and tissue increases. Relatively small increases in temperature, e.g., 3° C., above the normal functioning temperature of a cell can cause programmed cell death. For example, temperatures ranging from 40° C. to 47° C. can induce cell death in a reproducible time and temperature dependent manner in cells normally functioning at 37° C. Elevating the temperature of a mammalian cell, for example, to 43° C. can cause changes in cellular protein expression and increased programmed cell death. See, e.g., Somwaru, et al., *J. Androl.* 25:506-513, 2004; Stankiewicz, et al., *J. Biol. Chem.* 280:38729-38739, 2005; Sodja, et al., *J. Cell Sci.* 111:2305-2313, 1998; Setroikromo, et al., *Cell Stress Chaperones* 12:320-330, 2007; Dubinsky, et al., *AJR* 190:191-199, 2008; Lepock. *Int. J. Hyperthermia,* 19:252-266, 2003; Roti Roti *Int. J. Hyperthermia* 24:3-15, 2008; Fuchs, et al., "The Laser's Position in Medicine" pp 187-198 in *Applied Laser Medicine.* Ed. Hans-Peter Berlien, Gerhard J. Muller, Springer-Verlag New York, LLC, 2003; which are all incorporated herein by reference.

*Plasmodium* parasites are also susceptible to programmed cell death in response to hyperthermia therapy. For example, established isolates of *Plasmodium falciparum* as well as wild isolates derived from patients with malaria fail to grow at a culture temperature of 40° C., with schizonts exhibiting chromatin condensation (pyknosis) and hyposegmentation (see Kwiatkowski, *J. Exp. Med.* 169:357.361, 1989, which is incorporated herein by reference). It is suggested that the marked inhibition of *Plasmodium falciparum* growth at elevated temperature is due to disruption of the latter half of the asexual erythrocytic cycle, with developing schizonts particularly vulnerable to heat-shock. Treatment of erythrocyte stage *Plasmodium falciparum* at 40° C. also appears to induce cytoplasmic vacuolization and disruption of the parasite's food vacuole (see, e.g., Porter et al., *J. Parasitol.* 94:473-480, 2008). Exposure of *Plasmodium falciparum* to a temperature of 41° C. for as little as two minutes causes relative decreases in the number of parasites in the ring stage, trophozoite stage, and schizont stage measured 48 hours later by 20%, 70%, and 100%, respectively (see, e.g., Joshi et al., *FEBS* 312:91-94, 1992, which is incorporated herein by reference). Heating erythrocyte stage *Plasmodium falciparum* at 41° C. for 2, 8, and 16 hours reduces survival of the parasites by 23%, 66%, and 100%, respectively (see Oakley et al., *Infection Immunity* 75:2012-2025, 2007, which is incorporated herein by reference). The reduction in survival under these heat-shock conditions is accompanied by the appearance of "crisis forms" of the parasite and a time depend increase in positive terminal deoxynucleotidyltransferase-mediated dUTP-biotin nick end labeling (TUNEL) activity, indicators of programmed cell death. The response to heat-shock is also accompanied by changes in plasmodium parasite gene and protein expression suggesting that exposure to elevated temperature, e.g., 41° C., induces an organized signaling pathway involved in promoting programmed cell death as a response to elevated temperature. For example, mRNA and protein corresponding to the *Plasmodium falciparum* heat shock protein 70 (PfHSP-70) are elevated 7.42 fold and 3.7 fold, respectively in response to heat-shock at 41° C. A number of other parasite proteins are up or down regulated in response to hyperthermia including other stress proteins, DNA repair/replication proteins, histones, RNA processing proteins, secretion and trafficking proteins, and various serine/threonine protein kinases (see Oakley et al., *Infection Immunity* 75:2012-2025, 2007, which is incorporated herein by reference).

In some instances, programmed cell death in plasmodium parasites may be induced by exposure to one or more drugs. For example, the anti-malarial drug chloroquine concentrates in the plasmodium parasite food vacuole where it caps hemozoin molecules to prevent further biocrystallization of heme, leading to accumulation of heme in the parasite. Chloroquine complexed to heme is highly toxic to the plasmodium parasite and disrupts membrane function, causing cell lysis and ultimately parasite cell autodigestion. See, e.g., Orjih et al., *Science*, 214:667-669, 1981, which is incorporated herein by reference. In another example, treatment of erythrocyte stage *Plasmodium falciparum* with atovaquone reduces the number of detectable infected erythrocytes 2- to 3-fold with a concomitant loss in parasite mitochondrial membrane potential, a marker of programmed cell death (see Nyajeruga et al., *Microbes Infect.* 8:1560-1568, 2006, which is incorporated herein by reference). Treatment of erythrocyte stage *Plasmodium falciparum* with S-nitroso-N-acetyl-penicillamine (SNAP) induces abnormal parasite forms, "crisis forms," and DNA degradation, also markers of programmed cell death. The inhibition of plasmodium parasite growth and induction of plasmodium parasite death by various anti-malarial drugs may be accompanied by changes in the plasmodium parasite proteosome. For example, treatment of *Plasmodium falciparum* with artemisinin and chloroquine results in upregulation of 41 and 38 parasite proteins respectively (see, e.g., Prieto, et al., *PLoS ONE,* 3:e4098, 2008, which is incorporated herein by reference). In an embodiment, the systems, devices, or methods described herein can be used sequentially, or concurrently with anti-malarial drugs to, for example, induce programmed cell death in *Plasmodium falciparum.*

In an embodiment, the elicited nonlinear response is of a character and for a duration sufficient to cause a cellular stress, a cellular structural change (e.g., chromatin condescension, cell shrinkage, deoxyribonucleic acid fragmentation, etc.), activation of a caspases gene, or the like, associated with the induction of programmed cell death (e.g., apoptosis, death of a cell mediated by an intracellular program, or the like) of a cell, a host cell, a malarial infectious agent, or the like.

In an embodiment, the elicited nonlinear response is of a character and for a duration sufficient to generate antimicrobial energy. In an embodiment, nonlinear harmonic generation of ultraviolet radiation by hemozoin in a biological tissue (e.g., in vivo hemozoin) can be used to irradiate malarial parasites with antimicrobial energy. The incident electromagnetic energy stimulus can be focused and pulsed in order to increase the intensity to levels sufficient for effective harmonic generation. In an embodiment, the time-duty-cycle can be at a low enough level so that linear energy deposition of the incident light does not damage other tissues. The treatment can occur in vivo (e.g., transdermal, in-eye, via fiber optic, etc.) or ex vivo (e.g., blood flow through external device). In an embodiment, the electromagnetic energy stimulus includes a narrow-bandwidth light to increase the spectral brightness and hence the harmonic generation efficiency. In an embodiment, the electromagnetic energy is delivered via multiple pulses to increase total output. In an embodiment, phase-matched pulse-stacking is used to combine multiple beams/pulses at target site.

In an embodiment, the elicited nonlinear response is of a character and for a duration sufficient to generate a sterilizing energy stimulus having one or more peak emission wavelengths in the ultraviolet range. In an embodiment, the elicited nonlinear response is of a character and for a duration sufficient to induce programmed cell death of a host cell carrying the malarial infectious agent.

In an embodiment, the circuitry 108 to detect the nonlinear multi-harmonic response energy includes one or more electromagnetic sensors 442. Non-limiting examples of electromagnetic sensors 442 includes electromagnetic devices having a detectable response to received or absorbed electromagnetic energy. Electromagnetic sensors can include antennas (e.g., wire/loop antennas, horn antennas, reflector antennas, patch antennas, phased array antennas, or the like) solid-state photodetectors (e.g., photodiodes, charged-coupled devices, and photoresistors), vacuum photodetectors (e.g., phototubes and photomultipliers) chemical photodetectors (e.g., photographic emulsions), cryogenic photodetectors (e.g., bolometers), photoluminescent detectors (e.g., phosphor powders or fluorescent dyes/markers), micro-electro-mechanical systems (MEMS) detectors (e.g., microcantilever arrays with electromagnetically responsive materials or elements) or any other devices operable to detect and/or transduce electromagnetic energy.

In an embodiment, the circuitry 108 to detect the nonlinear multi-harmonic response energy includes one or more sensors 442 to detect a nonlinear response profile of one or more hemozoin nanoparticles interrogated by an electromagnetic energy stimulus. Non-limiting examples of sensor 442 include charge-coupled devices, complementary metaloxide-semiconductor devices, photodiode image sensor devices, or whispering gallery mode micro cavity devices.

In an embodiment, the circuitry 108 to detect the nonlinear multi-harmonic response energy includes at least one of a time-integrating optical component, a linear time-integrating component, a nonlinear optical component, or a temporal auto-correlating component. In an embodiment, the circuitry 108 to detect the nonlinear multi-harmonic response energy includes one or more one-, two-, or three-dimensional photodiode arrays. In an embodiment, the circuitry 108 to detect the nonlinear multi-harmonic response energy includes one or more sensors 442 for detecting a nonlinear response profile of one or more hemozoin nanoparticles within the at least one focal volume. In an embodiment, the circuitry 108 to detect the nonlinear multi-harmonic response energy includes at least one charge-coupled device for detecting a nonlinear response profile of hemozoin nanoparticles within the at least one focal volume. In an embodiment, the circuitry 108 to detect the nonlinear multi-harmonic response energy includes at least one spectrometer configured to detect a nonlinear spectral response profile of hemozoin nanoparticles within the at least one focal volume. In an embodiment, the circuitry 108 to detect the nonlinear multi-harmonic response energy includes at least one ultraviolet-visible (UV-VIS) diode array detector for detecting a nonlinear response profile of hemozoin nanoparticles within the at least one focal volume. In an embodiment, the circuitry 108 to detect the nonlinear multi-harmonic response energy includes at least one high-sensitivity ultraviolet-visible (UV-VIS) diode array detector for detecting a nonlinear response profile of hemozoin nanoparticles within the at least one focal volume. In an embodiment, the circuitry 108 to detect the nonlinear multi-harmonic response energy includes circuitry configured to detect a transcutaneously emitted multi-harmonic photonic response (e.g., a nonlinear optical response to an electromagnetic energy stimulus).

In an embodiment, the circuitry 108 to detect the nonlinear multi-harmonic response energy includes a multiplet of sensors 442 operable at a corresponding multiplet of wavelengths or wavelength bands, i.e., a first sensor operable at a first wavelength/wavelength band, a second sensor operable at a second wavelength/wavelength band, etc. In an embodiment, the circuitry 108 to detect the nonlinear multi-harmonic response energy includes a focal plane array of sensors 442 or sensor multiplets (e.g., a Bayer or Foveon sensor).

In an embodiment, the circuitry 108 to detect the nonlinear multi-harmonic response energy includes a sensor component 440 to detect a nonlinear multi-harmonic response profile associated with hemozoin nanoparticles in a biological tissue within multiple focal volumes interrogated by a pulsed electromagnetic energy stimulus. In an embodiment, the circuitry 108 to detect the nonlinear multi-harmonic response energy includes at least one sensor 442 for detecting nonlinear multi-harmonic response energy associated with at least one of a second harmonic response, a third harmonic response, or a fourth harmonic response elicited by an electromagnetic energy stimulus (e.g., a pulsed electromagnetic energy stimulus, a spatially-patterned electromagnetic energy stimulus, a multiplexed electromagnetic energy stimulus, a spatially-patterned pulsed multiplexed electromagnetic energy stimulus, a temporally patterned electromagnetic energy stimulus, or the like).

In an embodiment, the circuitry 108 to detect the nonlinear multi-harmonic response energy includes an optical assembly 112 and at least one sensor 442 for collecting and detecting via an epi-collection mode at least one of a second harmonic response, a third harmonic response, or a fourth harmonic response elicited by the spatially-patterned pulsed multiplexed electromagnetic energy stimulus. The optical assembly 112 can take a variety of forms and configurations. In an embodiment, the optical assembly 112 includes one or more lenses, optical elements (e.g., a beamsplitter and lens), diffractive elements (e.g. Fresnel lenses), filters, polarizers, or the like to guide and shape electromagnetic radiation from a source (e.g., an energy-emitting component 104, a nonlinear optical response, or the like). In an embodiment, Dark-field illumination detection techniques can be further enhanced in contrast and selectivity by adding orthogonal (or crossed) polarizers to the illuminator and detector. Cross polarization limits detection to scattering events that depolarize the illumination, greatly reducing false positives and unwanted signal from healthy tissue. This is relevant for both imaging and spectroscopic, in vivo and in vitro system, devices, and methods.

Non-limiting examples of lenses include cylindrical graded index (GRIN) lenses, doublet or triplet lenses, that gather and shape electromagnetic radiation from a source (e.g., an energy-emitting component 104, a nonlinear optical response, or the like). Where the electromagnetic radiation source includes optical fibers that feed one or more lenses, the lenses are optionally bonded to or integral with the fibers.

In an embodiment, the optical assembly 112 includes one or more of polarization sensitive materials, chromatic correction, or other optical techniques for controlling the shape, phase, polarization, or other characteristics of the electromagnetic radiation. In an embodiment, the optical assembly 112, includes one or more polarizers, color filters, exit pupil expanders, chromatic correction elements, eye-tracking elements, and background masks may be incorporated for certain application as appropriate. In an embodiment, the optical assembly 112 includes at least one Rheinberg filter. In an embodiment, the optical assembly 112 includes an objective lens assembly 114 having a selectively controllable numerical aperture ranging from about 0.5 to about 1.4. In an embodiment, the circuitry 108 configured to detect the nonlinear multi-harmonic response energy includes a computing device 402 for actively controlling a numerical aperture of an objective lens assembly 114 having a selectively controllable numerical aperture ranging from about 0.5 to about 1.4. In an embodiment, the system 100 includes an objective lens assembly 114 having a numerical aperture ranging from about 0.5 to about 1.4.

In an embodiment, the optical assembly 112 receives a portion of scattered radiation in a dark field collection configuration. In an embodiment, the optical assembly 112 receives a portion of scattered radiation in a Rheinberg collection configuration. In an embodiment, the optical assembly 112 receives a portion of scattered radiation in an epi-collection configuration. In an embodiment, the circuitry 108 to detect the nonlinear multi-harmonic response energy includes circuitry configured to detect, in situ, nonlinear multi-harmonic response energy associated with hemozoin nanoparticles within the at least one focal volume interrogated by the spatially-patterned pulsed multiplexed electromagnetic energy stimulus.

In an embodiment, the system 100 includes, among other things, circuitry 116 to compare information associated with a detected nonlinear multi-harmonic response information to reference information configured as a data structure 424. In an embodiment, the system 100 includes, among other things, circuitry 116 configured to compare information associated with a detected nonlinear multi-harmonic response information to reference hemozoin response information configured as a data structure 424. In an embodiment, the data structure 424 includes one or more heuristics. In an embodiment, the one or more heuristics include a heuristic for determining a rate of change associated with at least one physical parameter associated with a biological fluid. In an embodiment, the one or more heuristics include a heuristic for determining the presence of hemozoin nanoparticles. In an embodiment, the one or more heuristics include a heuristic for determining the presence of an infectious agent. In an embodiment, the one or more heuristics include a heuristic for determining at least one dimension of an infected tissue region. In an embodiment, the one or more heuristics include a heuristic for determining a location of an infection. In an embodiment, the one or more heuristics include a heuristic for determining a rate of change associated with a biochemical marker within the one or more focal volumes.

In an embodiment, the one or more heuristics include a heuristic for determining a biochemical marker aggregation rate (e.g., a hemozoin aggregation rate, a hemozoin polymer aggregation rate, or the like). In an embodiment, the one or more heuristics include a heuristic for determining a type of biochemical marker. In an embodiment, the one or more heuristics include a heuristic for generating at least one of erythrocyte graph information, malaria-infected erythrocyte graph information, or hemozoin graph information.

In an embodiment, the one or more heuristics include a heuristic for generating at least one initial parameter. In an embodiment, the one or more heuristics include a heuristic for forming an initial parameter set from one or more initial parameters. In an embodiment, the one or more heuristics include a heuristic for generating at least one initial parameter, and for forming an initial parameter set from the at least one initial parameter. In an embodiment, the one or more heuristics include at least one pattern classification and regression protocol.

In an embodiment, at least one data structure 424 includes information associated with at least one parameter associated with hemozoin nonlinear optical phenomena spectral information. For example, in an embodiment, a data structure 424 includes information associated with at least one parameter associated with at least one of hemozoin second harmonic response spectral information, hemozoin third harmonic response spectral information, or hemozoin fourth harmonic response spectral information. In an embodiment, a data structure 424 includes reference object information. In an embodiment, a data structure 424 includes at least one of erythrocyte graph information, malaria-infected erythrocyte graph information, or hemozoin graph information.

In an embodiment, the system 100 includes, among other things, one or more computer-readable media drives 426, interface sockets, Universal Serial Bus (USB) ports, memory card slots, or the like, and one or more input/output components 428 such as, for example, a graphical user interface 430, a display, a keyboard 432, a keypad, a trackball, a joystick, a touch-screen, a mouse, a switch, a dial, or the like, and any other peripheral device. In an embodiment, the system 100 includes one or more user input/output components 428 that operably coupled to at least one computing device 402 to control (electrical, electromechanical, software-implemented, firmware-implemented, or other control, or combinations thereof) at least one parameter associated with the energy delivery associated with the one or more energy-emitting components 104. In an embodiment, the system 100 includes among other things, one or more modules optionally operable for communication with one or more input/output components 428 that are configured to relay user output and/or input. In an embodiment, a module includes one or more instances of electrical, electromechanical, software-implemented, firmware-implemented, or other control devices. Such device include one or more instances of memory 414, computing devices 402, ports, valves 132, antennas, power, or other supplies; logic modules or other signaling modules; gauges or other such active or passive detection components; or piezoelectric transducers, shape memory elements, micro-electro-mechanical system (MEMS) elements, or other actuators.

The computer-readable media drive 426 or memory slot may be configured to accept signal-bearing medium (e.g., computer-readable memory media, computer-readable recording media, or the like). In an embodiment, a program for causing the system 100 to execute any of the disclosed methods can be stored on, for example, a computer-readable recording medium (CRMM) 434, a signal-bearing medium, or the like. Non-limiting examples of signal-bearing media include a recordable type medium such as a magnetic tape, floppy disk, a hard disk drive, a Compact Disc (CD), a Digital Video Disk (DVD), Blu-Ray Disc, a digital tape, a computer memory, or the like, as well as transmission type medium such as a digital and/or an analog communication medium (e.g., a fiber optic cable, a waveguide, a wired communications link, a wireless communication link (e.g., transmitter, receiver, transceiver, transmission logic, reception logic, etc.), etc.). Further non-limiting examples of signal-bearing media include, but are not limited to, DVD-ROM, DVD-RAM, DVD+RW, DVD-RW, DVD-R, DVD+R, CD-ROM, Super Audio CD, CD-R, CD+R, CD+RW, CD-RW, Video Compact Discs, Super Video Discs, flash memory, magnetic tape, magneto-optic disk, MINIDISC, non-volatile memory card, EEPROM, optical disk, optical storage, RAM, ROM, system memory, web server, or the like.

In an embodiment, the system 100 includes signal-bearing media in the form of one or more logic devices (e.g., programmable logic devices, complex programmable logic device, field-programmable gate arrays, application specific integrated circuits, or the like) comprising, for example, a data structure 424 including one or more look-up tables. In an embodiment, the system 100 includes, among other things, signal-bearing media having reference hemozoin nonlinear response information configured as a data structure 424. In an embodiment, the data structure 424 includes at least one of malarial infection indication information, hemozoin spectral information, hemozoin optical response information, diseased state indication information, or diseased tissue indication information.

The system 100 can include among other things, one or more receivers 1206, transceivers 1208, transmitters 1210, or the like. In an embodiment, at least one of the one or more receivers 1206, transceivers 1208, or transmitters 1210 is wirelessly coupled to a computing device 402 that communicates with a control unit of the system 100 via wireless communication. In an embodiment, at least one receiver 1206 or transceiver 1208 is configured to acquire information associated with a set of targets, biomarkers, or the like for detection. In an embodiment, at least one receiver 1206 or transceiver 1208 is configured to acquire information associated with a set of physiological characteristic for detection. In an embodiment, at least one receiver 1206 or transceiver 1208 is configured to acquire information associated with one or more physiological characteristics for detection. In an embodiment, at least one receiver 1206 or transceiver 1208 is configured to acquire information associated with one or more hemozoin characteristics for detection.

In an embodiment, the system 100 includes at least one transceiver 1208 configured to report status information at a plurality of time intervals in response to the comparison. In an embodiment, the system 100 includes at least one transceiver 1208 configured to request reference hemozoin nonlinear response information in response to the comparison.

In an embodiment, the system 100 includes a transmitter configured to send comparison information associated with a comparison of detected nonlinear multi-harmonic response energy to the reference hemozoin response profile. In an embodiment, at least one of a receiver 1206 or a transceiver 1208 is configured to obtain information regarding a target detection set of one or more characteristics associated with the biological subject. In an embodiment, the system 100 includes at least one of a transmitter 1210, a receiver 1206, or a transceiver 1208 configured to acquire magnetization-induced nonlinear optical response information emitted by a biological sample. In an embodiment, the system 100 includes at least on transceiver 1208 configured to concurrently or sequentially transmit or receive information.

In an embodiment, the system 100 includes, among other things, circuitry 116 configured to compare information associated with a detected nonlinear multi-harmonic response energy to a reference hemozoin response profile. In an embodiment, the circuitry 116 for comparing information associated with the detected nonlinear multi-harmonic response energy to the reference hemozoin response profile includes one or more computer-readable memory media having a reference hemozoin response profile configured as a data structure 424, the reference hemozoin response profile including at least one of hemozoin second harmonic response spectral information, hemozoin third harmonic response spectral information, or hemozoin fourth harmonic response spectral information. In an embodiment, the reference hemozoin response profile includes reference nonlinear response information indicative of a hemozoin nanoparticle aggregation rate. In an embodiment, the reference hemozoin response profile includes reference nonlinear response information indicative of a presence of a hemoglobin metabolite including a heme polymer. In an embodiment, the reference hemozoin response profile includes reference hemozoin nanoparticle nonlinear susceptibility information.

In an embodiment, the circuitry 116 configured to compare the detected nonlinear multi-harmonic response energy to the reference hemozoin response profile includes one or more computer-readable memory media having a reference hemozoin response profile configured as a data structure 424, the reference hemozoin response profile including at least one of hemozoin nonlinear response information, hemozoin spectral information, or hemozoin nonlinear susceptibility information.

In an embodiment, the circuitry 116 configured to compare the detected nonlinear multi-harmonic response energy to the reference hemozoin response profile includes one or more computer-readable storage media including executable instructions stored thereon that, when executed on a computer, instruct a computing device 402 to (a) retrieving from storage one or more parameters associated with reference hemozoin nonlinear response information; and to (b) perform a comparison of a detected nonlinear multi-harmonic response profile to the retrieved one or more parameter. In an embodiment, the one or more computer-readable storage media further include executable instructions stored thereon that, when executed on a computer, instruct a computing device 402 to determine one or more of a presence, an absence, or a severity of malaria in response to the comparison.

In an embodiment, the circuitry 116 configured to compare the detected nonlinear multi-harmonic response energy to the reference hemozoin response profile includes a transmitter configured to send comparison information associated with a comparison of in situ detected nonlinear multi-harmonic response energy to the reference hemozoin response profile. In an embodiment, the circuitry 116 configured to compare the detected nonlinear multi-harmonic response energy to the reference hemozoin response profile includes a transceiver 1208 configured to receive a request to transmit at least one of hemozoin reference information. In situ detected nonlinear multi-harmonic response energy, and comparison information.

In an embodiment, the circuitry 116 configured to compare the detected nonlinear multi-harmonic response energy to the reference hemozoin response profile includes a transceiver 1208 configured to receive hemozoin filtering information. In an embodiment, the circuitry 116 configured to compare the detected nonlinear multi-harmonic response energy to the reference hemozoin response profile includes a transceiver 1208 configured to receive spatially-patterned pulsed multiplexed electromagnetic energy stimulus delivery parameter information. In an embodiment, the circuitry 116 configured to compare the detected nonlinear multi-harmonic response energy to the reference hemozoin response profile includes a transceiver 1208 configured to report status information at regular or irregular time intervals. In an embodiment, the circuitry 116 configured to compare the detected nonlinear multi-harmonic response energy to the reference hemozoin response profile includes circuitry configured to store paired and unpaired nonlinear multi-harmonic response data. In an embodiment, the circuitry 116 configured to compare the detected nonlinear multi-harmonic response energy to the reference hemozoin response profile includes at least one processor operable to cause a storing of information associated with comparing the nonlinear multi-harmonic response energy to the reference hemozoin response profile on one or more computer-readable storage media.

In an embodiment, the system 100 includes, among other things, circuitry 120 configured to wirelessly communicate comparison information associated with comparing detected nonlinear multi-harmonic response energy to the reference hemozoin response profile. In an embodiment, the system 100 includes, among other things, circuitry 122 configured to selectively tune at least one of a wavelength distribution of the spatially-patterned pulsed multiplexed electromagnetic energy stimulus or a wavelength distribution of a collected in situ nonlinear multi-harmonic response.

In an embodiment, the system 100 includes, among other things, circuitry 124 configured to generate a response based least in part on one or more comparisons between detected nonlinear multi-harmonic response energy and the reference hemozoin response profile. In an embodiment, the response includes at least one of a visual representation, an audio representation (e.g., an alarm, an audio waveform representation of a tissue region, or the like), a haptic representation, or a tactile representation (e.g., a tactile diagram, a tactile display, a tactile graph, a tactile interactive depiction, a tactile model (e.g., a multidimensional model of an infected tissue region, or the like), a tactile pattern (e.g., a refreshable Braille display), a tactile-audio display, a tactile-audio graph, or the like). In an embodiment, the response includes generating at least one of a visual, an audio, a haptic, or a tactile representation of at least one of biological sample spectral information, tissue spectral information, fat spectral information, muscle spectral information, bone spectral information, blood component spectral information, hemozoin spectral information or the like. In an embodiment, the response includes generating at least one of a probability that the biological sample is infected with malaria, or a confidence level associated with the determined probability that the biological sample is infected with malaria.

In an embodiment, the response includes generating at least one of a visual, an audio, a haptic, or a tactile representation of at least one physical or biochemical characteristic associated with a biological subject. In an embodiment, the response includes generating at least one of a visual, an audio, a haptic, or a tactile representation of at least one physical or biochemical characteristic associated with a parasitic infection, a disease state, or the like.

In an embodiment, the response includes initiating one or more treatment protocols. In an embodiment, the response including initiating one or more treatment protocols includes initiating at least one treatment regimen. In an embodiment, the response includes delivering an energy stimulus. In an embodiment, the response includes delivering an active agent. In an embodiment, the response includes concurrently or sequentially delivering an energy stimulus and an active agent. In an embodiment, the response includes at least one of a response signal, a control signal, a change to a treatment parameter, or the like.

In an embodiment, the response includes a change to a character of an electromagnetic energy stimulus. For example, in an embodiment, the response includes a change to at least one of a peak power, a peak irradiance, a focal spot size, a pulse width, a peak emission wavelength, or the like. In an embodiment, the response includes a change to at least one of an electromagnetic energy stimulus intensity, an electromagnetic energy stimulus frequency, an electromagnetic energy stimulus pulse frequency, an electromagnetic energy stimulus pulse ratio, an electromagnetic energy stimulus pulse intensity, an electromagnetic energy stimulus pulse duration time, an electromagnetic energy stimulus pulse repetition rate, or the like.

In an embodiment, the circuitry 124 configured to generate a response based least in part on one or more comparisons includes one or more receivers 1206, transmitters 1210, transceivers 1208, or the like. In an embodiment, the circuitry 124 configured to generate a response based least in part on one or more comparisons includes at least one of a transmitter 1210 or a transceiver 1208 configured to send comparison information associated with a comparison of detected nonlinear multi-harmonic response energy to the reference hemozoin response profile. In an embodiment, the circuitry 124 configured to generate a response based least in part on one or more comparisons includes at least one of a receiver 1206 or a transceiver 1208 configured to obtain reference hemozoin response profile information.

In an embodiment, the system 100 includes, among other things, circuitry 126 configured to cause the generation of a magnetic field. For example, in an embodiment, the circuitry 126 includes one or more conductive traces configured to generating a magnetic field in the presence of an applied potential. In an embodiment, the circuitry 126 configured to generate the magnetic field includes a radio frequency transmitter configured to generate a radio frequency signal. In an embodiment, the circuitry 126 configured to generate the magnetic field includes a radio frequency transmitter configured to generate a radio frequency signal of a character and for a duration sufficient to magnetically align, in vivo, a plurality of hemozoin nanoparticles. In an embodiment, the 126 circuitry configured to generate the magnetic field includes one or more coils configured to generate one or more radio frequency pulses.

In an embodiment, the system 100 includes, among other things, circuitry 128 generate a magnetic field stimulus. In an embodiment, the circuitry 128 includes a radio frequency transmitter configured to generate a radio frequency signal. In an embodiment, the circuitry 128 includes one or more conductive traces configured to generating a magnetic field in the presence of an applied potential. In an embodiment, the circuitry 128 includes one or more coils configured to generate one or more radio frequency pulses. In an embodiment, the circuitry 128 includes a plurality of radio frequency coils. In an embodiment, the circuitry 128 a plurality of coils configured to generate a time-varying magnetic field.

In an embodiment, a generated electromagnetic field stimulus is of a character and for a duration sufficient to elicit hemozoin nanoparticles within a biological sample to deliver magnetically induced hyperthermia therapy in vivo. Because hemozoin nanoparticles are paramagnetic, in an embodiment, applying magnetic field gradients can apply force to the hemozoin in malaria parasites. In an embodiment, applying time-varying magnetic fields to hemozoin can result in rapid somewhat oscillatory movement of the hemozoin particles thereby heating the hemozoin and hence the parasites; sufficient heat to negatively affect or kill the parasites, while not being substantially affecting the normal function of non-infected cells.

In an embodiment, the system 100 includes, among other things, circuitry 130 configured to detect scattering information associated with a plurality of hemozoin nanoparticles interrogated by at least one of a multiplexed dark-field interrogation stimulus or a multiplexed Rheinberg interrogation stimulus in the presence of a magnetic field.

In an embodiment, the system 100 includes, among other things, circuitry 128 configured to generate a magnetic field stimulus of a character and for a duration sufficient to elicit hemozoin nanoparticles within a biological sample to deliver magnetically induced hyperthermia therapy in vivo.

In an embodiment, the system 100 includes, among other things, circuitry 132 configured to dynamically control the magnetic field stimulus. In an embodiment, the circuitry 132 configured to dynamically control the magnetic field stimulus includes one or more processors 404 operably coupled to the circuitry 128 configured to generate the electromagnetic field stimulus and configured to manage one or more parameters associated with delivery of a pulsed magnetic stimulus to a region of a biological subject. In an embodiment, the circuitry 132 configured to dynamically control the magnetic field stimulus includes one or more processors 404 configured to regulate at least one of a delivery regimen parameter, a spaced-apart delivery pattern parameter, or a temporal delivery pattern parameter associated with generating the electromagnetic field stimulus.

In an embodiment, the system 100 includes, among other things, circuitry 134 configured to compare a detected scattering information to reference hemozoin dark-field scattering data. In an embodiment, the circuitry 134 configured to compare the nonlinear multi-harmonic response energy profile includes one or more computer-readable memory media having reference hemozoin nonlinear response information configured as a data structure 424. In an embodiment, the reference hemozoin nonlinear response information includes modeled reference comparison information. In an embodiment, the circuitry 134 configured to compare the nonlinear multi-harmonic response energy profile includes one or more computer-readable memory media having reference hemozoin nonlinear response information configured as a data structure 424. In an embodiment, the reference hemozoin nonlinear response information includes at least one of in situ detected nonlinear response information, hemozoin spectral information, or hemozoin nonlinear susceptibility information.

In an embodiment, the system 100 includes, among other things, circuitry 136 configured to compare (a) a nonlinear multi-harmonic response energy profile associated with at least one focal volume interrogated with a spatially patterned pulsed electromagnetic energy stimulus to (b) reference hemozoin nonlinear response information.

In an embodiment, the system 100 includes, among other things, circuitry 138 configured to magnetically induce at least one of an oscillation, a translation, or a rotation of hemozoin nanoparticles in a biological sample, the induced at least one of the oscillation, the translation, and the rotation of hemozoin nanoparticles in the biological sample of a character and for a duration sufficient to affect the integrity of an organelle of a plasmodium parasite. In an embodiment, the circuitry 138 configured to magnetically induce at least one of an oscillation, a translation, or a rotation of hemozoin nanoparticles in a biological tissue includes a flexible circuit having a one or more conductive traces configured to generate a magnetic field in the presence of an applied potential. In an embodiment, the circuitry 138 configured to magnetically induce at least one of an oscillation, a translation, or a rotation of hemozoin nanoparticles in a biological tissue includes a printed circuit having a one or more conductive traces configured to generate a magnetic field in the presence of an applied electrical current. In an embodiment, the circuitry 138 configured to magnetically induce at least one of an oscillation, a translation, or a rotation of hemozoin nanoparticles in a biological tissue includes at least one of a receiver 1206, transmitter 1210, or a transceiver 1208. In an embodiment, the circuitry 138 configured to magnetically induce at least one of an oscillation, a translation, or a rotation of hemozoin nanoparticles in a biological tissue includes at least one electromagnet. In an embodiment, the circuitry 138 configured to magnetically induce at least one of an oscillation, a translation, or a rotation of hemozoin nanoparticles in a biological tissue includes at least one permanent magnet.

In an embodiment, the system 100 includes, among other things, circuitry 140 configured to communicate comparison information associated with comparing the nonlinear multi-harmonic response energy profile.

In an embodiment, the system 100 includes, among other things, circuitry 142 configured to communicate treatment information associated with magnetically inducing at least one of the oscillation, the translation, and the rotation of hemozoin nanoparticles.

In an embodiment, the system 100 includes, among other things, circuitry 144 configured to detect a scattered energy from a biological tissue in at least one of a dark-field detection configuration or a Rheinberg detection configuration. In an embodiment, the circuitry 144 configured to detect the scattered energy includes at least one sensor 442 configured to receive a portion of the scattered energy in a dark-field detection configuration. In an embodiment, the circuitry 144 configured to detect the scattered energy includes at least one sensor 442 configured to receive a portion of the scattered energy in a Rheinberg detection configuration. In an embodiment, the circuitry 144 configured to detect the scattered energy includes a lens array assembly configured receive at least a portion of the scattered energy from the biological subject. In an embodiment, the circuitry 144 configured to detect the scattered energy includes a Rheinberg differential color illumination assembly configured receive at least a portion of the scattered energy from the biological subject. In an embodiment, the circuitry 144 configured to detect the scattered energy includes at least one Rheinberg filter.

In an embodiment, the system 100 includes, among other things, circuitry 146 configured to magnetically perturb hemozoin nanoparticles in a biological tissue in response to a comparison between detected scattered energy information and reference hemozoin nanoparticles scattered energy information. In an embodiment, the circuitry 146 configured to magnetically perturb hemozoin nanoparticles in a biological tissue includes a coil assembly configured to magnetically induce at least one of an oscillation, a translation, or a rotation of hemozoin nanoparticles in a biological tissue. In an embodiment, the circuitry 146 configured to magnetically perturb hemozoin nanoparticles in a biological tissue includes one or more conductive traces configured to cause at least one of an oscillation, a translation, or a rotation of hemozoin nanoparticles in a biological tissue. In an embodiment, the circuitry 146 configured to magnetically perturb hemozoin nanoparticles in a biological tissue includes one or more processors 404 that, when activated, generate a control signal that causes the comparison between the detected scattered energy and the reference hemozoin nanoparticles scattered energy information.

In an embodiment, the system 100 includes, among other things, circuitry 148 configured to impinge an effective amount of an electromagnetic energy stimulus in a dark-field configuration onto one or more regions of a biological tissue to produce scattered energy from the biological tissue. In an embodiment, the circuitry 148 configured to impinge the effective amount of an electromagnetic energy stimulus includes a lens array assembly configured to focus one or more incident electromagnetic energy stimuli onto the biological subject and to receive scattered energy therefrom.

In an embodiment, the system 100 includes, among other things, circuitry 150 configured to detect a nonlinear multi-harmonic response energy associated with hemozoin nanoparticles within at least one focal volume of a biological tissue interrogated by an electromagnetic energy stimulus. In an embodiment, the circuitry 150 configured to detect the nonlinear multi-harmonic response energy includes at least one charged-coupled device configured to detect at least one of a second harmonic response, a third harmonic response, or a fourth harmonic response associated with hemozoin nanoparticles within at least one focal volume interrogated by an electromagnetic energy stimulus. In an embodiment, the circuitry 150 configured to detect the nonlinear multi-harmonic response energy includes at least one ultraviolet-visible diode array detector for detecting at least one of a second harmonic response, a third harmonic response, or a fourth harmonic response associated with hemozoin nanoparticles within at least one focal volume interrogated by an electromagnetic energy stimulus. In an embodiment, the circuitry 150 configured to detect the nonlinear multi-harmonic response energy includes circuitry configured to detect a transcutaneously emitted multi-harmonic photonic response.

In an embodiment, the circuitry 150 configured to detect the nonlinear multi-harmonic response energy includes one or more sensors 442 for detecting a nonlinear response profile of one or more hemozoin nanoparticles within the at least one focal volume. In an embodiment, the circuitry 150 configured to detect the nonlinear multi-harmonic response energy includes one or more sensors 442 for detecting a spectral response of one or more hemozoin nanoparticles within the at least one focal volume. In an embodiment, the circuitry 150 configured to detect the nonlinear multi-harmonic response energy includes circuitry configured to detect, in situ, nonlinear multi-harmonic response energy associated with hemozoin nanoparticles within the at least one focal volume interrogated by the spatially patterned pulsed multiplexed electromagnetic energy stimulus. In an embodiment, the circuitry 150 configured to detect the nonlinear multi-harmonic response energy includes an optical assembly 112 and at least one sensor 442 for collecting and detecting via an epi-collection mode at least one of a second harmonic response, a third harmonic response, or a fourth harmonic response elicited by the spatially patterned pulsed multiplexed electromagnetic energy stimulus. In an embodiment, the circuitry 150 configured to detect the nonlinear multi-harmonic response energy includes an optical assembly 112 and at least one sensor 442 for collecting and detecting via a Rheinberg detection configuration at least one of a second harmonic response, a third harmonic response, and a fourth harmonic response elicited by the spatially patterned pulsed multiplexed electromagnetic energy stimulus.

In an embodiment, the system 100 includes, among other things, circuitry 152 configured to generate an effective amount of a pulsed electromagnetic energy stimulus to elicit a nonlinear response from hemozoin nanoparticles in a biological tissue within the at least one focal volume of the biological tissue. In an embodiment, the elicited nonlinear response is of a character and for a duration sufficient to modulate a biological activity of a malarial infectious agent.

Absorption, transmission, scattering, etc., of electromagnetic radiation varies among biological tissues, biological samples, equipment, other materials, or the like. For example, the range of about 800 nanometers to about 1300 nanometers is a range where photon absorption and scattering are minimal for dermal tissue (creating a region that is optimal for efficient optical power transfer across the skin). Accordingly, in an embodiment, the peak emission wavelength of the electromagnetic stimulus generated by the energy-emitting component 104 is chosen to maximize the delivery and detection to and from a sample of interest. For example, to improve transcutaneous transmission of an electromagnetic stimulus of and subsequent detection of a generated nonlinear optical response, a peak emission wavelength of electromagnetic stimulus is chosen within am range of about 1000 nanometers to about 1300 nanometers. This will result in a nonlinear optical response from hemozoin ranging from about 500 nanometers to about 650 nanometers (for second harmonic generation; one-half the wavelength); from about 333 nanometers to about 433 nanometers (for third harmonic generation; one-third the wavelength), etc. In an embodiment, one or more peak emission wavelengths of the electromagnetic stimulus generated by the energy-emitting component 104 are chosen to elicit a nonlinear optical response of hemozoin to emit within a wavelength range that damages genetic material. Other ranges may be more optimal for efficient optical power transfer across, for example, medical equipment, medical settings, in vitro ware, or the like.

In an embodiment, the circuitry 152 configured to generate the effective amount of a pulsed electromagnetic energy stimulus includes at least one of a first energy emitter having a peak emission wavelength ranging from about 690 nanometers to about 2100 nanometers and at least one of a second energy emitter having a peak emission wavelength ranging from about 1000 nanometers to about 2000 nanometers for multiplex nonlinear response assaying. In an embodiment, the circuitry 152 configured to generate the effective amount of a pulsed electromagnetic energy stimulus includes an energy-emitting component 104 configured to interrogate at least one focal volume with a spatially patterned pulsed multiplexed electromagnetic energy stimulus.

In an embodiment, the circuitry 152 configured to generate the effective amount of a pulsed electromagnetic energy stimulus includes one or more lasers, laser diodes, and light-emitting diodes. In an embodiment, the circuitry 152 configured to generate the effective amount of a pulsed electromagnetic energy stimulus includes one or more quantum dots, organic light-emitting diodes, microcavity light-emitting diodes, and polymer light-emitting diodes. In an embodiment, the circuitry 152 configured to generate the effective amount of a pulsed electromagnetic energy stimulus includes one or more femtosecond lasers. In an embodiment, the circuitry 152 configured to generate the effective amount of a pulsed electromagnetic energy stimulus includes a patterned energy-emitting source. In an embodiment, the circuitry 152 configured to generate the effective amount of a pulsed electromagnetic energy stimulus includes a lens array configured to deliver a spaced-apart energy stimuli having at least a first region and a second region, the second region having a focal depth different from the first region.

In an embodiment, the system 100 includes, among other things, circuitry 154 configured to generate a multiplexed pulsed electromagnetic energy stimulus having a peak power ranging from about 400 gigawatts to about 8 terawatts.

In an embodiment, the system 100 includes, among other things, circuitry 156 configured to direct the multiplexed pulsed electromagnetic energy stimulus on a plurality of focal volumes in a biological subject.

In an embodiment, the system 100 includes, among other things, circuitry 158 configured to detect a multi-harmonic response associated with a plurality of hemozoin nanoparticles in a biological tissue within one or more of the plurality of focal volumes interrogated by the multiplexed pulsed electromagnetic energy stimulus. In an embodiment, the circuitry 158 configured to detect the multi-harmonic response includes at least one epi-direction sensor for detecting, in situ, an emitted multi-harmonic response associated with the plurality of hemozoin nanoparticles in a biological tissue interrogated by the multiplexed pulsed electromagnetic energy stimulus.

In an embodiment, the system 100 includes, among other things, a magnetic field component 160 configured to generate a magnetic field of a character and for a duration sufficient to magnetically align, in vivo, a plurality of hemozoin nanoparticles. In an embodiment, the magnetic field component 160 includes a radio frequency transmitter configured to generate a radio frequency signal. In an embodiment, the magnetic field component 160 includes one or more coils configured to generate one or more radio frequency pulses. In an embodiment, the medical diagnostic device is configured for removable attachment to a biological surface of a biological subject.

In an embodiment, the system 100 includes, among other things, a physical coupling element configured to removably-attach at least one of the dark-field electromagnetic energy emitting component, the magnetic field component, and the optical energy sensor component to a biological surface of a biological subject.

In an embodiment, the system 100 includes, among other things, an actively-controllable magnetic field generator 162 configured to deliver a varying magnetic field stimulus at a dose sufficient to cause heat generation from hemozoin nanoparticles within a biological sample. In an embodiment, the actively-controllable magnetic field generator 162 includes circuitry configured to generate and deliver an electromagnetic energy stimulus of a character and for a duration sufficient to cause hemozoin nanoparticles within the biological sample interrogated by an electromagnetic energy stimulus to generate thermal energy. In an embodiment, the actively-controllable magnetic field generator 162 includes an electrical coil assembly that, when energized, generates a magnetic field of a character and for a duration to induce one or more of the Brownian process and the Neélian process within the biological sample including hemozoin nanoparticles. In an embodiment, the actively-controllable magnetic field generator 162 includes a magnetic field generating coil assembly for applying a varying magnetic field. In an embodiment, the actively-controllable magnetic field generator 162 includes a volume coil arrangement including a plurality of coils for generating a circularly polarized magnetic field. In an embodiment, the actively-controllable magnetic field generator 162 includes one or more electromagnets.

In an embodiment, the actively-controllable magnetic field generator 162 includes one or more alternating current electromagnets. In an embodiment, the actively-controllable magnetic field generator 162 includes one or more coils that are configured to generate a magnetic field of a character and for a duration sufficient to increase the temperature of a region within a plasmodium parasite including the hemozoin nanoparticles by about 3° C. to about 22° C. In an embodiment, the actively-controllable magnetic field generator 162 includes one or more coils that are configured to generate a magnetic field of a character and for a duration sufficient to increase the temperature of a hemozoin-containing-region within a plasmodium parasite existing within the biological sample by about 3° C. to about 10° C. In an embodiment, the actively-controllable magnetic field generator 162 includes one or more coils that are configured to generate a magnetic field of a character and for a duration sufficient to increase the temperature of a region within a plasmodium parasite including the hemozoin nanoparticles by about 3° C. to about 4° C.

In an embodiment, the actively-controllable magnetic field generator 162 generates a magnetic field of a character and for a duration sufficient to cause a temperature increase within a region of a plasmodium parasite including the hemozoin nanoparticles. In an embodiment, the actively-controllable magnetic field generator 162 generates a magnetic field of a sufficient strength or duration to attenuate an activity of a malarial infectious agent. In an embodiment, the actively-controllable magnetic field generator 162 provides a magnetic field of a sufficient strength or duration to modulate heme polymerase activity of a malarial infectious agent.

In an embodiment, the actively-controllable magnetic field generator 162 provides a magnetic field of a character and for a duration sufficient to ameliorate a plasmodium parasitic effect without substantially disrupting the integrity of an erythrocyte encapsulating a plasmodium parasite. In an embodiment, the actively-controllable magnetic field generator 162 provides a magnetic field of a character and for a duration sufficient to cause a temperature increase within a region of a plasmodium parasite in the biological sample, the temperature increase sufficient to cause heat-induced programmed cell death in the plasmodium parasite.

In an embodiment, the actively-controllable magnetic field generator 162 provides a magnetic field of a character and for a duration sufficient to cause programmed cell death of a host cell carrying the malarial infectious agent. In an embodiment, the actively-controllable magnetic field generator 162 provides a magnetic field of a character and for a duration sufficient to cause a temperature increase within a region of a plasmodium parasite in the biological sample, the temperature increase sufficient to reduce a parasitemia level. In an embodiment, the actively-controllable magnetic field generator 162 generates an alternating current magnetic field of a character and for a duration sufficient to cause a temperature increase in a region within a plasmodium parasite including the hemozoin nanoparticles and to ameliorate a plasmodium parasitic effect without substantially disrupting the integrity of an erythrocyte encapsulating the plasmodium parasite.

In an embodiment, the actively-controllable magnetic field generator 162 includes one or more conductive coils configured to generate a time-varying magnetic field in response to an applied current, the time-varying magnetic field of a character and for a duration sufficient to cause hemozoin nanoparticles within the biological sample to generate heat as a result of one or more of the Brownian process and the Neélian process. In an embodiment, the actively-controllable magnetic field generator 162 generates a magnetic field of a character and for a duration sufficient to induce heat-damage to an organelle membrane within a plasmodium parasite within the biological sample. In an embodiment, the actively-controllable magnetic field generator 162 includes at least one radio frequency transmitter including one or more one radio frequency coils configured to generate a localized radio frequency stimulus.

In an embodiment, the actively-controllable magnetic field generator 162 is configured to concurrently or sequentially generate at least a first electromagnetic energy stimulus and a second electromagnetic energy stimulus, the first electromagnetic energy stimulus of a character and for a duration sufficient to magnetically align hemozoin nanoparticles in a biological tissue, the second electromagnetic energy stimulus of a character and for a duration sufficient to magnetically induce at least one of an oscillation, a translation, or a rotation of the hemozoin nanoparticles in the biological tissue. In an embodiment, the induced at least one of the oscillation, the translation, and the rotation of the hemozoin nanoparticles in a biological tissue is sufficient to affect an integrity of an organelle of a malarial infectious agent. In an embodiment, the induced at least one of the oscillation, the translation, and the rotation of the hemozoin nanoparticles in a biological tissue is sufficient to affect the integrity of a digestive food vacuole of a malaria parasite. In an embodiment, the induced at least one of the oscillation, the translation, and the rotation of the hemozoin nanoparticles in a biological tissue is sufficient to disrupt an in vive heme polymerization process.

In an embodiment, the system 100 includes, among other things, a computing device 402 operatively coupled to the actively-controllable magnetic field generator. In an embodiment, the computing device 402 includes one or more processors 404 for controlling at least one of a magnetic field ON duration, a magnetic field strength, a magnetic field frequency, or a magnetic field waveform.

In an embodiment, the system 100 includes, among other things, a dark-field electromagnetic energy emitting component configured to interrogate at least one focal volume of biological tissue with a multi-mode dark-field stimulus.

In an embodiment, the system 100 includes, among other things, one or more power sources 700. In an embodiment, the power source 700 is electromagnetically, magnetically, ultrasonically, optically, inductively, electrically, or capacitively coupleable to one or more energy-emitting components 104. In an embodiment, the power source 700 is carried by a monitor or treatment device 102. In an embodiment, the power source 700 comprises at least one rechargeable power source 702. In an embodiment, the power source 700 is configured to wirelessly receive power from a remote power supply.

In an embodiment, the monitor or treatment device 102 includes one or more biological-subject (e.g., human)-powered generators 704. In an embodiment, the biological-subject-powered generator 704 is configured to harvest energy from, for example, motion of one or more joints. In an embodiment, the biological-subject-powered generator 704 is configured to harvest energy generated by the biological subject using at least one of a thermoelectric generator 706, piezoelectric generator 708, electromechanical generator 710 (e.g., a microelectromechanical systems (MEMS) generator, or the like), biomechanical-energy harvesting generator 712, or the like.

In an embodiment, the biological-subject-powered generator 704 is configured to harvest thermal energy generated by the biological subject. In an embodiment, a thermoelectric generator 706 is configured to harvest heat dissipated by the biological subject. In an embodiment, the biological-subject-powered generator 704 is configured to harvest energy generated by any physical motion or movement (e.g., walking,) by biological subject. For example, in an embodiment, the biological-subject-powered generator 704 is configured to harvest energy generated by the movement of a joint within the biological subject. In an embodiment, the biological-subject-powered generator 704 is configured to harvest energy generated by the movement of a fluid (e.g., biological fluid) within the biological subject.

Among power sources 700 examples include, but are not limited to, one or more button cells, chemical battery cells, a fuel cell, secondary cells, lithium ion cells, micro-electric patches, nickel metal hydride cells, silver-zinc cells, capacitors, super-capacitors, thin film secondary cells, ultra-capacitors, zinc-air cells, or the like. Further non-limiting examples of power sources 700 include one or more generators (e.g., electrical generators, thermo energy-to-electrical energy generators, mechanical-energy-to-electrical energy generators, micro-generators, nano-generators, or the like) such as, for example, thermoelectric generators, piezoelectric generators, electromechanical generators, biomechanical-energy harvesting generators, or the like. In an embodiment, the monitor or treatment device 102 includes one or more generators configured to harvest mechanical energy from for example, ultrasonic waves, mechanical vibration, blood flow, or the like. In an embodiment, the monitor or treatment device 102 includes one or more power receivers 732 configured to receive power from an in vivo or ex vivo power source. In an embodiment, the in vivo power source includes at least one of a thermoelectric generator, a piezoelectric generator, an electromechanical energy to electricity generator, or a biomechanical-energy harvesting generator.

In an embodiment, the power source 700 includes at least one of a thermoelectric generator, a piezoelectric generator, an electromechanical generator, or a biomechanical-energy harvesting generator, and at least one of a button cell, a chemical battery cell, a fuel cell, a secondary cell, a lithium ion cell, a micro-electric patch, a nickel metal hydride cell, silver-zinc cell, a capacitor, a super-capacitor, a thin film secondary cell, an ultra-capacitor, or a zinc-air cell. In an embodiment, the power source 700 includes at least one rechargeable power source.

In an embodiment, a monitor or treatment device 102 includes a power source 700 including at least one of a thermoelectric generator a piezoelectric generator, an electromechanical generator, or a biomechanical-energy harvesting generator. In an embodiment, the power source 700 is configured to manage a duty cycle associated with emitting an effective amount of the electromagnetic energy stimulus from the one or more energy-emitting components 104. In an embodiment, the power source 700 is configured to manage a duty cycle associated with emitting an effective amount of a sterilizing energy stimulus from the one or more energy-emitting components 104.

In an embodiment, the power source 700 is configured to manage a duty cycle associated with magnetically inducing at least one of an oscillation, a translation, or a rotation of hemozoin nanoparticles in a biological tissue. In an embodiment, the power source 700 is configured to manage a duty cycle associated with comparing the nonlinear multi-harmonic response energy profile associated with at least one focal volume interrogated with the spatially patterned pulsed electromagnetic energy stimulus to reference hemozoin nonlinear response information. In an embodiment, the system 100 includes, among other things, an energy storage device. In an embodiment, the energy storage device includes at least one of a battery, a capacitor, or a mechanical energy store.

Figure 2A:
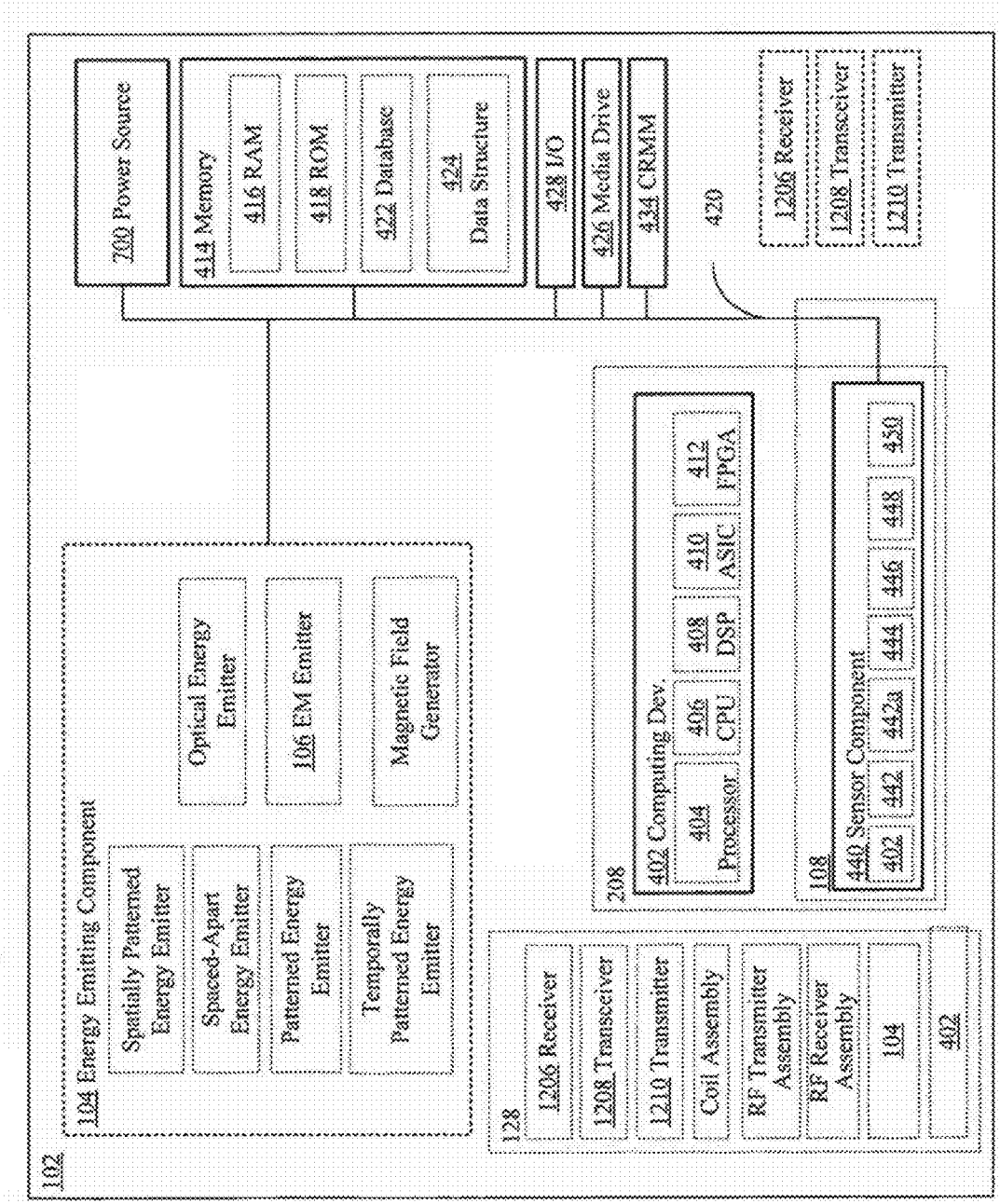
FIG. 2A is a perspective view of a system for modulating plasmodium parasitic activity according to one embodiment.

FIG. 2A shows a system 100 for modulating plasmodium parasitic activity. The system 100 for modulating plasmodium parasitic activity includes, among other things, circuitry 128 configured to generate a magnetic field stimulus of a character and for a duration sufficient to elicit hemozoin nanoparticles within a biological sample to deliver magnetically induced hyperthermia therapy in situ, in vitro, in vivo, or the like. In situ includes in vivo or in vitro. In an embodiment, the system 100 for modulating plasmodium parasitic activity includes circuitry 208 configured to dynamically control the magnetic field stimulus. In an embodiment, the circuitry 208 configured to dynamically control the magnetic field stimulus includes one or more processors 404 operably coupled to the circuitry 202 configured to generate the electromagnetic field stimulus and configured to manage one or more parameters associated with deliver of a pulsed magnetic stimulus to a region of a biological subject. In an embodiment, the circuitry 208 configured to dynamically control the magnetic field stimulus includes one or more processors 404 configured to regulate at least one of a delivery regimen parameter, a spaced-apart delivery pattern parameter, or a temporal delivery pattern parameter associated with generating the electromagnetic field stimulus.

FIG. 2B shows a system 100 for optically monitoring/modulating a plasmodium parasitic activity. In an embodiment, the system 100 includes a scanning/projection system 210 and a detection subsystem 212 operating under at least one computing device 402. The system 100 may be implemented in a variety of formats, such as, but not limited to, an optical scanner-based system, such as that described in one or more of U.S. Pat. No. 6,445,362, U.S. 2006/0284790 and/or U.S. 2005/0020926.

In one approach, the scanning/projection system 210 directs one or more electromagnetic energy stimuli 214 through a beam splitter 216 and through an optical lens assembly 218 toward a biological subject's eye 220. For example, the system 100 directs an effective amount of an electromagnetic energy stimulus 214 onto one or more focal volumes of a biological subject to produce scattered radiation from the biological subject, and detects using a dark field detection configuration at least a portion of the scattered radiation 225.

In an illustrative embodiment, the system 100 employs one or more energy-emitting components 104, such as laser diodes or fiber coupled lasers a having a peak emission wavelength ranging from about 690 nanometers to about 2100 nanometers, for at least one of the illuminating beams 214. The monitoring/modulating system 210 scans the illuminating beams 214 through a raster pattern or a Lissajous pattern, for example.

The optical lens assembly 218 couples the scanned illuminating beam 214 into the eye, through its pupil where the illuminating beam of light 214 strikes the retina 222. In some approaches, the optical lens assembly 218 may provide a beam 224 that converges in a field of interest, such as at or near the surface of a retina 222. In other approaches, the beam may be substantially collimated. The beam splitter 216 may be any of a variety of optical structures that can selectively transmit and/or re-direct at least a portion of light along one or more paths. In an illustrative embodiment, the beam splitter may be responsive to one or more wavelengths of light to selectively transmit and/or re-direct at least a portion of light. As will be described herein, some of the light that returns from the field of interest is collected using a differential illumination configuration. The beam splitter 216 may be configured to selectively transmit to the eye light at an input wavelength, while selectively redirecting light at a scattered wavelength, and/or the input wavelength. Note that the beam splitter may also redirect all or a portion of the returned light responsive to polarization or other characteristics of light.

Figure 3A:
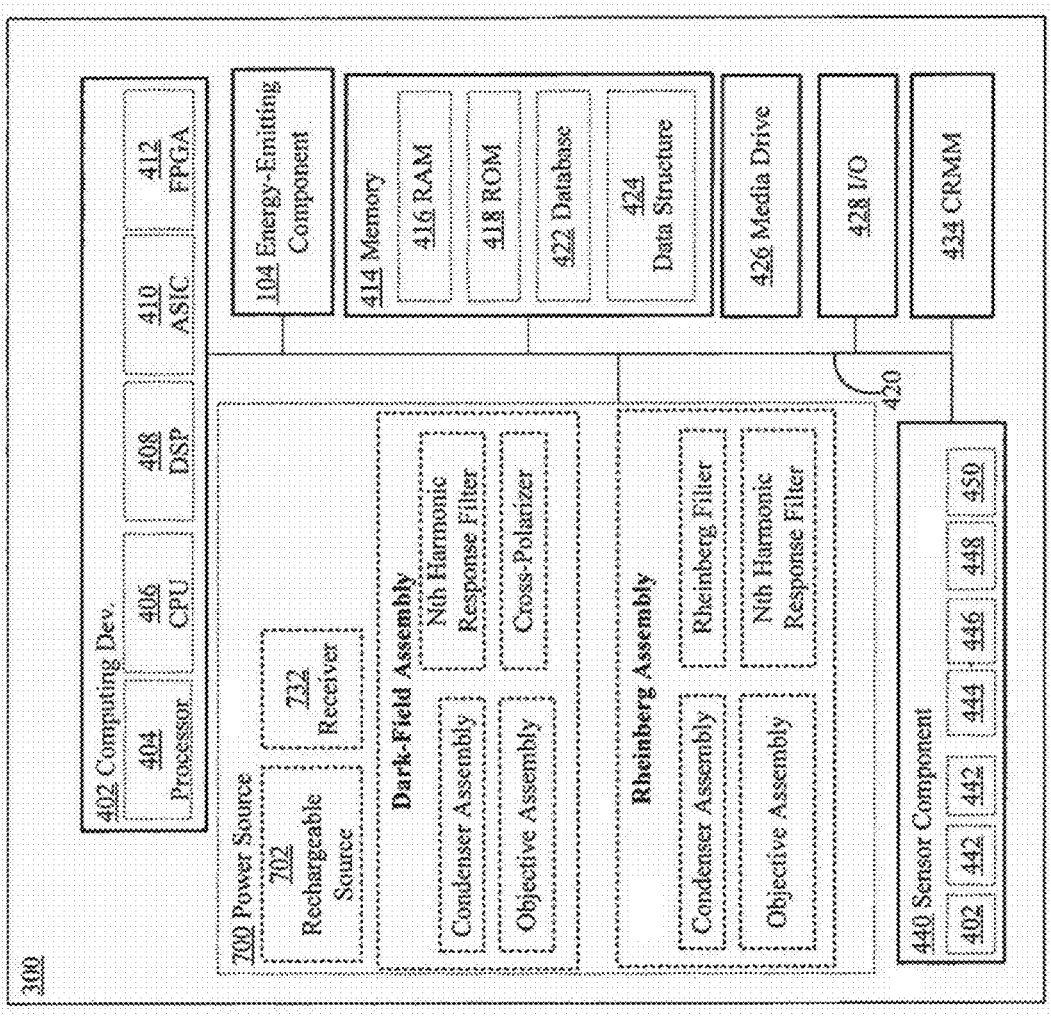
FIG. 3A is as perspective view of a hemozoin-monitoring device according to one embodiment.

FIG. 3A shows a hemozoin-monitoring device 300 in which one or more methodologies or technologies may be implemented. The hemozoin-monitoring device 300 includes, among other things, a sensor component 440 configured to detect a nonlinear multi-harmonic response profile associated with hemozoin nanoparticles in a biological tissue within multiple focal volumes interrogated by an electromagnetic energy stimulus (e.g., a pulsed electromagnetic energy stimulus, a spatially-patterned electromagnetic energy stimulus, a multiplexed electromagnetic energy stimulus, a spatially-patterned pulsed multiplexed electromagnetic energy stimulus, a temporally patterned electromagnetic energy stimulus, or the like). In an embodiment, the sensor component 440 is configured to detect a nonlinear multi-harmonic response profile using one or more differential illumination configurations (e.g., dark-field illumination, Rheinberg illumination, or the like). In an embodiment, the sensor component 440 is configured to detect a nonlinear multi-harmonic response profile using at least one of a dark-field detection configuration or a Rheinberg detection configuration. In an embodiment, the sensor component 440 is configured to detect a spectral signature characteristic for hemozoin optionally using at least one of a dark-field detection configuration or a Rheinberg detection configuration.

The hemozoin-monitoring device 300 can includes, among other things, one or more computer-readable storage media including executable instructions stored thereon that, when executed on a computer, instruct a computing device 402 to retrieving from storage one or more parameters associated with reference hemozoin nonlinear response information, and perform a comparison of a detected nonlinear multi-harmonic response profile to the retrieved one or more parameters. In an embodiment, the hemozoin-monitoring device 300 includes a transceiver 1208 configured to concurrently or sequentially transmit or receive information.

Figure 3B:
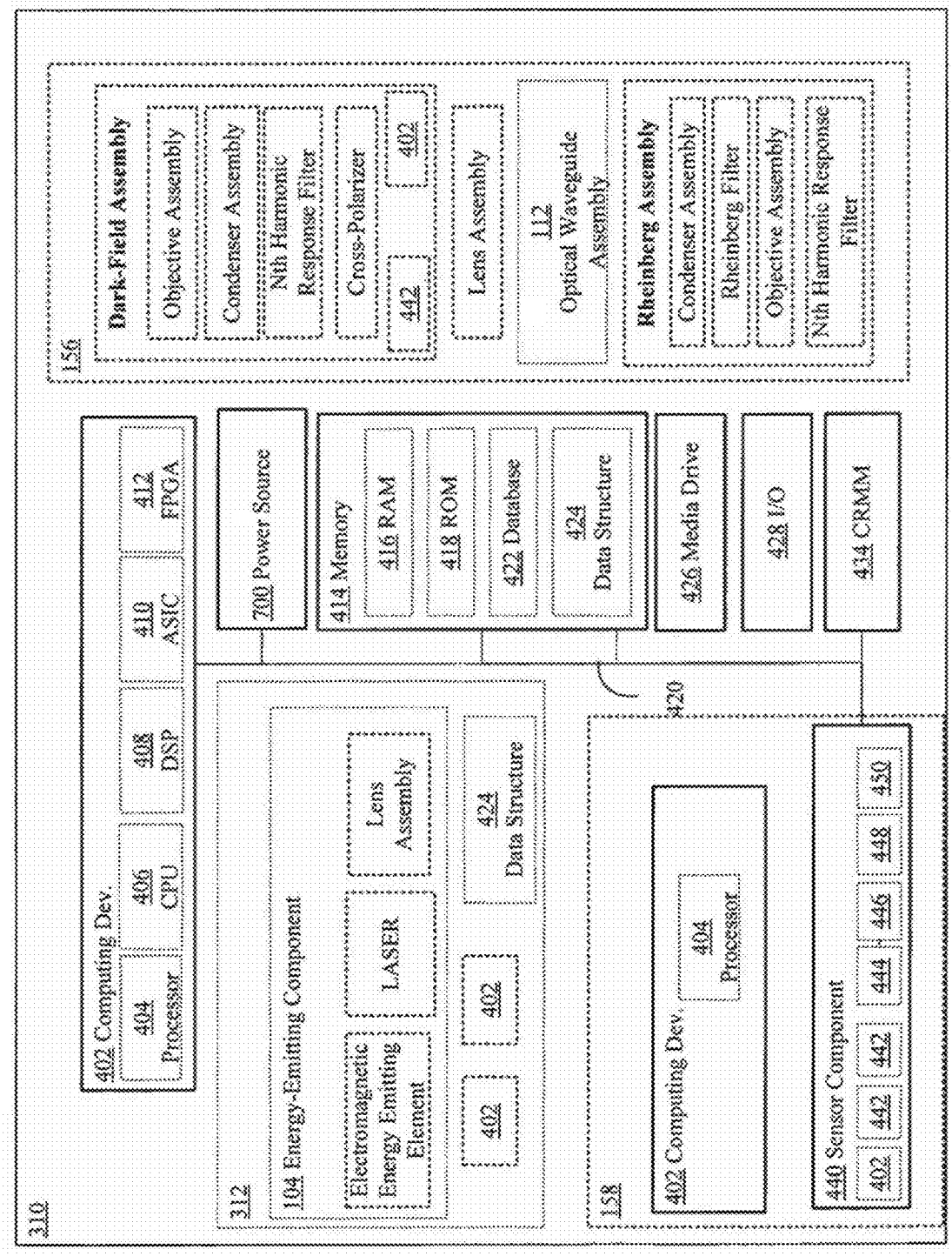
FIG. 3B is a perspective view of a medical diagnostic device according to one embodiment.

FIG. 3B shows a medical diagnostic device 310 in which one or more methodologies or technologies may be implemented. The medical diagnostic 310 includes, among other things, circuitry 312 configured to generate a multiplexed pulsed electromagnetic energy stimulus having a peak power ranging from about 400 gigawatts to about 8 terawatts. In an embodiment, the medical diagnostic device 310 includes circuitry 156 configured to direct the multiplexed pulsed electromagnetic energy stimulus on a plurality of focal volumes in a biological subject. In an embodiment, the medical diagnostic device 310 includes circuitry 158 configured to detect a multi-harmonic response associated with a plurality of hemozoin nanoparticles in a biological tissue within one or more of the plurality of focal volumes interrogated by the multiplexed pulsed electromagnetic energy stimulus.

Figure 3C:
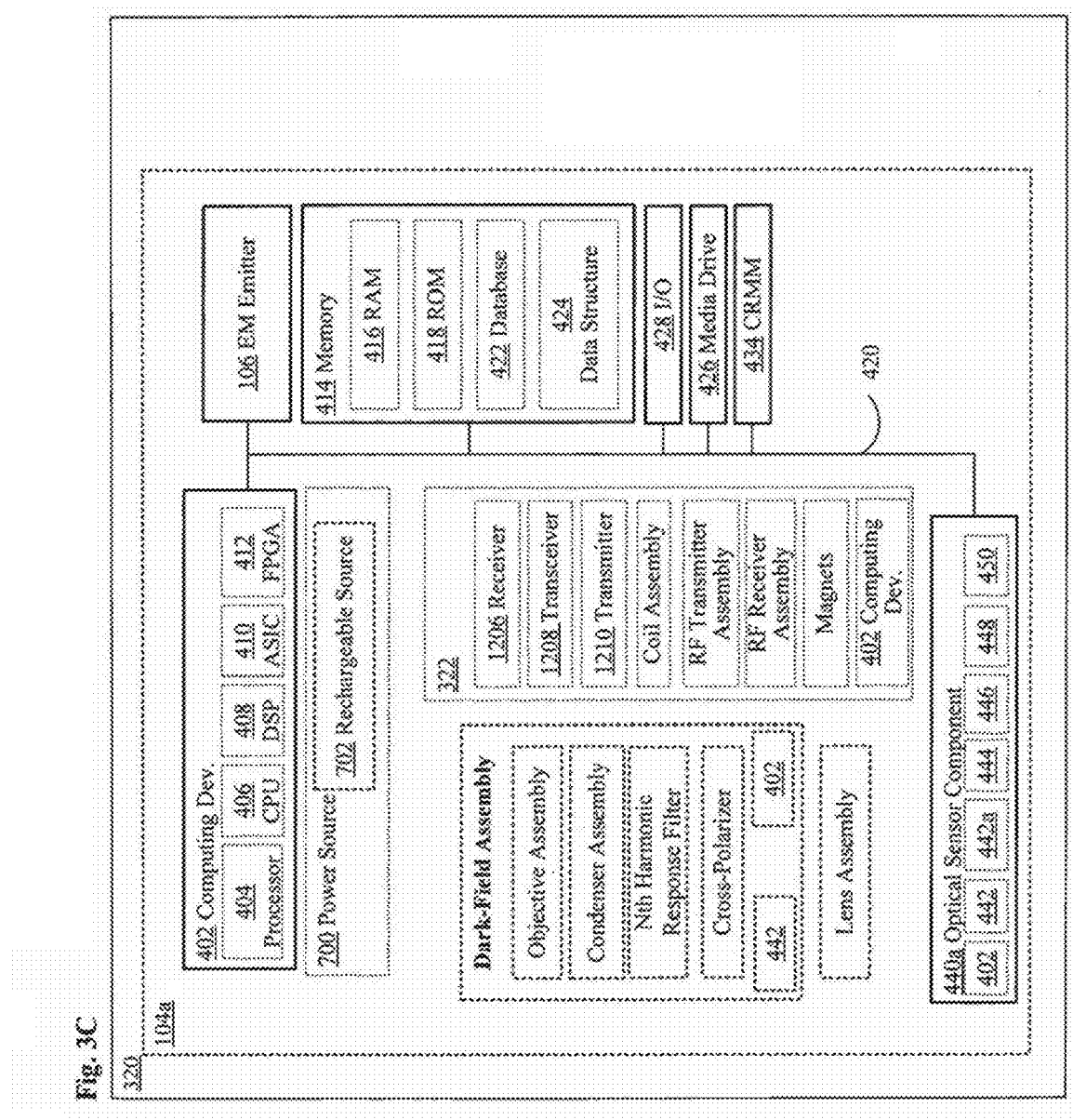
FIG. 3C is a perspective view of a medical diagnostic device according to one embodiment.

FIG. 3C shows a medical diagnostic device 320 which one or more methodologies or technologies may be implemented. The medical diagnostic device 320 includes, among other things, a dark-field electromagnetic energy emitting component 104a. In an embodiment, the dark-field electromagnetic energy emitting component 104a is configured to deliver a multi-mode dark-field interrogation stimulus to at least one blood vessel. The medical diagnostic device 320 can includes, among other things, a magnetic field component 322. In an embodiment, the magnetic field component 322 generates a magnetic field of a character and for a duration sufficient to magnetically align, in vivo, a plurality of hemozoin nanoparticles. The medical diagnostic device 320 includes, among other things, an optical energy sensor component 440a. In an embodiment, the optical energy sensor component 440a is configured to detect scatter optical energy from the plurality of hemozoin nanoparticles interrogated by the multi-mode dark-field interrogation stimulus in the presence of the magnetic field.

FIG. 3D shows an in situ hemozoin-monitoring device 330 in which one or more methodologies or technologies may be implemented. The in situ hemozoin-monitoring device 330 includes, among other things, an actively-controllable excitation component 104b configured to deliver a spatially-patterned pulsed electromagnetic energy stimulus to one or more focal volumes and configured to elicit a non-linear multi-harmonic response information from hemozoin nanoparticles in a biological tissue within the multiple focal volumes. In an embodiment, the in situ hemozoin-monitoring device 330 includes a control means 332 operably coupled to the actively-controllable excitation 104b component and configured to regulate at least one of a numerical aperture, a spaced-apart delivery pattern parameter, or a temporal delivery pattern parameter associated with the delivery of the spatially-patterned pulsed electromagnetic energy stimulus. In an embodiment, the actively-controllable excitation component 104b is configured to regulate at least one of parameter associated with a peak power, a peak irradiance, a focal spot size, or a pulse width.

Figure 3E:
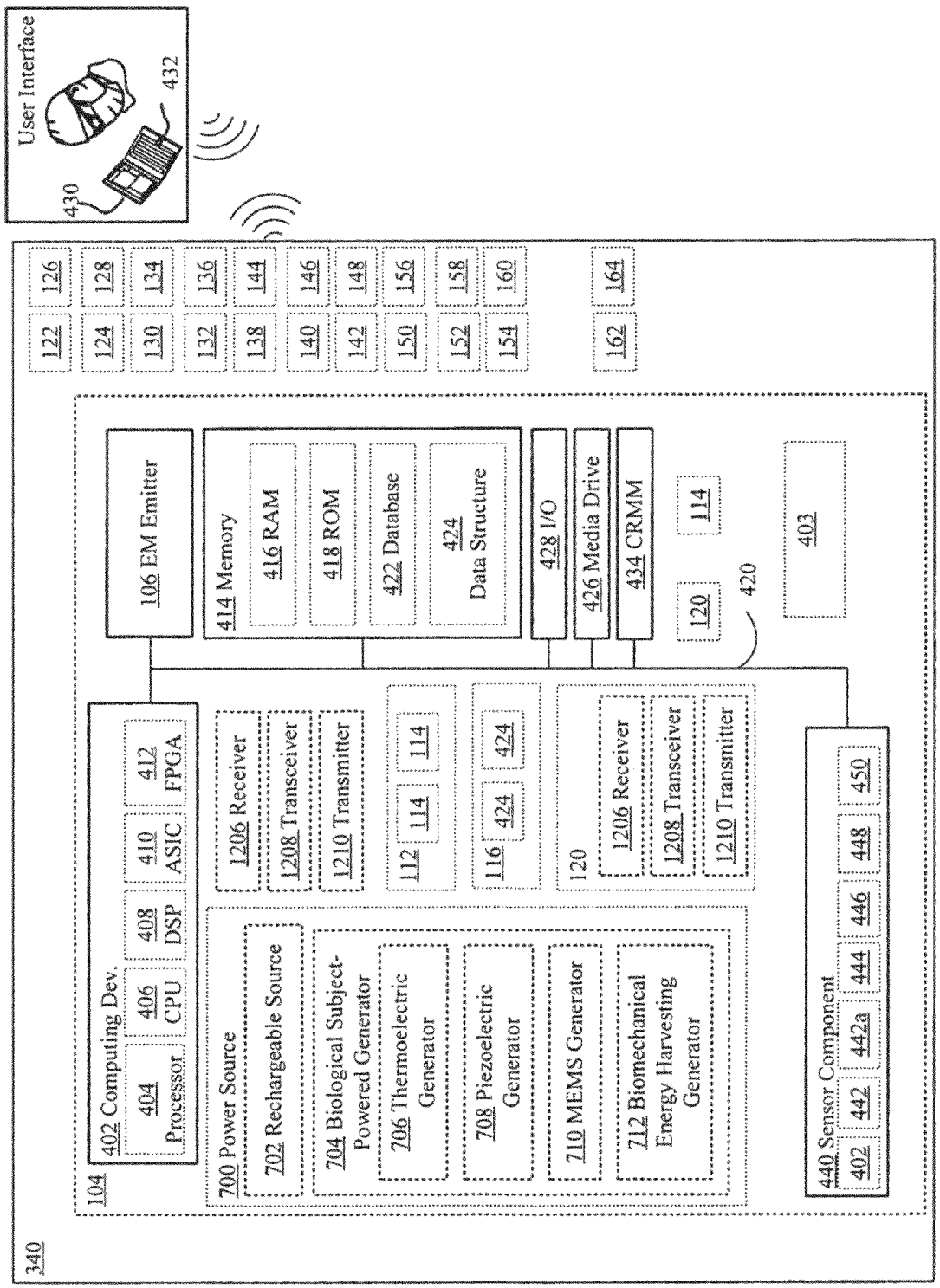
FIG. 3E is a perspective view of an anti-malarial therapeutic device according to one embodiment.

FIG. 3E shows an anti-malarial therapeutic device 340 in which one or more methodologies or technologies may be implemented. In an embodiment, the anti-malarial therapeutic device 340 includes, among other things, a sensor component 440 including at least one sensor 442 configured to detect nonlinear multi-harmonic response energy associated with hemozoin nanoparticles within at least one focal volume of a biological tissue interrogated by an electromagnetic energy stimulus. In an embodiment, the anti-malarial therapeutic device 340 includes an energy-emitting component 104 configured to deliver an effective amount of a electromagnetic energy stimulus to elicit a nonlinear optical response from hemozoin nanoparticles within the biological tissue, the elicited nonlinear response of a character and for a duration sufficient to modulate a biological activity of a malarial infectious agent within the biological tissue. In an embodiment, the anti-malarial therapeutic device 340 includes a computing device 402 operably coupled to at least one sensor 442 of the sensor component 440 and the energy-emitting component 104, the computing device 402 configured to provide a control signal to the energy-emitting component.

Figure 4A:
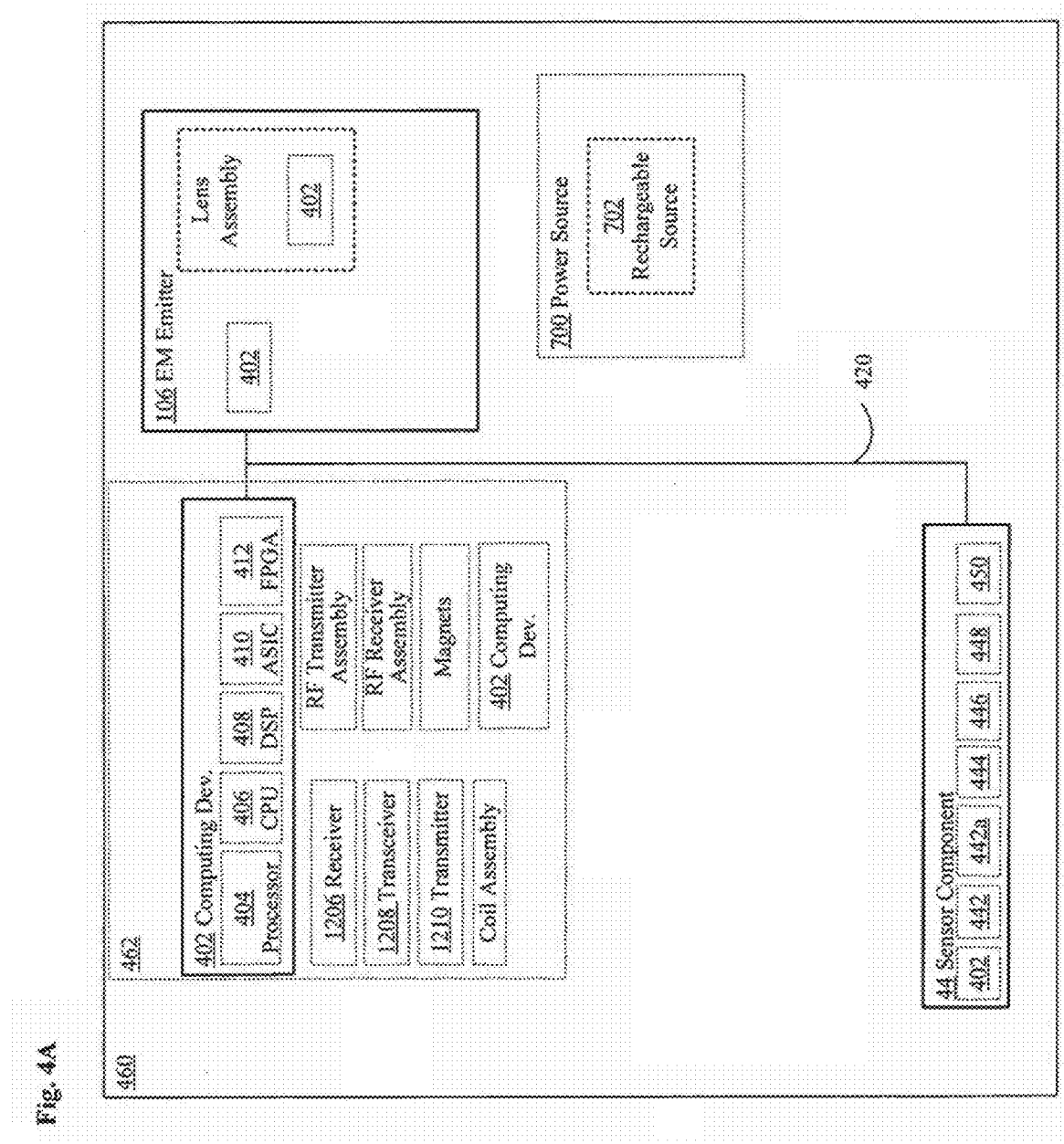
FIG. 4A is a perspective view of an apparatus according to one embodiment.

FIG. 4A shows an apparatus 460 in which one or more methodologies or technologies may be implemented. The apparatus 460 includes, among other things, an actively-controllable magnetic field generator 462 and a computing device operatively coupled to the actively-controllable magnetic field generator 462. In an embodiment, the actively-controllable magnetic field generator 462 is configured to deliver a varying magnetic field stimulus at a dose sufficient to cause heat generation from hemozoin nanoparticles within a biological sample. In an embodiment, the computing device 402 is operatively coupled to the actively-controllable magnetic field generator 462, and includes one or more processors 404 for controlling at least one of a magnetic field ON duration, a magnetic field strength, a magnetic field frequency, or a magnetic field waveform.

Figure 4B:
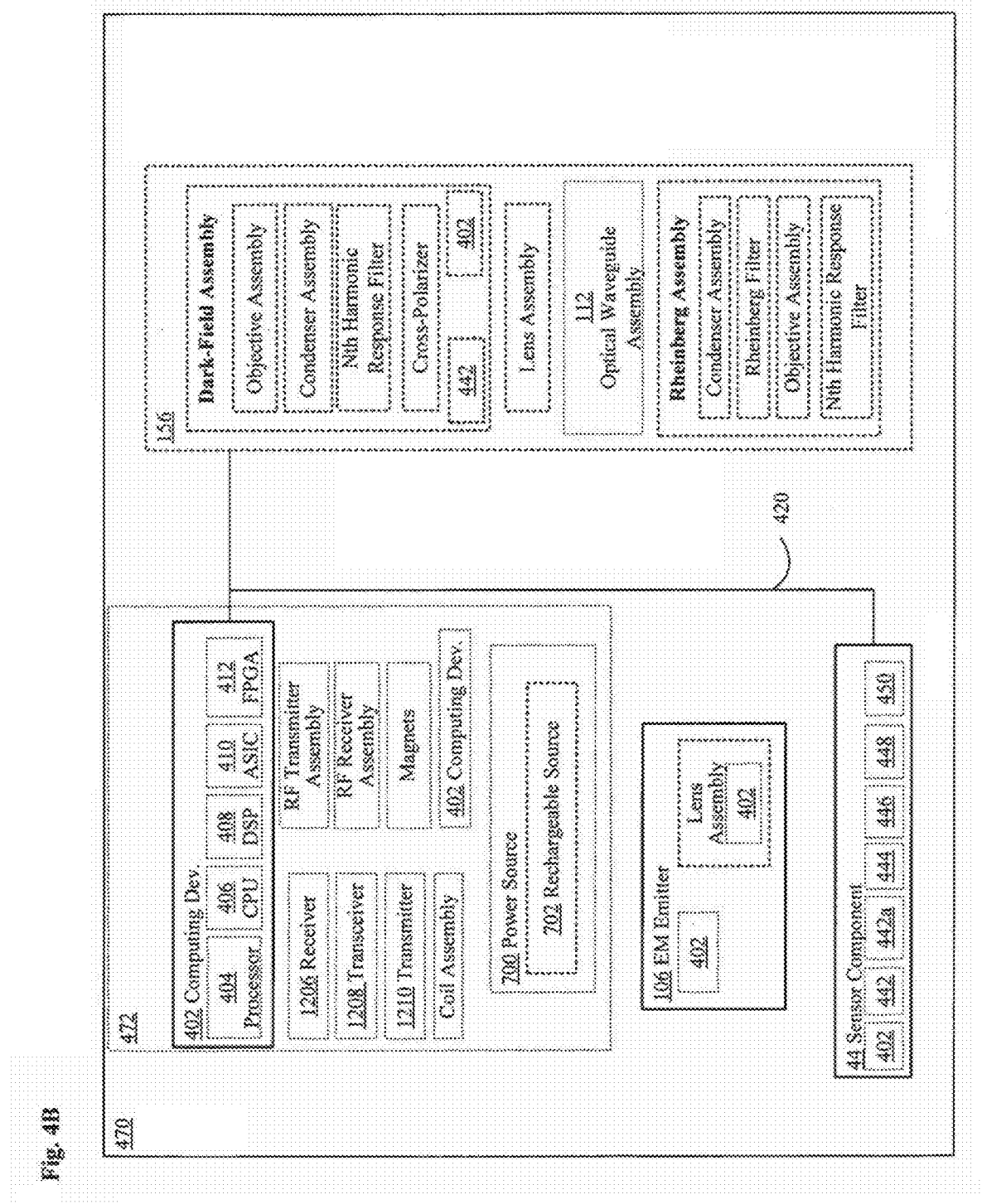
FIG. 4B is a perspective view of an apparatus according to one embodiment.

FIG. 4B shows an apparatus 470 in which one or more methodologies or technologies may be implemented. In an embodiment, the apparatus 460 includes a magnetic field generator 472 configured to concurrently or sequentially generate at least a first electromagnetic energy stimulus and a second electromagnetic energy stimulus, the first electromagnetic energy stimulus of a character and for a duration sufficient to magnetically align hemozoin nanoparticles in a biological tissue, the second electromagnetic energy stimulus of a character and for a duration sufficient to magnetically induce at least one of an oscillation, a translation, or a rotation of the hemozoin nanoparticles in the biological tissue.

FIG. 5 shows an example of a method 500 for detecting a condition associated with plasmodium-infected erythrocytes. At 510, the method 500 includes comparing, via circuitry, a nonlinear multi-harmonic response profile associated with at least one focal volume interrogated with a spatially-patterned pulsed electromagnetic energy stimulus to reference hemozoin nonlinear response information. At 512, comparing, using circuitry, the nonlinear multi-harmonic response profile associated with the at least one focal volume interrogated with the spatially-patterned pulsed electromagnetic energy stimulus to the reference hemozoin nonlinear response information includes generating a comparison of the nonlinear multi-harmonic response profile to reference hemozoin nonlinear response information configured as a physical data structure 424. At 514, comparing, using circuitry, the nonlinear multi-harmonic response profile associated with the at least one focal volume interrogated with the spatially-patterned pulsed electromagnetic energy stimulus to the reference hemozoin nonlinear response information includes comparing one or more of an elicited second harmonic response, an elicited third harmonic response, and an elicited fourth harmonic response to the reference hemozoin nonlinear response information. At 516, comparing, using circuitry, the nonlinear multi-harmonic response profile associated with the at least one focal volume interrogated with the spatially-patterned pulsed electromagnetic energy stimulus to the reference hemozoin nonlinear response information includes comparing at least one of an in situ detected second harmonic response, an in situ detected third harmonic response, and an in situ detected fourth harmonic response to the reference hemozoin nonlinear response information. At 518, comparing, using circuitry, the nonlinear multi-harmonic response profile associated with the at least one focal volume interrogated with the spatially-patterned pulsed electromagnetic energy stimulus to the reference hemozoin nonlinear response information includes comparing a detected nonlinear photonic response to the reference hemozoin nonlinear response information.

At 520, the method 500 can further include generating a response based on the comparison of the detected nonlinear multi-harmonic response energy to the reference hemozoin nonlinear response information. At 522, generating the response includes providing at least one of a visual, an audio, a haptic, or a tactile representation of a nonlinear multi-harmonic response profile associated with the at least one focal volume interrogated with the spatially-patterned pulsed electromagnetic energy stimulus. At 524, generating the response includes determining one or more of a presence, an absence, or a severity of malaria condition based on the comparison of the detected nonlinear multi-harmonic response energy to the reference hemozoin nonlinear response information. At 526, generating the response includes determining a malaria infection score based on the comparison of the detected nonlinear multi-harmonic response energy to the reference hemozoin nonlinear response information.

Figure 6:
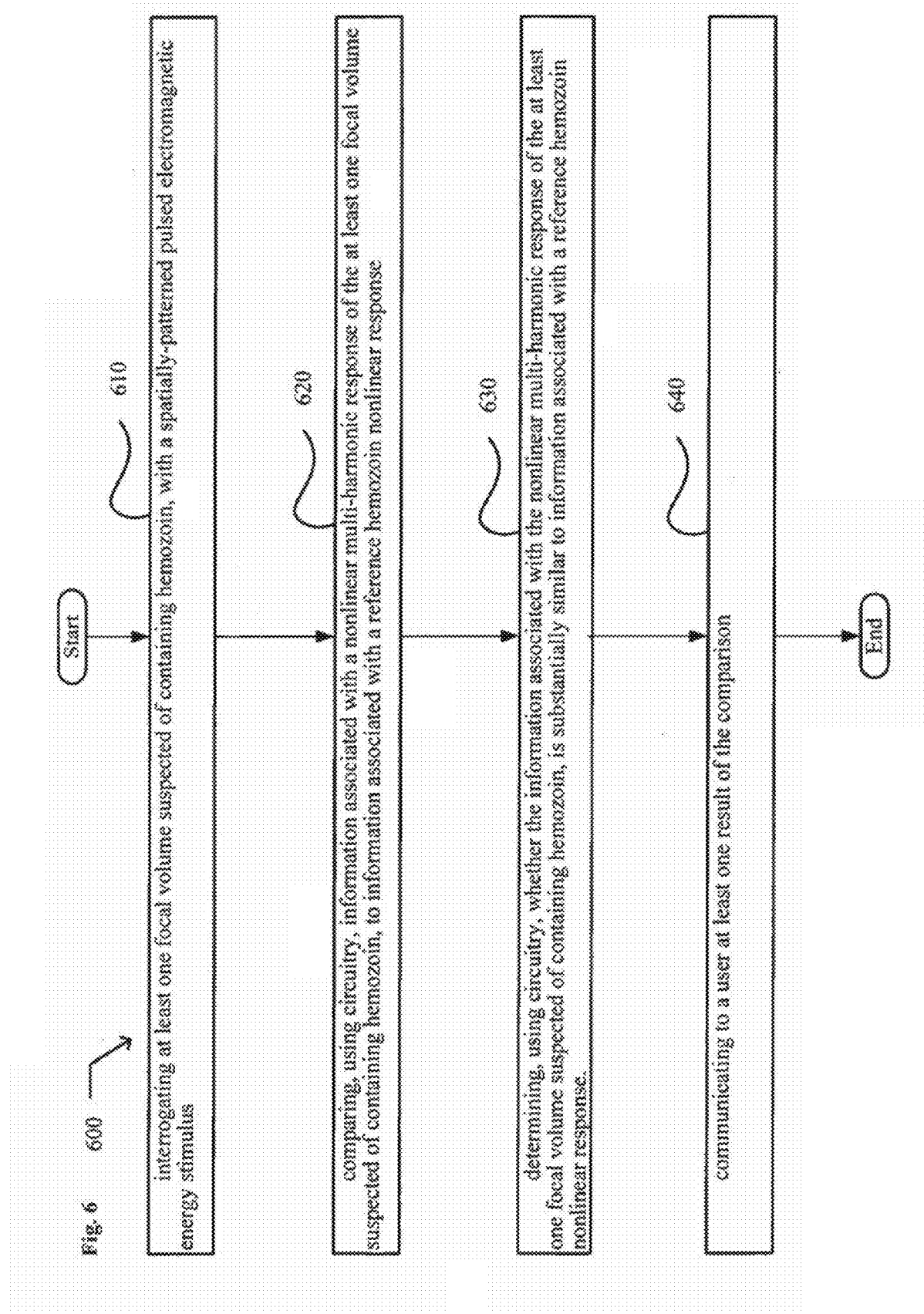
FIG. 6 is a flow diagram of a method according to one embodiment.

FIG. 6 shows an example of a method 600. At 610, the method 600 includes interrogating at least one focal volume suspected of containing hemozoin, with a spatially-patterned pulsed electromagnetic energy stimulus. At 620, the method 600 can further include comparing, using circuitry, information associated with a nonlinear multi-harmonic response of the at least one focal volume suspected of containing hemozoin, to information associated with a reference hemozoin nonlinear response. At 630, the method 600 can further include determining, using circuitry, whether the information associated with the nonlinear multi-harmonic response of the at least one focal volume suspected of containing hemozoin, is substantially similar to information associated with a reference hemozoin nonlinear response. At 640, the method 600 can further include communicating to a user at least one result of the comparison.

FIG. 7 shows an example of a method 700. At 710, the method 700 includes eliciting a nonlinear multi-harmonic response from hemozoin nanoparticles in a biological tissue within a focal volume by interrogating the focal volume with a pulsed electromagnetic energy stimulus having a resolution [0.61*(peak emission wavelength/numerical aperture)] ranging from about 300 nanometers to about 10 micrometers. At 712, eliciting the nonlinear multi-harmonic response includes delivering a pulsed multiplexed electromagnetic energy stimulus to multiple focal volumes, the pulsed multiplexed electromagnetic energy stimulus of a character and for a duration sufficient to elicit a nonlinear multi-harmonic response from hemozoin nanoparticles present with the at least one focal volume. At 720, the method 700 can further include comparing, using circuitry, the nonlinear multi-harmonic response to reference hemozoin nonlinear response information configured as a physical data structure 424. At 722, comparing, using circuitry, the nonlinear multi-harmonic response to the reference hemozoin nonlinear response information includes comparing a detected second harmonic response to reference hemozoin second harmonic response information configured as a physical data structure 424. At 724, comparing, using circuitry, the nonlinear multi-harmonic response to the reference hemozoin nonlinear response information includes comparing a detected third harmonic response to reference hemozoin third harmonic response information configured as a physical data structure 424. At 726, comparing, using circuitry, the nonlinear multi-harmonic response to the reference hemozoin nonlinear response information includes comparing a detected fourth harmonic response to reference hemozoin fourth harmonic response information configured as a physical data structure 424.

At 730, the method 700 can further include generating a response based on the comparison of the nonlinear multi-harmonic response to the reference hemozoin nonlinear response information.

FIG. 8 shows an example of a method 800. At 810, the method 800 includes comparing, using circuitry, information associated with a nonlinear multi-harmonic response of at least one focal volume suspected of containing hemozoin, the at least one focal volume interrogated with a spatially-patterned pulsed electromagnetic energy stimulus, to information associated with a reference hemozoin nonlinear multi-harmonic response.

FIG. 9 shows an example of an in situ method 900. At 910, the method 900 includes detecting, via one or more sensors 442, non-linear multi-harmonic response information associated with multiple focal volumes interrogated with a spatially-patterned pulsed electromagnetic energy stimulus. At 920, the method 900 can includes determining whether the detected non-linear multi-harmonic response information associated with the multiple focal volumes interrogated with the spatially-patterned pulsed electromagnetic energy stimulus satisfies threshold criteria associated with an absence, presence, or severity of hemozoin nanoparticles in a biological tissue. At 930, the method 900 can further includes generating a response in response to determining whether the detected non-linear multi-harmonic response information associated with the multiple focal volumes interrogated with the spatially-patterned pulsed electromagnetic energy stimulus satisfies threshold criteria associated with the presence of hemozoin nanoparticles in a biological tissue.

Figure 10:
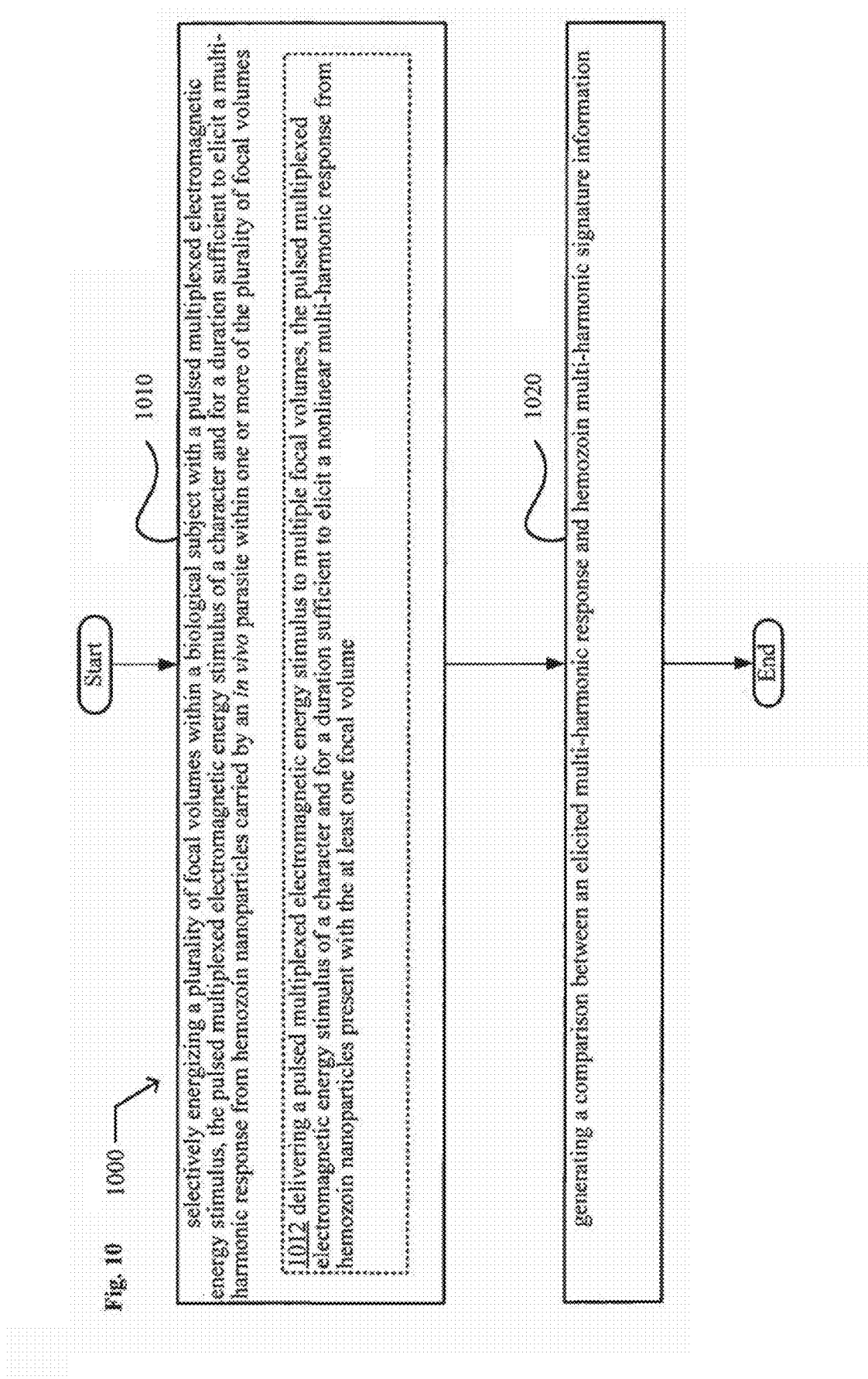
FIG. 10 is a flow diagram of a method according to one embodiment.

FIG. 10 shows an example of a method 1000. At 1010, the method 1000 includes selectively energizing a plurality of focal volumes within a biological subject with a pulsed multiplexed electromagnetic energy stimulus, the pulsed multiplexed electromagnetic energy stimulus of a character and for a duration sufficient to elicit a multi-harmonic response from hemozoin nanoparticles carried by a parasite within one or more of the plurality of focal volumes. At 1012, selectively energizing the plurality of focal volume includes delivering a pulsed electromagnetic energy stimulus of a character and for a duration sufficient to elicit one or more of a second harmonic response, a third harmonic response, or a fourth harmonic response from hemozoin nanoparticles carried by a parasite. At 1020, the method 1000 includes generating a comparison between an elicited multi-harmonic response or hemozoin multi-harmonic signature information.

FIG. 11 shows an example of a method 1100. At 1110, the method 1100 includes concurrently generating a multi-mode dark-field interrogation stimulus and a magnetic field stimulus. At 1120, the method 1100 includes detecting a scattering response associated with a plurality of hemozoin nanoparticles interrogated by the multiplexed dark-field interrogation stimulus in the presence of the magnetic field. At 1130, the method 1100 can further include varying a direction of the magnetic field stimulus. At 1140, the method 1100 can further include detecting scattering response associated with the plurality of hemozoin nanoparticles interrogated by the multiplexed dark-field interrogation stimulus in the presence of the varying magnetic field. At 1150, the method 1100 can further include varying a strength of the magnetic field stimulus.

At 1160, the method 1100 can further include detecting a scattering response associated with the plurality of hemozoin nanoparticles interrogated by the multiplexed dark-field interrogation stimulus in the presence of the varying magnetic field. At 1162, detecting the scattering response includes detecting a polarization of emerging scattering information. At 1164, detecting the scattering response includes detecting at least one of a diffracted, a reflected, or a refracted light associated with the plurality of hemozoin nanoparticles interrogated by the multiplexed dark-field interrogation stimulus in the presence of the magnetic field.

FIG. 12 shows an example of a method 1200. At 1210, the method 1200 includes concurrently generating a multi-mode dark-field interrogation stimulus of a character and for a duration sufficient to elicit a dark-field scattering response from hemozoin nanoparticles in a biological tissue and a magnetic field stimulus of a character and for a duration sufficient to magnetically align hemozoin nanoparticles in a biological tissue.

At 1220, the method 1200 includes detecting scattered electromagnetic radiation associated with a plurality of target regions within a biological subject interrogated by the multiplexed dark-field interrogation stimulus in the presence of the magnetic field stimulus.

FIG. 13 shows an example of a method 1300 of heat-shocking a plasmodium parasite. At 1310, the method 1300 includes delivering a time varying magnetic field energy to the biological subject, the time varying magnetic field energy sufficient to cause hemozoin nanoparticles in the plasmodium parasite to generate thermal energy.

Figure 14:
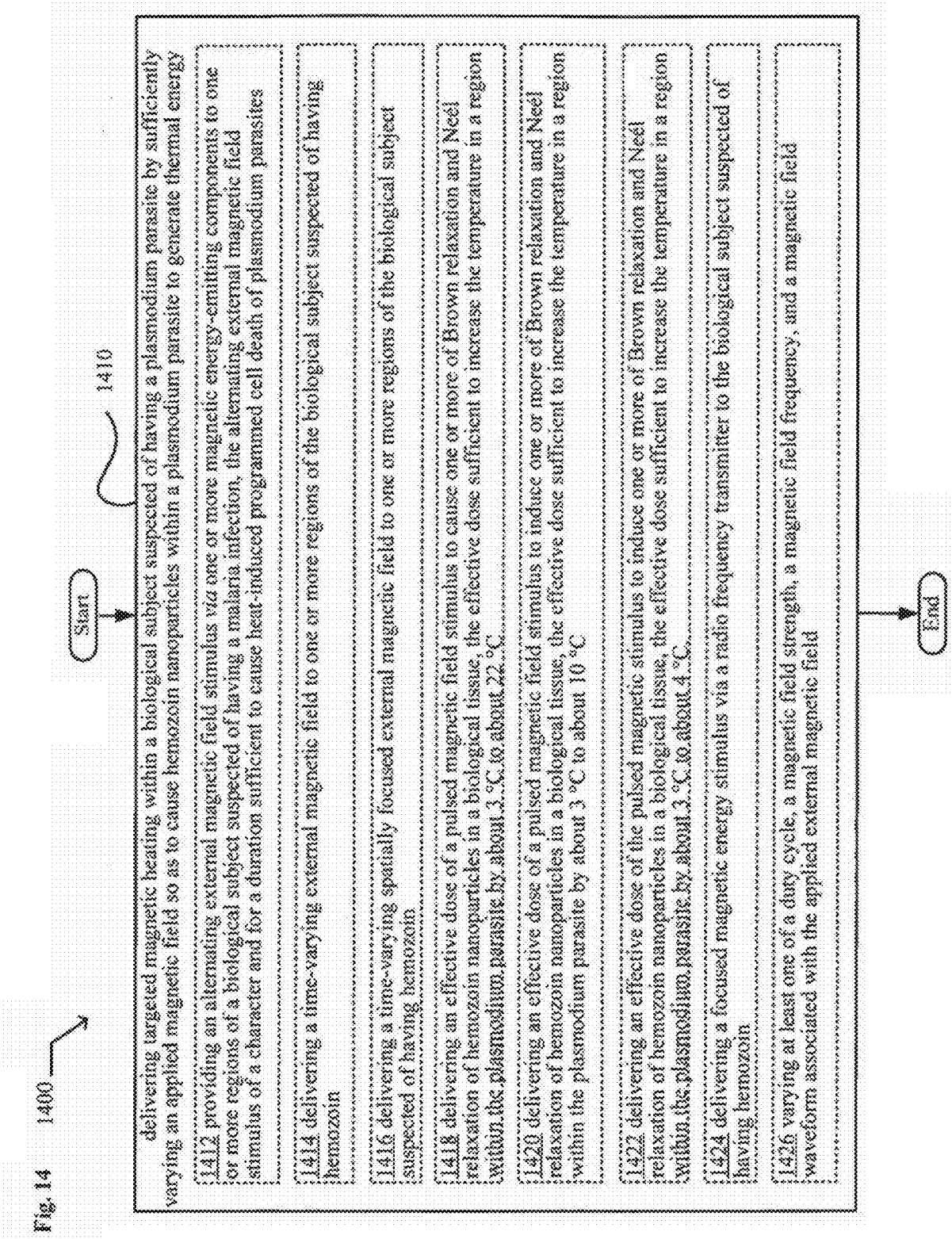
FIG. 14 is a flow diagram of a method according to one embodiment.

FIG. 14 shows an example of a method 1400 of treating a biological subject suspected of being infected with a plasmodium parasite. At 1410, the method 1400 includes delivering targeted magnetic heating within a biological subject suspected of having a plasmodium parasite by sufficiently varying an applied magnetic field so as to cause hemozoin nanoparticles within a plasmodium parasite to generate thermal energy. At 1412, delivering the targeted magnetic heating includes providing an alternating external magnetic field stimulus via one or more magnetic energy-emitting components to one or more regions of a biological subject suspected of having a malaria infection, the alternating external magnetic field stimulus of a character and for a duration sufficient to cause heat-induced programmed cell death of plasmodium parasites. At 1414, delivering the targeted magnetic heating includes delivering a time-varying external magnetic field to one or more regions of the biological subject suspected of having hemozoin. At 1416, delivering the targeted magnetic heating includes delivering a time-varying spatially focused external magnetic field to one or more regions of the biological subject suspected of having hemozoin. At 1418, delivering the targeted magnetic heating includes delivering an effective dose of a pulsed magnetic field stimulus to cause one or more of Brown relaxation and Neíl relaxation of hemozoin nanoparticles in a biological tissue, the effective dose sufficient to increase the temperature in a region within the plasmodium parasite by about 3° C. to about 22° C. At 1420, delivering the targeted magnetic heating includes delivering an effective dose of a pulsed magnetic field stimulus to induce one or more of Brown relaxation and Neél relaxation of hemozoin nanoparticles in a biological tissue, the effective dose sufficient to increase the temperature in a region within the plasmodium parasite by about 3° C. to about 10° C. At 1422, delivering the targeted magnetic heating includes delivering an effective dose of the pulsed magnetic stimulus to induce one or more of Brown relaxation and Neél relaxation of hemozoin nanoparticles in a biological tissue, the effective dose sufficient to increase the temperature in a region within the plasmodium parasite by about 3° C. to about 4° C. At 1424, delivering the targeted magnetic heating includes delivering a focused magnetic energy stimulus via a radio frequency transmitter to the biological subject suspected of having hemozoin. At 1426, delivering the targeted magnetic heating includes varying at least one of a duty cycle, a magnetic field strength, a magnetic field frequency, or a magnetic field waveform associated with the applied external magnetic field.

FIG. 15 shows an example of a method 1500 of enhancing a Brownian or Neelian process of a hemozoin nanoparticle. At 1510, the method 1500 includes comparing, using circuitry, (a) a nonlinear multi-harmonic response profile information associated with at least one focal volume interrogated with a spatially patterned pulsed electromagnetic energy stimulus to (b) a reference hemozoin nonlinear response information. At 1520, the method 1500 includes applying a varying magnetic field to the at least one focal volume, the varying magnetic field energy sufficient to cause hemozoin nanoparticles to at least one of oscillate, a translate, or a rotate.

FIG. 16 shows an example of a method 1600 of method of treating a plasmodium parasitic infection. At 1610, the method 1600 includes comparing, using circuitry, (a) a nonlinear multi-harmonic response profile information associated with at least one focal volume interrogated with a spatially patterned pulsed electromagnetic energy stimulus to (b) a reference hemozoin nonlinear response information. At 1620, the method 1600 includes magnetically inducing at least one of an oscillation, a translation, or a rotation of hemozoin nanoparticles in the at least one focal volume. At 1622, magnetically inducing the at least one of the oscillation, the translation, and the rotation of hemozoin nanoparticles in the at least one focal volume includes energizing one or more conductive coils for a duration sufficient to generate a time-varying magnetic field of a character and for a duration sufficient to cause hemozoin nanoparticles to at least one of oscillate, translate, and rotate. At 1624, magnetically inducing the at least one of the oscillation, the translation, and the rotation of hemozoin nanoparticles in the at least one focal volume includes delivering an effective dose of a pulsed magnetic field stimulus to affect the integrity of an organelle of a malarial infectious agent based in part on the comparison of the nonlinear multi-harmonic response profile associated with the at least one focal volume to the reference hemozoin nonlinear response information. At 1626, magnetically inducing the at least one of the oscillation, the translation, and the rotation of hemozoin nanoparticles in a biological tissue includes providing a radio frequency coil assembly an effective amount of an applied current, the effective amount of an applied current of a character and for a duration sufficient to generate a magnetic field of a character and for a duration sufficient to cause one or more of oscillation, translation, and rotation of hemozoin nanoparticles in a biological tissue. At 1628, magnetically inducing the at least one of the oscillation, the translation, and the rotation of hemozoin nanoparticles in a biological tissue includes delivering an effective dose of a pulsed magnetic field stimulus to cause one or more of oscillation, translation, and rotation of hemozoin nanoparticles in a biological tissue. At 1630, magnetically inducing the at least one of the oscillation, the translation, and the rotation of hemozoin nanoparticles in a biological tissue includes delivering an effective dose of an electromagnetic energy stimulus to cause one or more of oscillation, translation, and rotation of hemozoin nanoparticles in a biological tissue.

FIG. 17 shows an example of a method 1700. At 1710, the method 1700 includes generating a comparison between (a) a detected scattering profile information associated with a plurality of target regions within a biological tissue interrogated by a dark-field interrogation stimulus in the presence of a magnetic field stimulus and (b) reference hemozoin dark field scattering information. At 1712, generating the comparison includes comparing, using circuitry, a detected scattering profile associated with a plurality of target regions within a biological subject interrogated by a multiplexed dark-field interrogation stimulus in the presence of a magnetic field stimulus and reference hemozoin dark field scattering information. At 1714, generating the comparison includes comparing, using circuitry, a detected scattering profile obtained using a Rheinberg illumination configuration in the presence of a magnetic field stimulus and reference hemozoin Rheinberg illumination spectral information.

At 1720, the method 1700 includes magnetically perturbing hemozoin nanoparticles in the biological tissue based in part on the comparison. At 1722, magnetically perturbing the hemozoin nanoparticles in a biological tissue includes applying a magnetic field stimulus of a character and for a duration sufficient to cause the hemozoin nanoparticles in a biological tissue to affect the integrity of a digestive food vacuole of a malaria parasite. At 1724, magnetically perturbing the hemozoin nanoparticles in a biological tissue includes applying an alternating magnetic field stimulus of a character and for a duration sufficient to cause the hemozoin nanoparticles in a biological tissue to rupture a membrane of a digestive food vacuole of a malaria parasite. At 1726, magnetically perturbing the hemozoin nanoparticles in a biological tissue includes applying a time-varying magnetic field stimulus of a character and for a duration sufficient to cause a reduction in a parasitemia level.

FIG. 18 shows an example of a method 1800 for modulating plasmodium parasitic activity. At 1810, the method 1800 includes eliciting a nonlinear multi-harmonic response from hemozoin nanoparticles in a biological tissue by interrogating a plurality of focal volumes with a pulsed electromagnetic energy stimulus having a peak irradiance of less than about 200 gigawatts/cm^2 and having at least one peak emission wavelength ranging from about 690 nanometers to about 2100 nanometers, the pulsed electromagnetic energy stimulus of a character and for a duration sufficient to modulate a biological activity of a malarial infectious agent. At 1812, eliciting the nonlinear multi-harmonic response from hemozoin nanoparticles in a biological tissue includes irradiating hemozoin nanoparticles in a biological tissue within one or more of the plurality of focal volumes with electromagnetic energy having a peak emission wavelength ranging from about 1000 nanometers to about 1300 nanometers. At 1814, eliciting the nonlinear multi-harmonic response from hemozoin nanoparticles in a biological tissue includes irradiating hemozoin nanoparticles in a biological tissue within one or more of the plurality of focal volumes with electromagnetic energy having a peak emission wavelength ranging from about 1000 nanometers to about 1080 nanometers. At 1816, eliciting the nonlinear multi-harmonic response from hemozoin nanoparticles in a biological tissue includes irradiating hemozoin nanoparticles in a biological tissue within one or more of the plurality of focal volumes with electromagnetic energy having a peak emission wavelength ranging from about 1012 nanometers to about 1060 nanometers. At 1818, eliciting the nonlinear multi-harmonic response from hemozoin nanoparticles in a biological tissue includes irradiating hemozoin nanoparticles in a biological tissue within one or more of the plurality of focal volumes with electromagnetic energy having a peak emission wavelength of about 1040 nanometers. At 1820, eliciting the nonlinear multi-harmonic response from hemozoin nanoparticles in a biological tissue includes irradiating hemozoin nanoparticles in a biological tissue within one or more of the plurality of focal volumes with electromagnetic energy having a peak emission wavelength ranging from about 700 nanometers to about 870 nanometers. At 1822, eliciting the nonlinear multi-harmonic response from hemozoin nanoparticles in a biological tissue includes irradiating hemozoin nanoparticles in a biological tissue within one or more of the plurality of focal volumes with electromagnetic energy having a peak emission wavelength ranging from about 750 nanometers to about 810 nanometers. At 1824, eliciting the nonlinear multi-harmonic response from hemozoin nanoparticles in a biological tissue includes irradiating hemozoin nanoparticles in a biological tissue within one or more of the plurality of focal volumes with electromagnetic energy having a peak emission wavelength ranging from about 760 nanometers to about 780 nanometers. At 1826, eliciting the nonlinear multi-harmonic response from hemozoin nanoparticles in a biological tissue includes irradiating hemozoin nanoparticles in a biological tissue within one or more of the plurality of focal volumes with electromagnetic energy having a peak emission wavelength of about 780 nanometers. At 1828, eliciting the nonlinear multi-harmonic response from hemozoin nanoparticles in a biological tissue includes irradiating the hemozoin nanoparticles in a biological tissue within one or more of the plurality of focal volumes with electromagnetic energy of a character and for a duration to cause a portion of the hemozoin nanoparticles in a biological tissue to generate a nonlinear multi-harmonic response having a wavelength ranging from about 233 nanometers to about 434 nanometers. At 1830, eliciting the nonlinear multi-harmonic response from hemozoin nanoparticles in a biological tissue includes irradiating the hemozoin nanoparticles in a biological tissue within one or more of the plurality of focal volumes with electromagnetic energy of a character and for a duration to cause a portion of the hemozoin nanoparticles in a biological tissue to generate a nonlinear multi-harmonic response having a wavelength ranging from about 175 nanometers to about 325 nanometers.

At 1832, eliciting the nonlinear multi-harmonic response from hemozoin nanoparticles in a biological tissue includes irradiating the hemozoin nanoparticles in a biological tissue within one or more of the plurality of focal volumes with electromagnetic energy of a character and for a duration to cause a portion of the hemozoin nanoparticles in a biological tissue to generate a nonlinear multi-harmonic response having a wavelength ranging from about 175 nanometers to about 290 nanometers. At 1834, eliciting the nonlinear multi-harmonic response from hemozoin nanoparticles in a biological tissue includes eliciting one or more of a second harmonic response, a third harmonic response, or a fourth harmonic response by interrogating the hemozoin nanoparticles in a biological tissue with a pulsed electromagnetic energy stimulus, the elicited one or more of the second harmonic response, the third harmonic response, and the fourth harmonic response of a character and for a duration sufficient to induce programmed cell death of an infectious agent. At 1836, eliciting the nonlinear multi-harmonic response from hemozoin nanoparticles in a biological tissue includes eliciting one or more of a second harmonic response, a third harmonic response, or a fourth harmonic response by interrogating the hemozoin nanoparticles in a biological tissue with a pulsed electromagnetic energy stimulus, the elicited one or more of the second harmonic response, the third harmonic response, and the fourth harmonic response of a character and for a duration sufficient to induce apoptosis of a host cell carrying an infectious agent. At 1838, eliciting the nonlinear multi-harmonic response from hemozoin nanoparticles in a biological tissue includes applying an electromagnetic energy stimulus of a sufficient strength and duration to elicit the hemozoin nanoparticles in a biological tissue within a biological sample to generate antimicrobial energy. At 1840, eliciting the nonlinear multi-harmonic response from hemozoin nanoparticles in a biological tissue includes applying an electromagnetic energy stimulus of a sufficient strength and duration to cause a nonlinear multi-harmonic response of a character and for a duration sufficient to inhibit proliferation of a malarial infectious agent. At 1842, eliciting the nonlinear multi-harmonic response from hemozoin nanoparticles in a biological tissue includes irradiating hemozoin nanoparticles in a biological tissue within one or more of the plurality of focal volumes with electromagnetic energy having a resolution [0.61*(peak emission wavelength/numerical aperture)] ranging from about 300 nanometers to about 10 micrometers.

Figure 19:
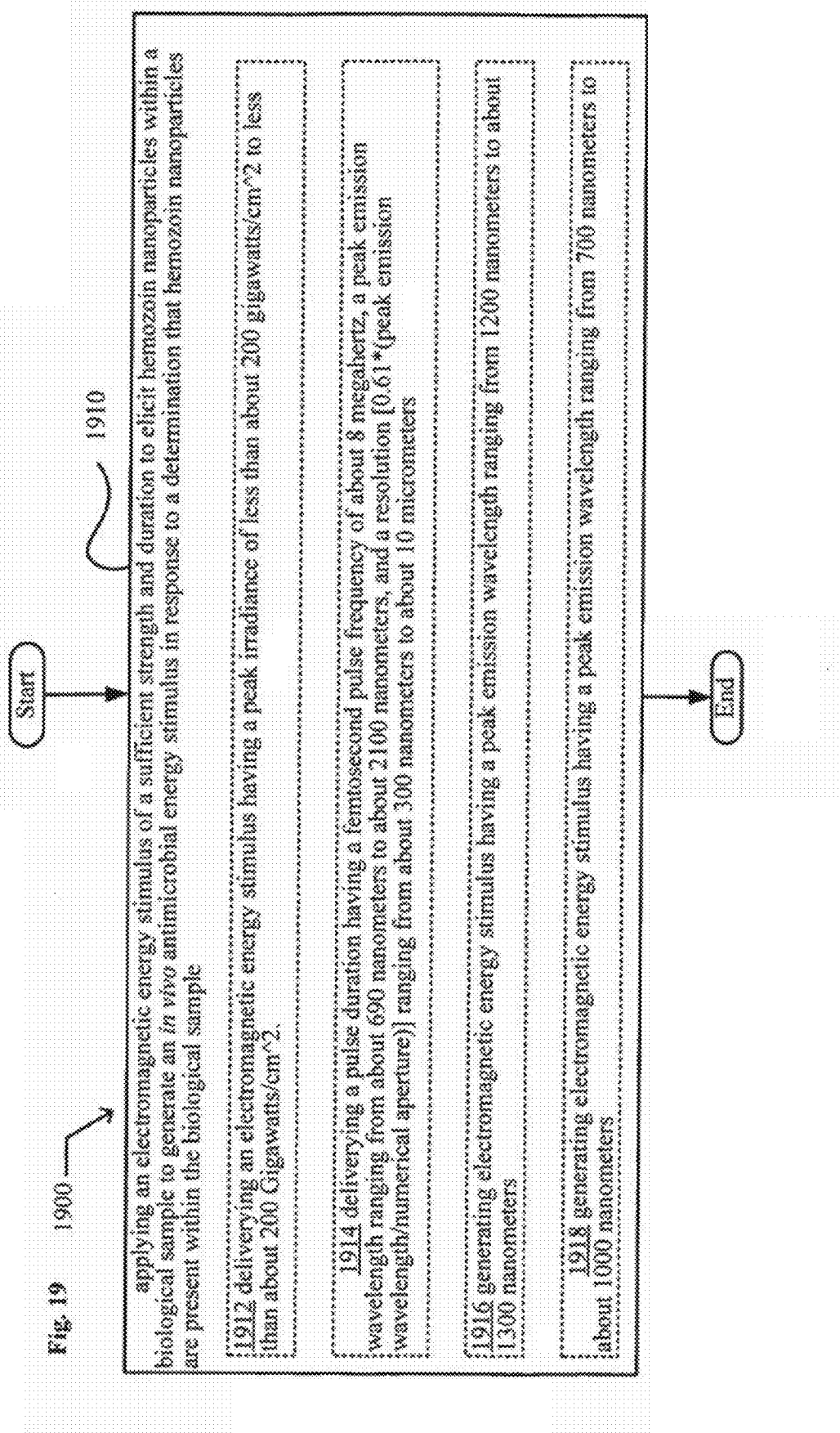
FIG. 19 is a flow diagram of a method according to one embodiment.

FIG. 19 shows an example of an anti-malarial therapeutic method 1900. At 1910, the method 1900 includes applying an electromagnetic energy stimulus of a sufficient strength and duration to elicit hemozoin nanoparticles within a biological sample to generate an in vivo antimicrobial energy stimulus in response to a determination that hemozoin nanoparticles are present within the biological sample. At 1912, applying the electromagnetic energy stimulus includes deliverying an electromagnetic energy stimulus having a peak irradiance of less than about 200 gigawatts/cm$^2$ to less than about 200 Gigawatts/cm$^2$. At 1914, applying the electromagnetic energy stimulus includes deliverying a pulse duration having a femtosecond pulse frequency of about 8 megahertz, a peak emission wavelength ranging from about 690 nanometers to about 2100 nanometers, and a resolution [0.61*(peak emission wavelength/numerical aperture)] ranging from about 300 nanometers to about 10 micrometers. At 1916, applying the electromagnetic energy stimulus includes generating electromagnetic energy stimulus having a peak emission wavelength ranging from 1200 nanometers to about 1300 nanometers. At 1918, applying the electromagnetic energy stimulus includes generating electromagnetic energy stimulus having a peak emission wavelength ranging from 700 nanometers to about 1000 nanometers.

At least a portion of the devices and/or processes described herein can be integrated into a data processing system. A data processing system generally includes one or more of a system unit housing, a video display device, memory such as volatile or non-volatile memory, processors 404 such as microprocessors or digital signal processors, computational entities such as operating systems, drivers, graphical user interfaces, and applications programs, one or more interaction devices (e.g., a touch pad, a touch screen, an antenna, etc.), and/or control systems including feedback loops and control motors (e.g., feedback for detecting position and/or velocity, control motors for moving and/or adjusting components and/or quantities). A data processing system may be implemented utilizing suitable commercially available components, such as those typically found in data computing/communication and/or network computing/communication systems.

As shown in Example 1, nonlinear optical response information, spectral information, or the like associated with for example, hemozoin nanoparticles can be determined by one or more in vivo or in vitro technologies or methodologies.

EXAMPLE 1

In vitro Analysis of Hemozoin Nanoparticles

A method is described for detecting nonlinear multi-harmonic response energy properties of materials having hemozoin nanoparticles. For this analysis, synthetic hemozoin crystals were crushed into a fine powder and suspended with isopropanol in a volume ratio of five parts isopropanol to one part hemozoin crystals. A droplet of the hemozoin/isopropanol suspension was placed onto a quartz cover slip (0.25 mm thickness) and the isopropanol allowed to evaporate to generate a thin-film of hemozoin. The hemozoin thin-film was further heated at 70° C. for one minute to eliminate any residual condensation. The integrity and distribution of hemozoin crystals in the hemozoin thin-film were assessed at a magnification ranging from 20× to 100×. Crystals observed in the hemozoin thin-film ranged in size from under 1 micron to about 10-20 microns.

Figure 20:
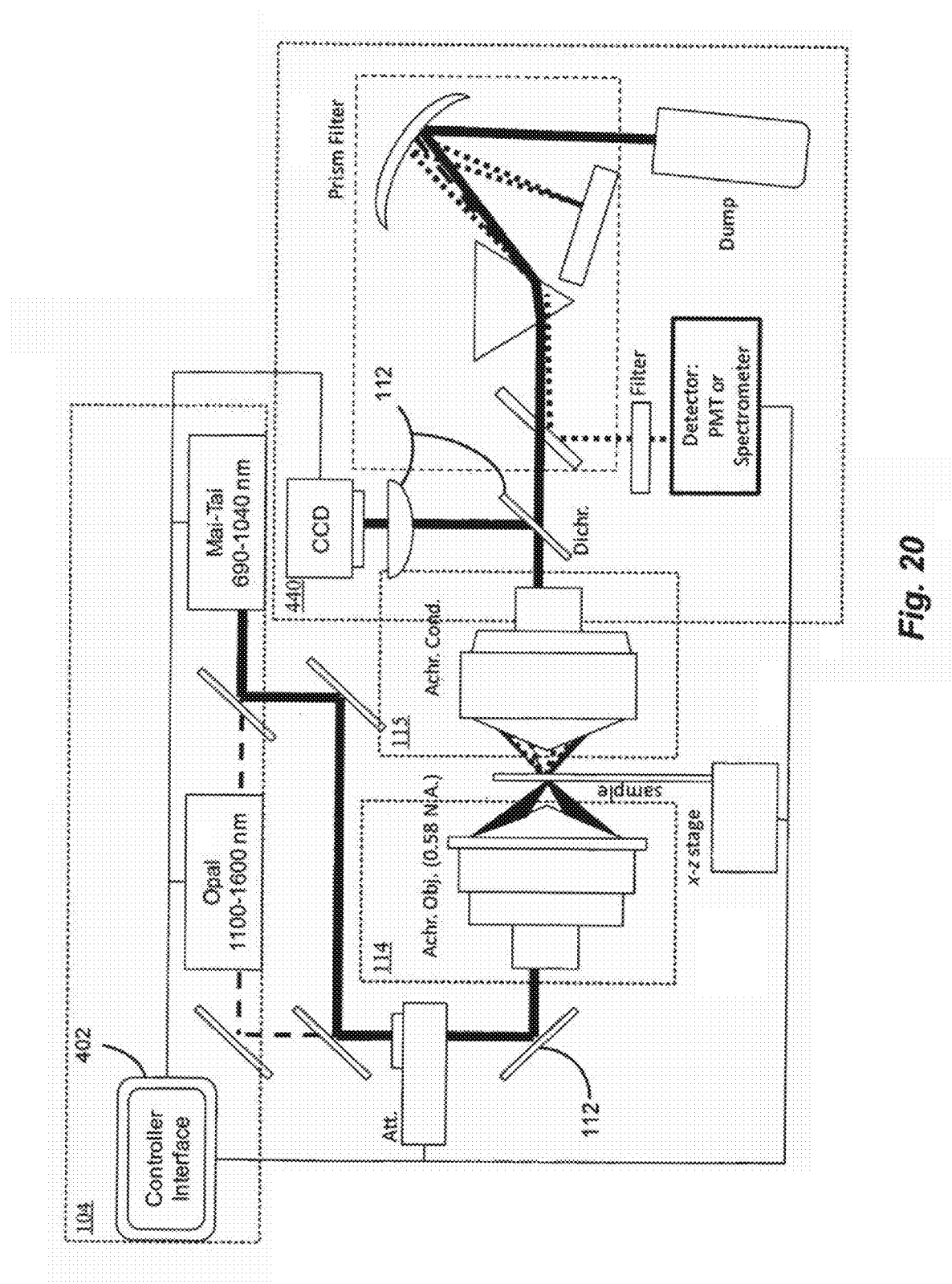
FIG. 20 is a perspective view of a monitor or treatment device configuration according to one embodiment.

The hemozoin thin-film was exposed to a pulsed electromagnetic energy stimulus to elicit a nonlinear optical response from the hemozoin nanoparticles using the experimental configuration outlined in FIG. 20. The experimental configuration provided for a pulsed electromagnetic energy stimulus in an overall range of 690 nm to 1600 nm using a Ti:Sapphire laser to scan wavelengths from 690-1040 nm and an optical parametric oscillator (OPO). The quartz cover slip containing the hemozoin thin-film was attached to a nanoscale positioning stage to allow scanning of the sample along the optical axis (z-scan) and along the lateral surface (lateral scan). The sample was placed between an achromatic objective (0.58 numerical aperture) and an achromatic condenser. A prism and filtering system were used as a spatial filter to cover peak emission wavelengths ranging from 175 nm to 650 nm. Non-linear multi-harmonic response energy from the hemozoin particles was detected using either a spectrometer or a photomultiplier tube. Various components of the experimental configuration were linked to a controller interface (e.g., computer) including the Ti:Sapphire laser, the OPO, the detector, and the nanoscale positioning stage.

Figure 21:
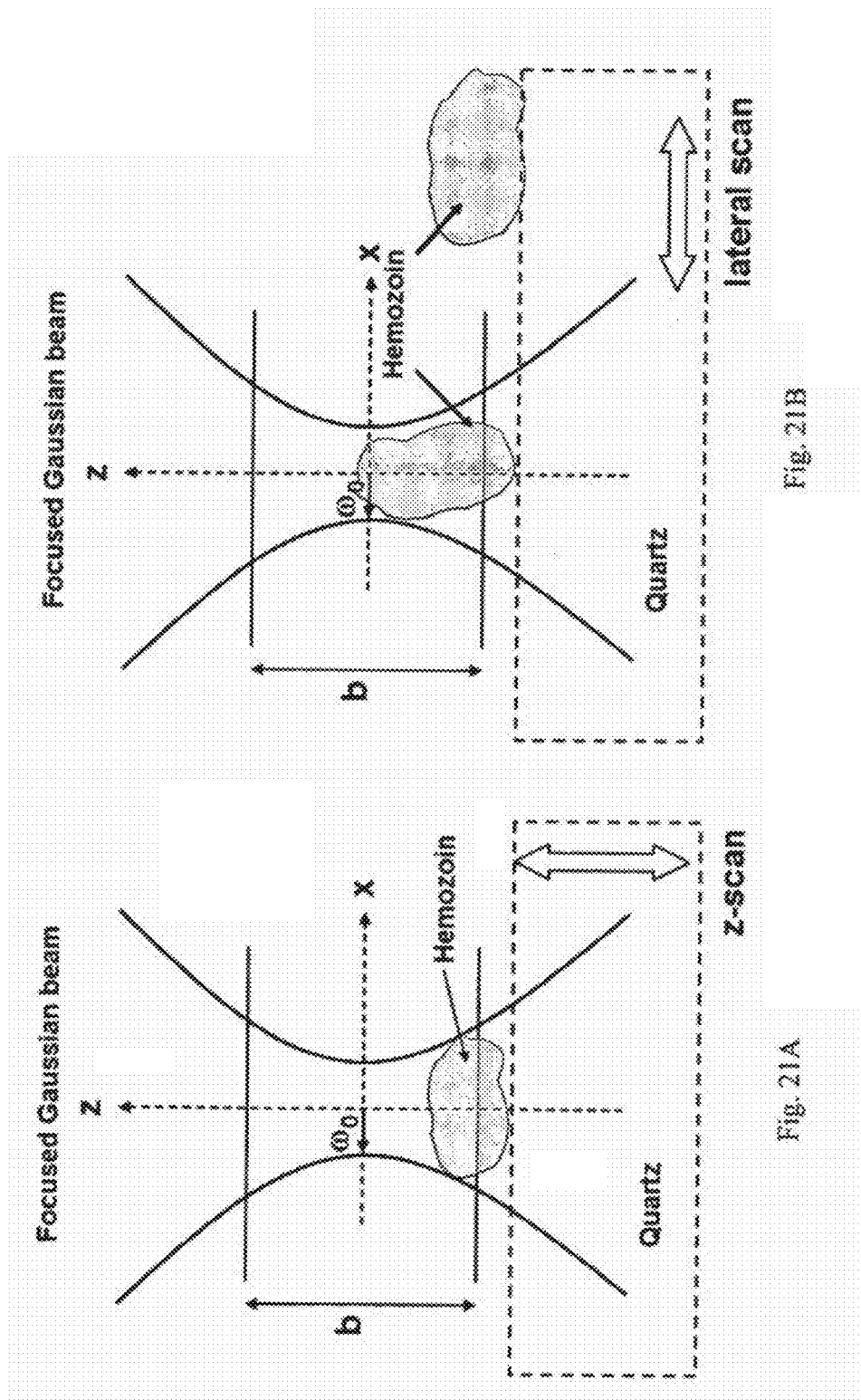
FIGS. 21A and 21B show top plan views of respective representative z-scan and lateral scans methodologies from hemozoin thin-films according to one embodiment.
Figure 22:
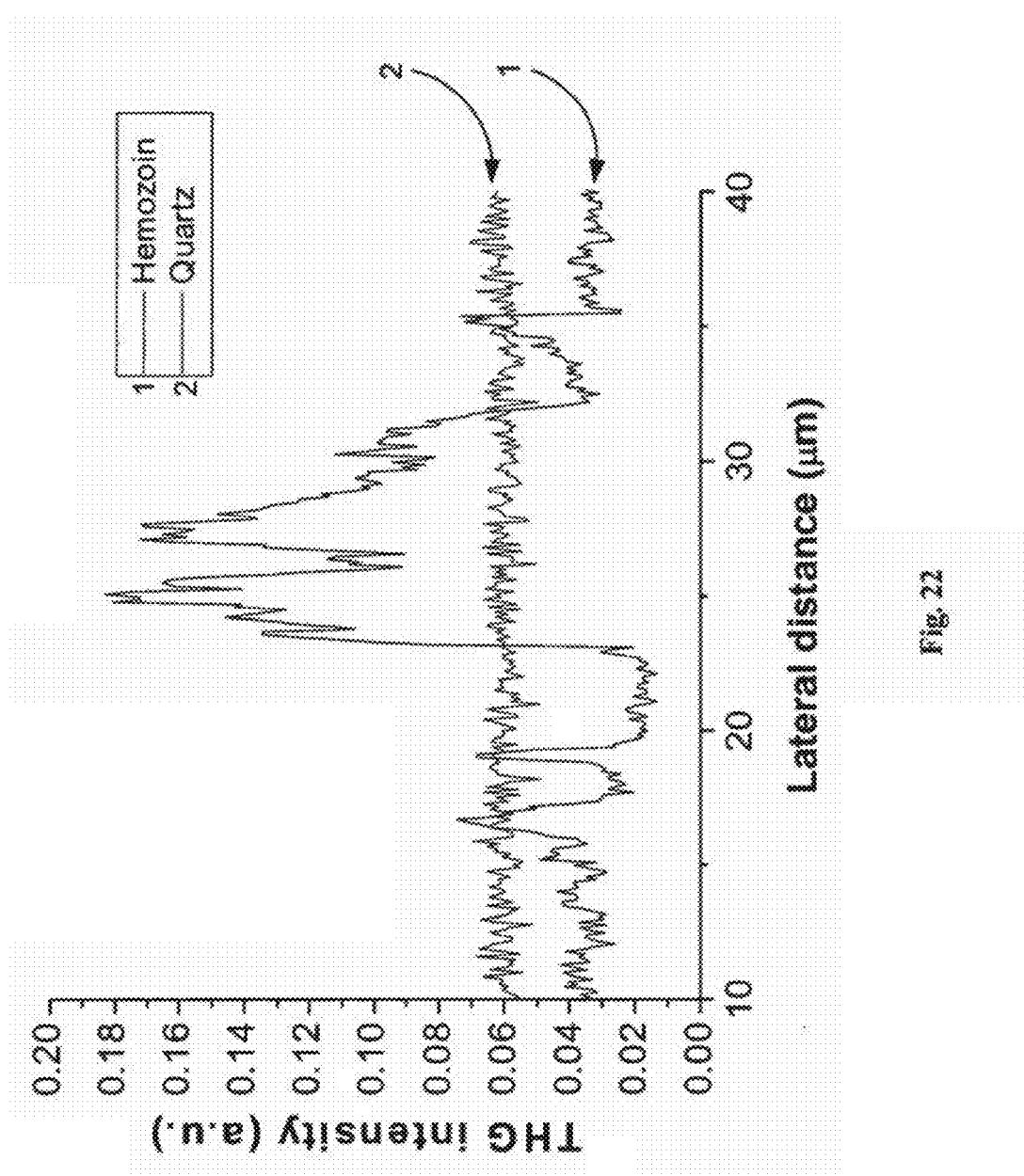
FIG. 22 Third Harmonic Generation (THG) Intensity vs. Lateral Distance plot of (1) hemozoin and (2) quartz according to one embodiment.

In one set of experiments designed to measure a third harmonic response, the hemozoin thin-film was scanned along the optical axis (z-scan) and through the focal volume of an excitation energy of 810 nm. In this instance, a 100× objective with a 0.9 numerical aperture was used. The third harmonic response energy and excitation light were collimated, passed through a UG-11 colored glass filter (transmits wavelengths of 250-350 nm and of 700-800 nm) and a 265 nm notch filter and sent to a photomultiplier tube. The anode current from the photomultiplier tube was directly measured with an electrometer, linearly converted to a voltage, and recorded on a computer via a data acquisition card. FIG. 21A shows a representative z-scan from the hemozoin thin-film using this methodology. Also shown is the control measurement of the quartz substrate. The width of the peak in both cases was less than 5 µm, consistent with a beam size of less than 800 nm (based on 100× objective and 0.9 numerical aperture). The magnitude of the hemozoin peak varied up to 20% depending on the size of the hemozoin crystal and the amount of the focal volume filled with hemozoin. A lateral scan (FIG. 21B) was also performed using the parameters described above by first performing a z-scan analysis to find a maximum third harmonic response and a lateral scan was performed at this z-position. FIG. 22 shows an example of the third harmonic response through a lateral scan (1) of the hemozoin thin-film relative to a lateral scan (2), through the quartz substrate The third harmonic response efficiency is inversely proportional to the square of the spot size ($A_{spot}^2$) and the square of the pulse width ($\tau^2$) and therefore it is important to monitor and minimize both of these variables. The focal volume of the pulsed electromagnetic energy stimulus was profiled using a standard knife-edge diffraction technique to measure the beam waist at several positions along the optical axis. An autocorrelater was used to measure the pulse-width of the beam. The third order dependence on power output from the pulsed electromagnetic energy stimulus was demonstrated by plotting the laser excitation power, $P(\omega)$ [mW] against the third harmonic response power, $P(3\omega)$ [arbitrary units] as shown in FIG. 23. A log-log scale plot of this data generated a line with a slope of approximately 3.

The herein described subject matter sometimes illustrates different components contained within, or connected with, different other components. It is to be understood that such depicted architectures are merely examples, and that in fact, many other architectures may be implemented that achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled," to each other to achieve the desired functionality, and any two components capable of being so associated can also be viewed as being "operably coupleable," to each other to achieve the desired functionality. Specific examples of operably coupleable include, but are not limited to, physically mateable and/or physically interacting components, and/or wirelessly interactable, and/or wirelessly interacting components, and/or logically interacting, and/or logically interactable components.

Figures 23A, 23B:
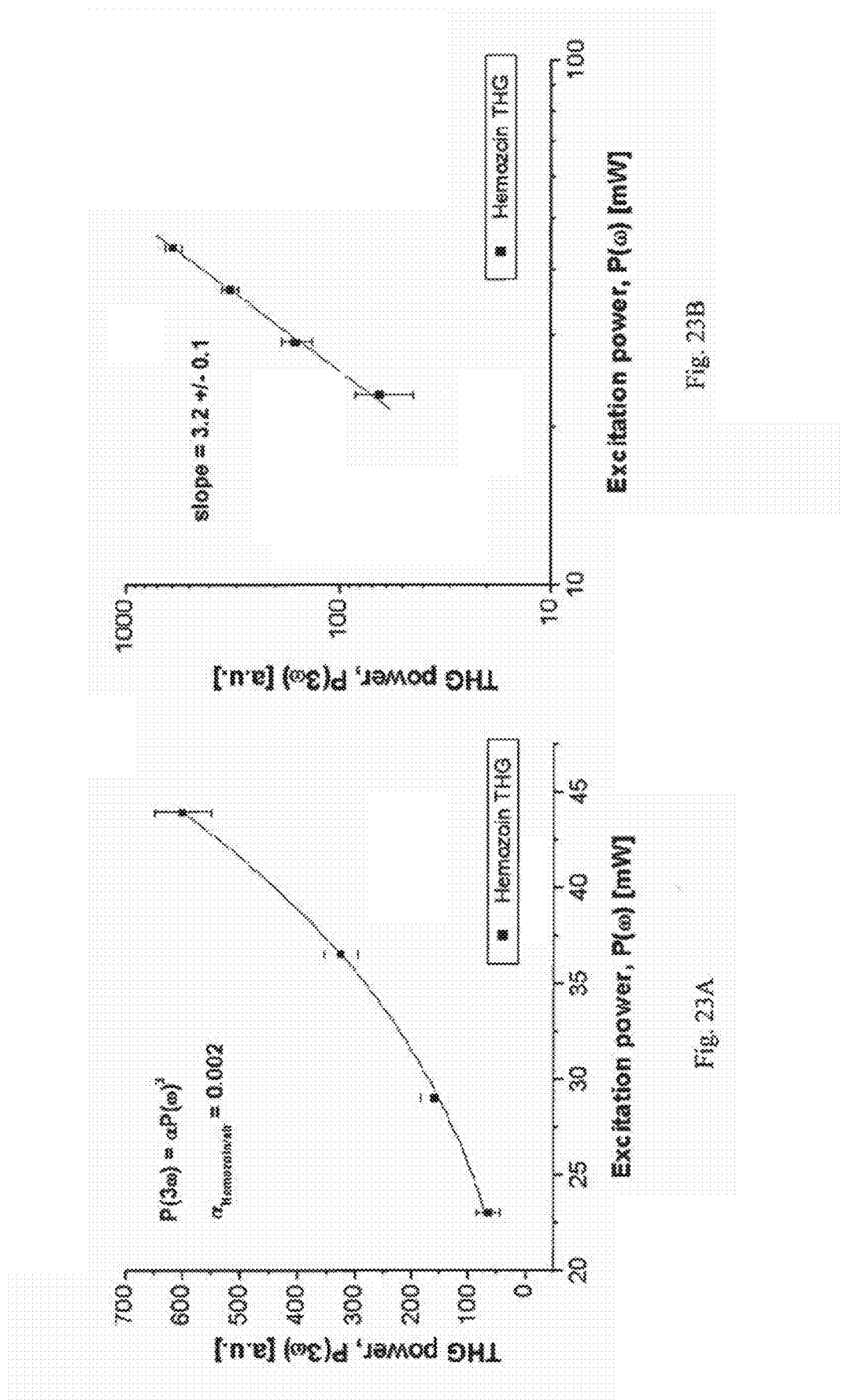
FIGS. 23A and 23B show Third Harmonic Generation (THG) Power vs. Excitation Power plots according to multiple illustrated embodiments.
Figure 24:
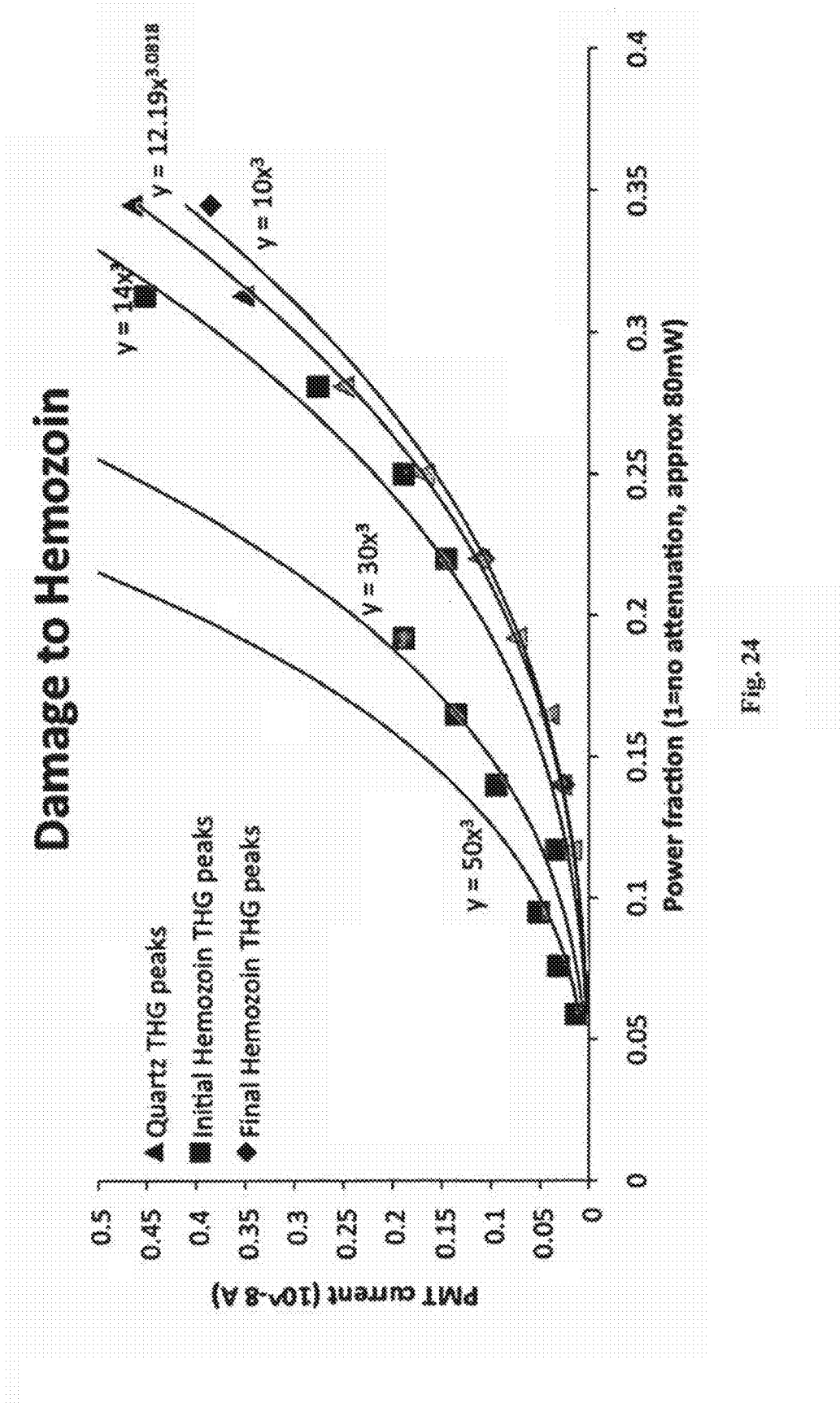
FIG. 24 is a Photo Multiplier Tube (PMT) current vs. Power Fraction plot according to one embodiment.
Figure 25:
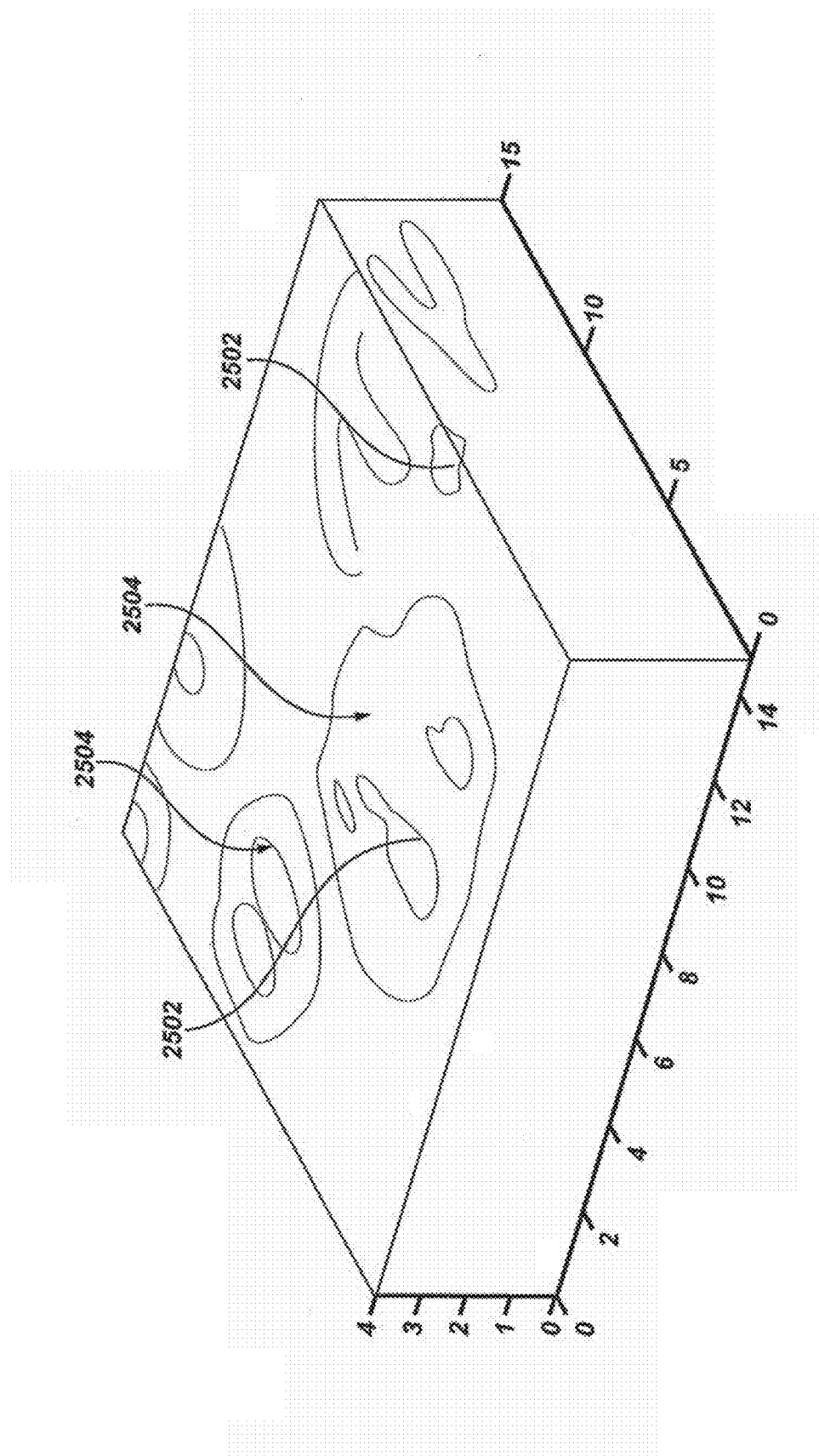
FIG. 25 is a voxel image of hemozoin crystals in infected red blood cells according to one embodiment.
Figure 26:
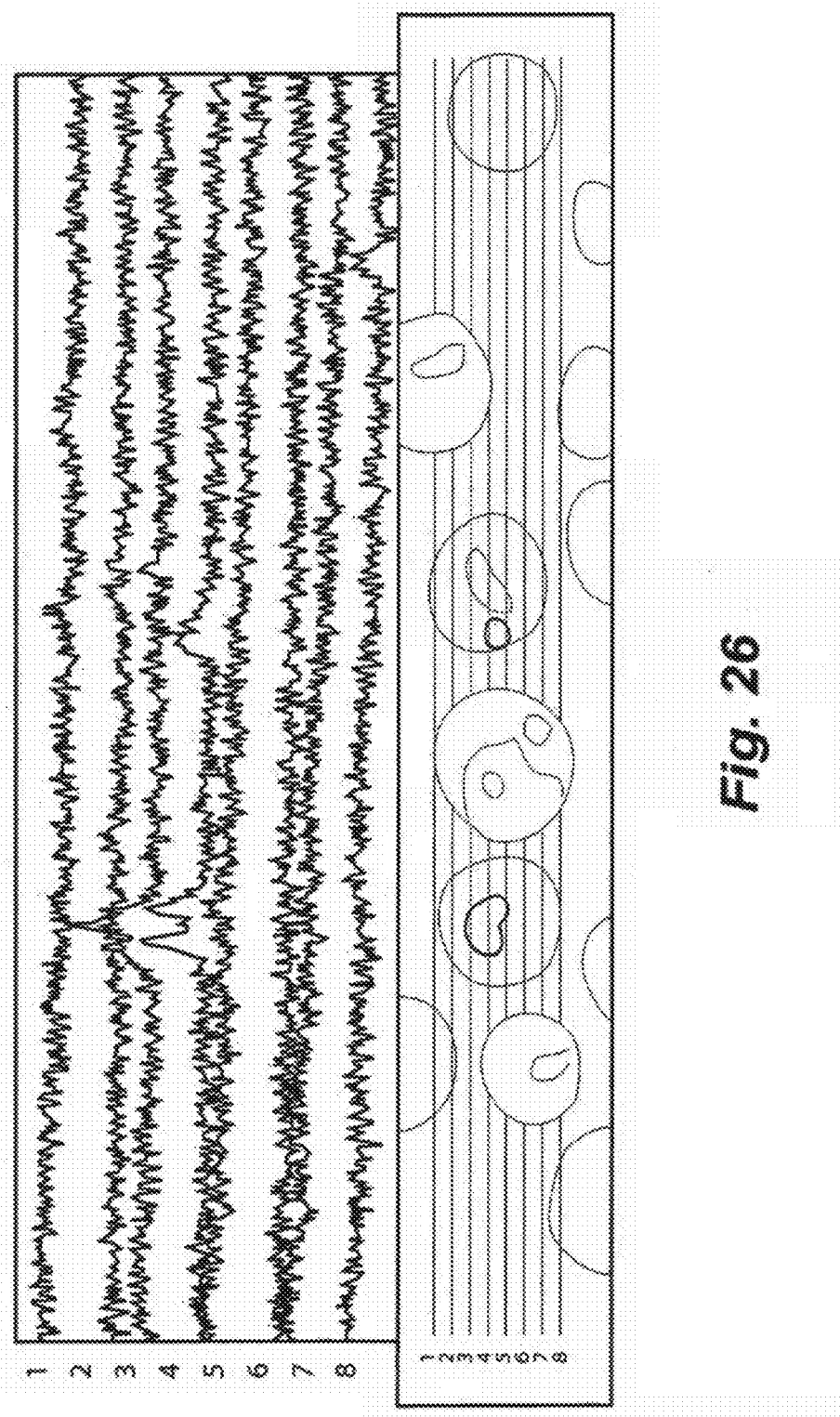
FIG. 26 is a two-dimensional spatial scan of infected and uninfected erythrocytes showing intensity peaks that correspond to hemozoin crystals in the infected cells, according to one embodiment.
Figure 27:
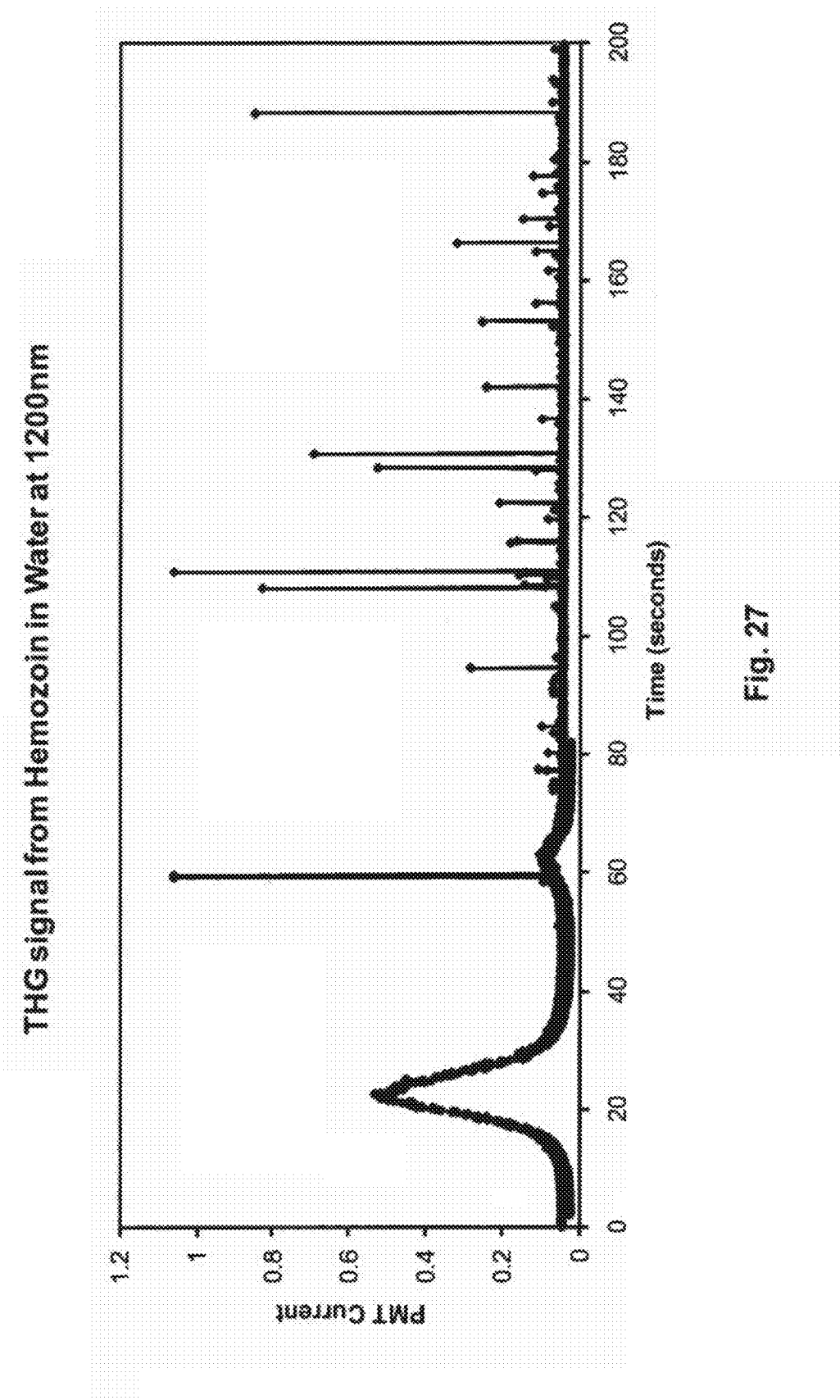
FIG. 27 is a Photo Multiplier Tube (PMT) current vs. Time plot according to one embodiment.
Figure 28:
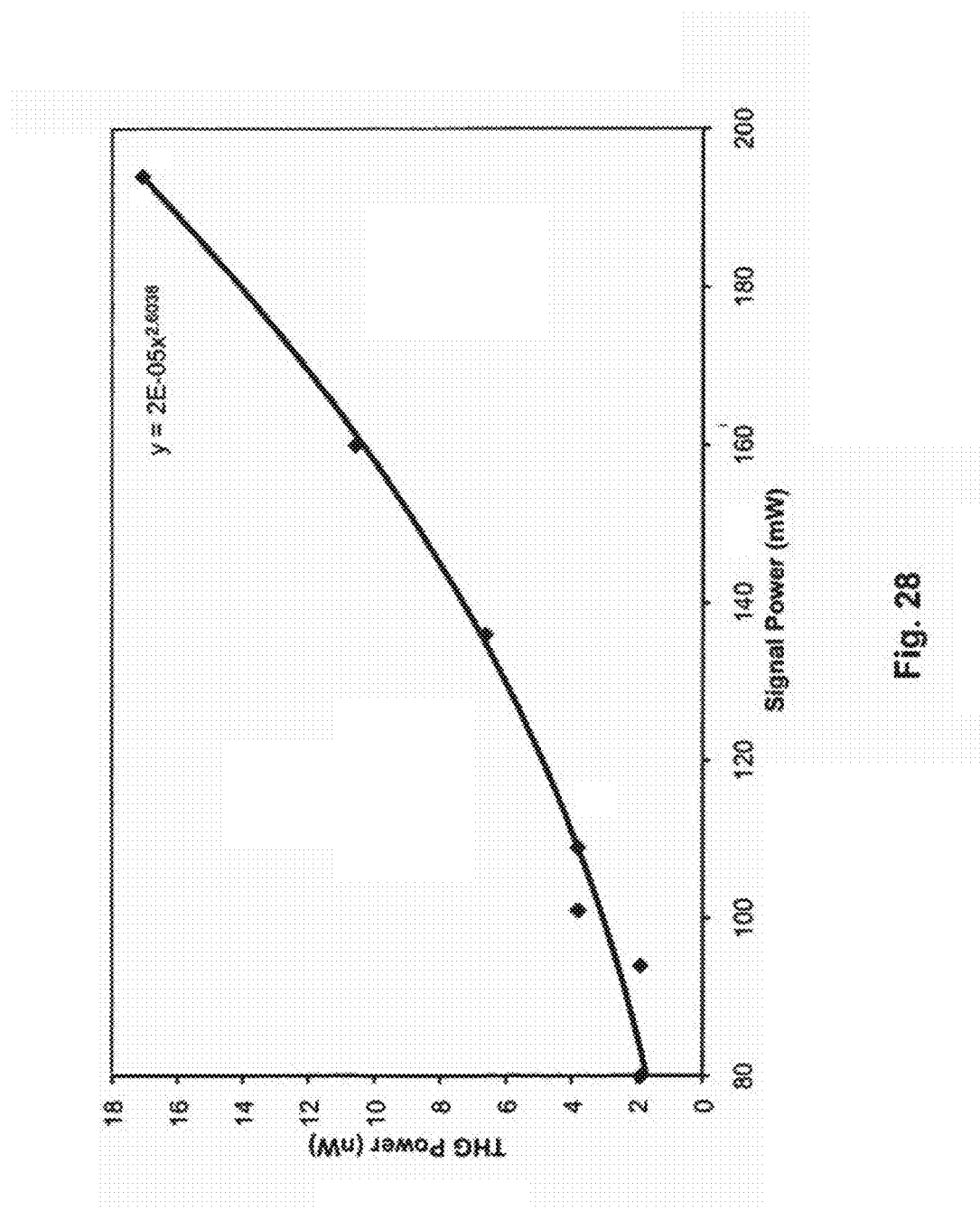
FIG. 28 is a Third Harmonic Generation (THG) vs. Signal Power plot according to one embodiment.
Figure 29:
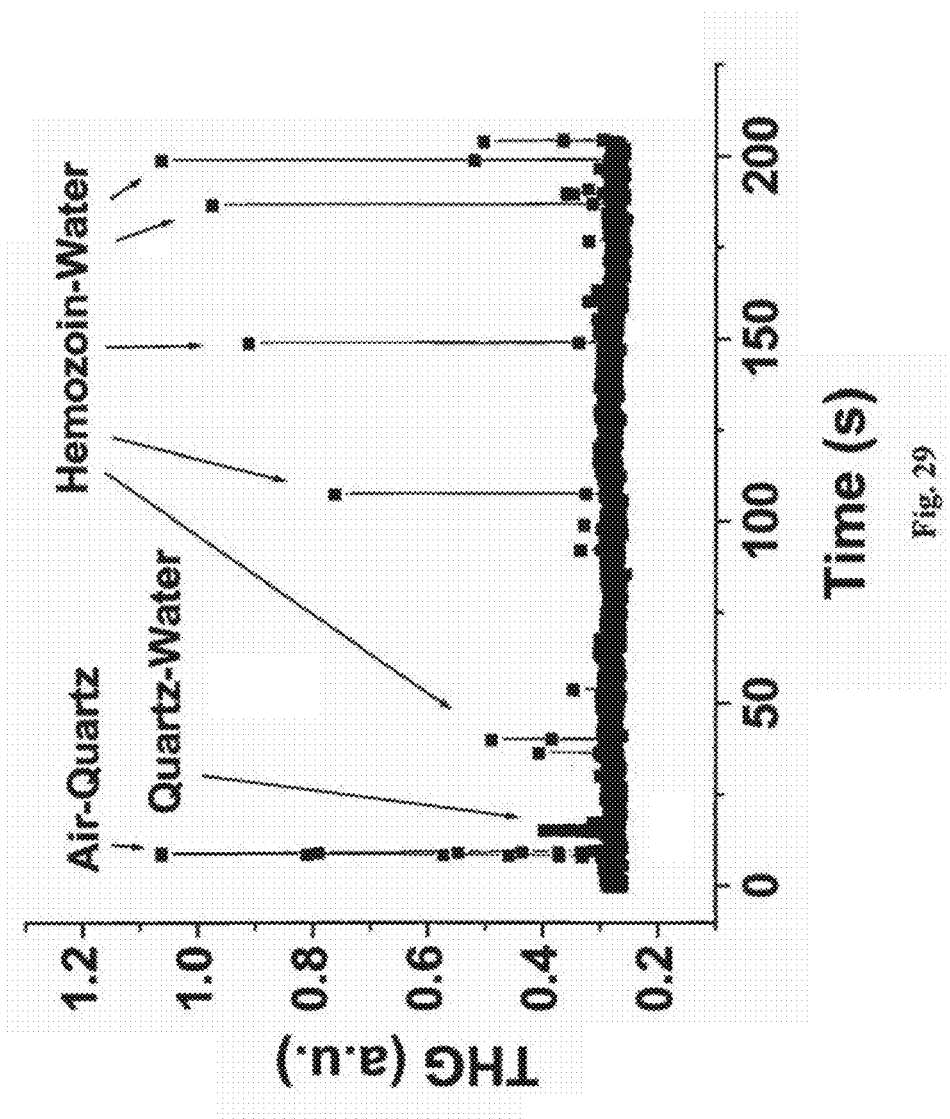
FIG. 29 is a Third Harmonic Generation (THG) vs. Time lot according to one Embodiment.
Figure 30:
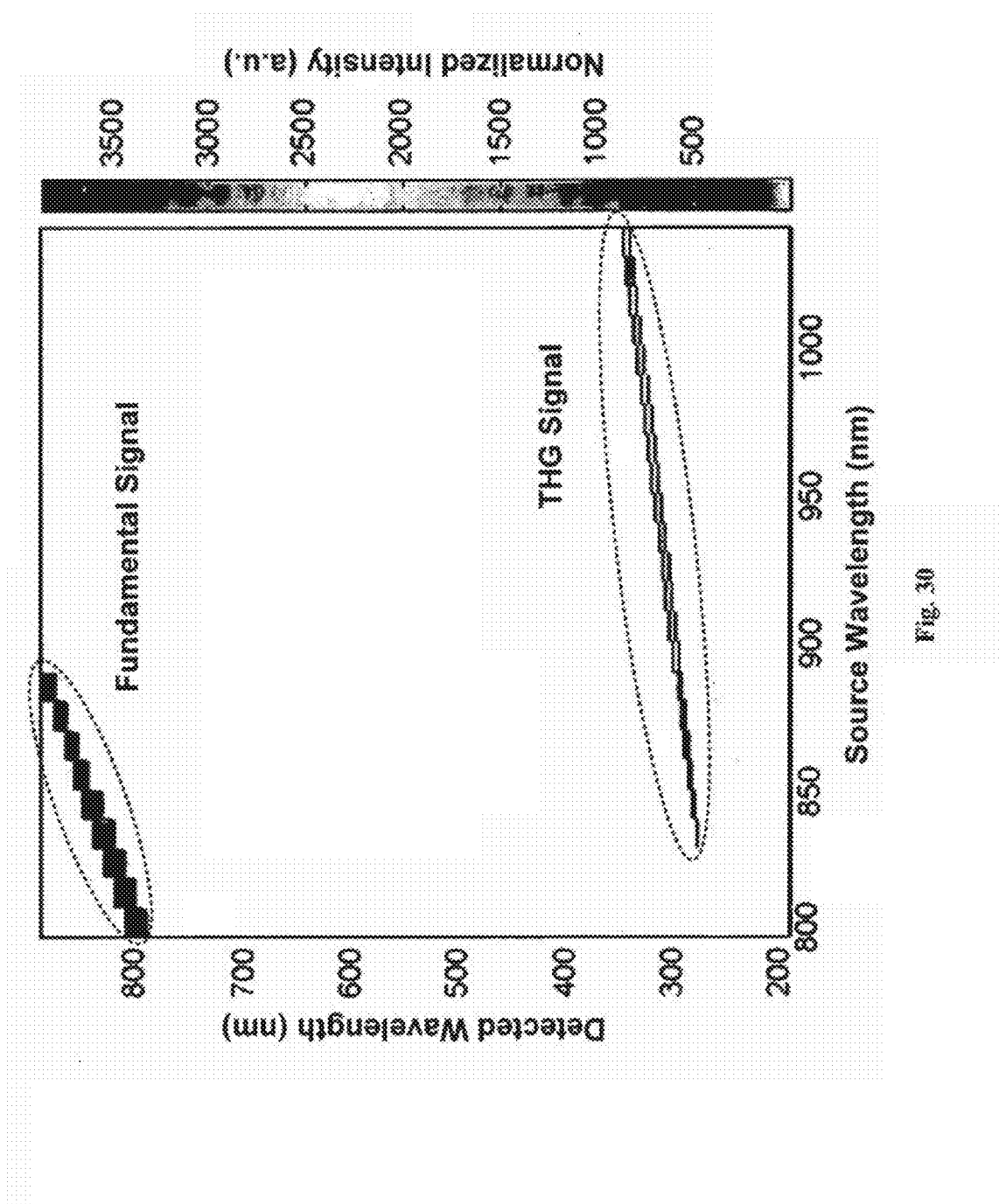
FIG. 30 is Detected Wavelength vs. Source Wavelength plot according to one embodiment.
Figure 32A:
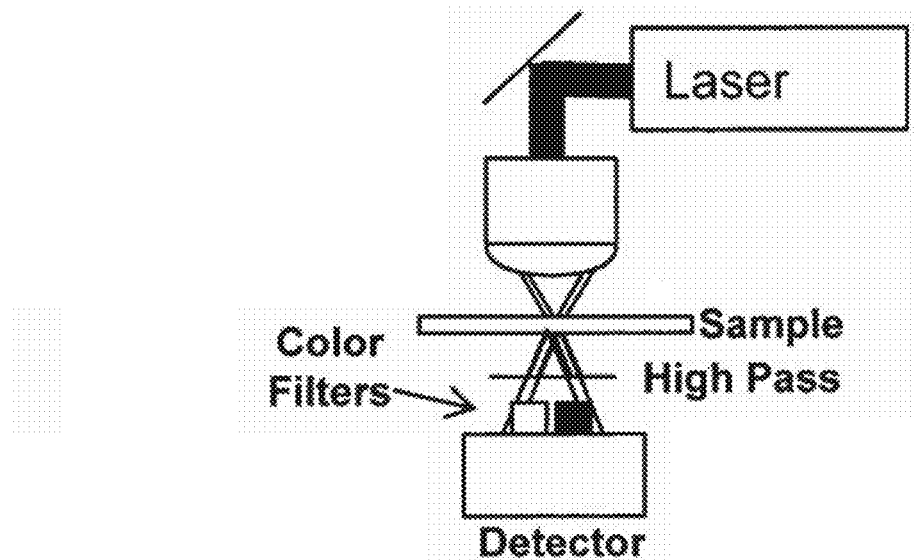
FIG. 32A is a prospective view of a monitor or treatment device using Third Harmonic Generation (THG) detection according to one embodiment.
Figure 32B:
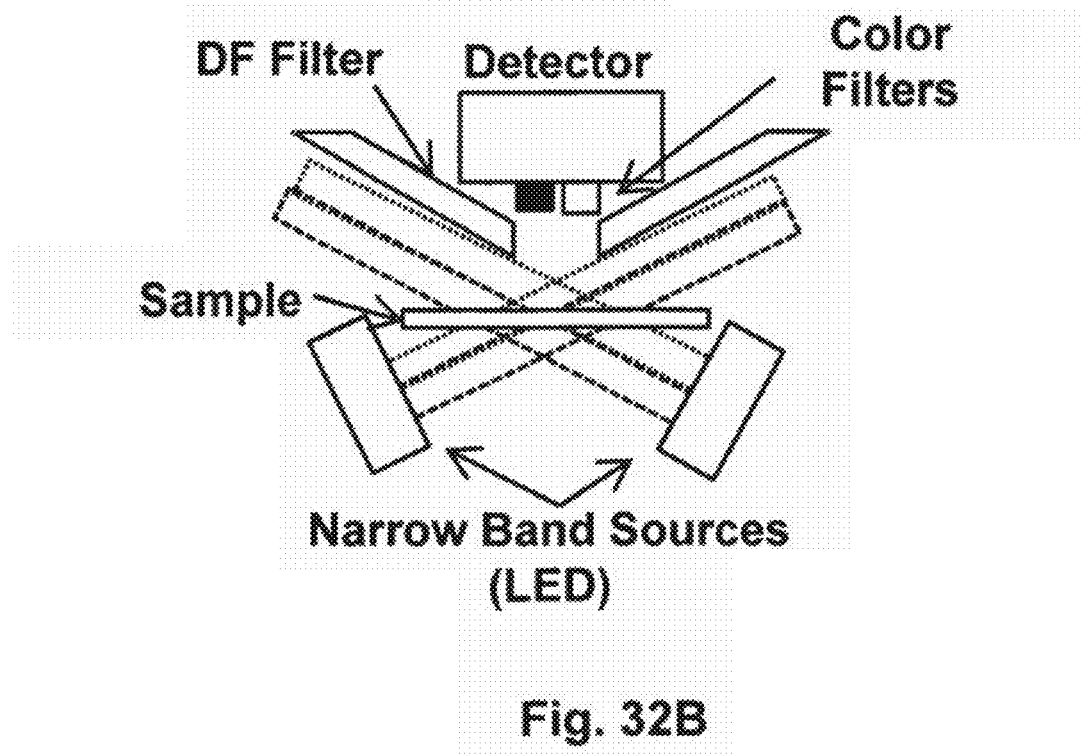
FIG. 32B is a prospective view of a monitor or treatment device using Dark-field detection according to one embodiment.

FIGS. 23A and 23B show $3^{rd}$ order power dependence of hemozoin plotted on (FIG. 23A linear and (FIG. 23A) log-log scale. FIG. 24 shows a $3^{rd}$ order dependence of hemozoin on incident power. FIG. 25 is a voxel image of hemozoin crystals 2502 in infected red blood cells 2504. FIG. 26 shows a two-dimensional spatial scan of infected and uninfected erythrocytes showing intensity peaks that correspond to hemozoin crystals in the infected cells. FIG. 27 shows Third Harmonic Generation (THG) signal from hemozoin nanoparticles suspended in water. FIG. 28 shows the absolute Third Harmonic Generation (THG) power from hemozoin showing $3^{rd}$ order dependence. FIG. 29 Shows Hemozoin-water Third Harmonic Generation (THG) intensity. FIG. 30 shows a two-dimensional plot of Third Harmonic Generation (THG) signal as a function of source and detected wavelength. FIG. 31A show a malaria detection apparatus 102c according to one embodiment. FIG. 31B an example of a monitor or treatment device using an epi-detection setup. FIG. 32A shows an example of a monitor or treatment device using a Third Harmonic Generation (THG) detection setup. FIG. 32B shows an example of a monitor or treatment device using Dark-field detection according to one embodiment.

FIG. 33 shows a malaria detection apparatus 102c, in which one or more methodologies or technologies can be implemented such as, for example, actively detecting or treating a malarial infection. In an embodiment, the malaria detection apparatus 102c includes a dark-field reflected-illumination apparatus 3300, an optical assembly 112, and a sensor component 440.

Referring to FIGS. 33 and 34, in an embodiment, the dark-field reflected-illumination apparatus 3300 includes dark-field illuminator 3302 having, among other things, a body structure 3402 having an aperture 3404 and a plurality of waveguide assemblies 3406. In an embodiment, the dark-field illuminator 3302 is configured to deliver electromagnetic energy through the plurality of waveguide assemblies 3406 onto at least one focal region at one or more angles of incidence relative to an optical axis of an optical assembly 112. For example, in an embodiment, the plurality of waveguide assemblies 3406 are oriented to focus electromagnetic energy onto at least one focal region, at one or more angles of incidence relative to an optical axis of an optical assembly 112. In an embodiment, the dark-field illuminator 3302 is configured to rotate about an axis substantially parallel to the optical axis. In an embodiment, the dark-field illuminator 3302 is configured to deliver a plurality of electromagnetic energy beams onto a focal region at two or more azimuthal angles relative to an optical axis of an optical assembly 112. In an embodiment, the dark-field illuminator 3302 is configured to deliver electromagnetic energy at two or more angles of incidence onto two or more focal region locations.

In an embodiment, the plurality of waveguide assemblies 3406 include one or more electromagnetic energy waveguides 3408 configured to be coupled to at least one electromagnetic energy emitter 3410. For example, in an embodiment, one or more of the plurality of waveguide assemblies 3406 include at least one sleeve member 3412 configured to receive one or more electromagnetic energy waveguides 3408. In an embodiment, one or more of the plurality of waveguide assemblies 3406 include at least one member sleeve 3412 configured configure to receive one or more lenses 3414, polarizers 3416, and electromagnetic energy emitters 3410.

In an embodiment, the plurality of waveguide assemblies 3406 are axially distributed about the aperture 3404. In an embodiment, the plurality of waveguide assemblies 3406 are arranged about the aperture 3404 in one or more radially symmetric patterns. In an embodiment, the plurality of waveguide assemblies 3406 are arrange about the aperture 3404 in one or more rotationally symmetric patterns. In an embodiment, the plurality of waveguide assemblies 3406 are arranged about the aperture 3404 in one or more concentric patterns radially symmetric about an axis substantially parallel to the optical axis. In an embodiment, the plurality of waveguide assemblies 3406 are arranged about the aperture 3404 in one or more concentric patterns rotationally symmetric about an axis substantially parallel to the optical axis. In an embodiment, one or more of the plurality of waveguide assemblies 3406 are configured to collimate electromagnetic energy within the aperture 3404.

In an embodiment, at least one of the plurality of waveguide assemblies 3406 includes at least one polarizer 3416. In an embodiment, at least one of the plurality of waveguide assemblies 3406 includes at least one linear polarizer. In an embodiment, at least one of the plurality of waveguide assemblies 3406 includes at least one circular polarizer. In an embodiment, at least one of the plurality of waveguide assemblies 3406 includes at least one adjustable polarizer.

In an embodiment, at least one of the plurality of waveguide assemblies 3406 includes at least one lens 3414. In an embodiment, at least one of the plurality of waveguide assemblies 3406 includes at least one lens 3414 configured to collimate electromagnetic energy emitted by the at least one electromagnetic energy emitter 3410. In an embodiment, at least one of the plurality of waveguide assemblies 3406 includes at least one lens 3414 configured to focus electromagnetic energy emitted by the at least one electromagnetic energy emitter 3410. In an embodiment, at least one of the plurality of waveguide assemblies 3406 includes at least one microlens array. In an embodiment, at least one of the plurality of waveguide assemblies 3406 includes at least one piano-convex lens. In an embodiment, at least one of the plurality of waveguide assemblies 3406 includes at least one aspheric lens.

In an embodiment, at least one of the plurality of waveguide assemblies 3406 includes at least one multi-focal lens. In an embodiment, at least one of the plurality of waveguide assemblies 3406 includes at least one variable-focus lens. In an embodiment, at least one of the plurality of waveguide assemblies 3406 includes at least one liquid lens. In an embodiment, at least one of the plurality of waveguide assemblies 3406 includes at least one tunable liquid lens. In an embodiment, at least one of the plurality of waveguide assemblies 3406 includes at least one liquid mirror. In an embodiment, at least one of the plurality of waveguide assemblies 3406 includes at least one electrowetting-controlled liquid mirror.

In an embodiment, the electromagnetic energy emitters 3410 include one or more energy-emitting components 104. In an embodiment, the electromagnetic energy emitter 3410 includes at least one of a laser, a laser diode, or a light-emitting diode. In an embodiment, the electromagnetic energy emitter 3410 includes at least one of a quantum dot, an organic light-emitting diode, a microcavity light-emitting diode, or a polymer light-emitting diode. In an embodiment, the electromagnetic energy emitter 3410 includes at least one femtosecond laser.

In an embodiment, the dark-field reflected-illumination apparatus 3300 includes means for removably attaching the dark-field reflected-illumination apparatus 3300 to an optical assembly 112. For example, in an embodiment, the dark-field reflected-illumination apparatus 3300 includes a slip ring 3326, a locking member 3328, and an adapter 3330 for coupling the optical assembly 112 to the dark-field illuminator 3302. In an embodiment, the means for removably attaching the dark-field reflected-illumination apparatus 3300 to an optical assembly 112 includes a coupling structure on the dark-field reflected-illumination apparatus 3300 that couples to a respective coupling structure on optical assembly 112. For example, in an embodiment, the means for removably attaching the dark-field reflected-illumination apparatus 3300 to an optical assembly 112 includes a coupling member having a surface defining an inner passageway, the inner passageway sized and dimensioned to friction fit over an outer surface of an optical assembly 112. In an embodiment, the means for removably attaching the dark-field reflected-illumination 3300 apparatus to an optical assembly 112 includes at least one of a bayonet coupling structure, a friction fit coupling structure, a snap fit coupling structure, or a threaded coupling structure having one or more substructures adapted to coupled to a corresponding bayonet coupling structure, friction fit coupling structure, snap fit coupling structure, or threaded coupling structure on an assembly 112. In an embodiment, the dark-field reflected-illumination apparatus 3300 is configure to removably attach to an optical assembly 112 by a bayonet coupling, a friction fit coupling, a snap fit coupling, or a threaded coupling. In an embodiment, the dark-field reflected-illumination apparatus 3300 includes a coupling structure configure to removably attach the dark-field reflected-illumination apparatus to an optical assembly 112. In an embodiment, the coupling structure is configure to removably attach the dark-field reflected-illumination apparatus to the optical assembly 112 by a bayonet coupling, a friction fit coupling, a snap fit coupling, or a threaded coupling.

Referring to FIG. 33, in an embodiment, the optical assembly 112 includes, among other things, one or more optical assembly body structures 3310 coupled at one end to a detector 440 (e.g., a photodetector, an electromagnetic energy sensors, a charged-coupled device, a camera, or the like), via one or more adapters 3312. In an embodiment, the optical assembly 112 includes at least one piano convex lens 3314 and at least one lens retention member 3316. In an embodiment, the optical assembly 112 includes at least one polarizer 3318 and at least one polarizer retention member 3320. In an embodiment, the optical assembly 112 includes at least retention member 3322 configure to secure a lens assembly within an optical assembly body structure 3310. In an embodiment, the optical assembly 112 includes at least objective assembly 3324.

In an embodiment, the dark-field reflected-illumination apparatus 3300 includes means 3304 for adjusting a dark-field illuminator distance relative to an optical assembly 112 along an axis substantially parallel to an optical axis of the optical assembly 112. In an embodiment, the means 3304 for adjusting the dark-field illuminator distance relative to an optical assembly 112 includes a rotatable-adjustment structure 3332 sized and dimension to couple a threaded member 3334. In an embodiment, the means 3304 for adjusting the dark-field illuminator distance relative to an optical assembly 112 includes a dark-field illuminator securing member 3333 operable to constrain rotation or displacement of the dark-field illuminator 3302.

Figure 35:
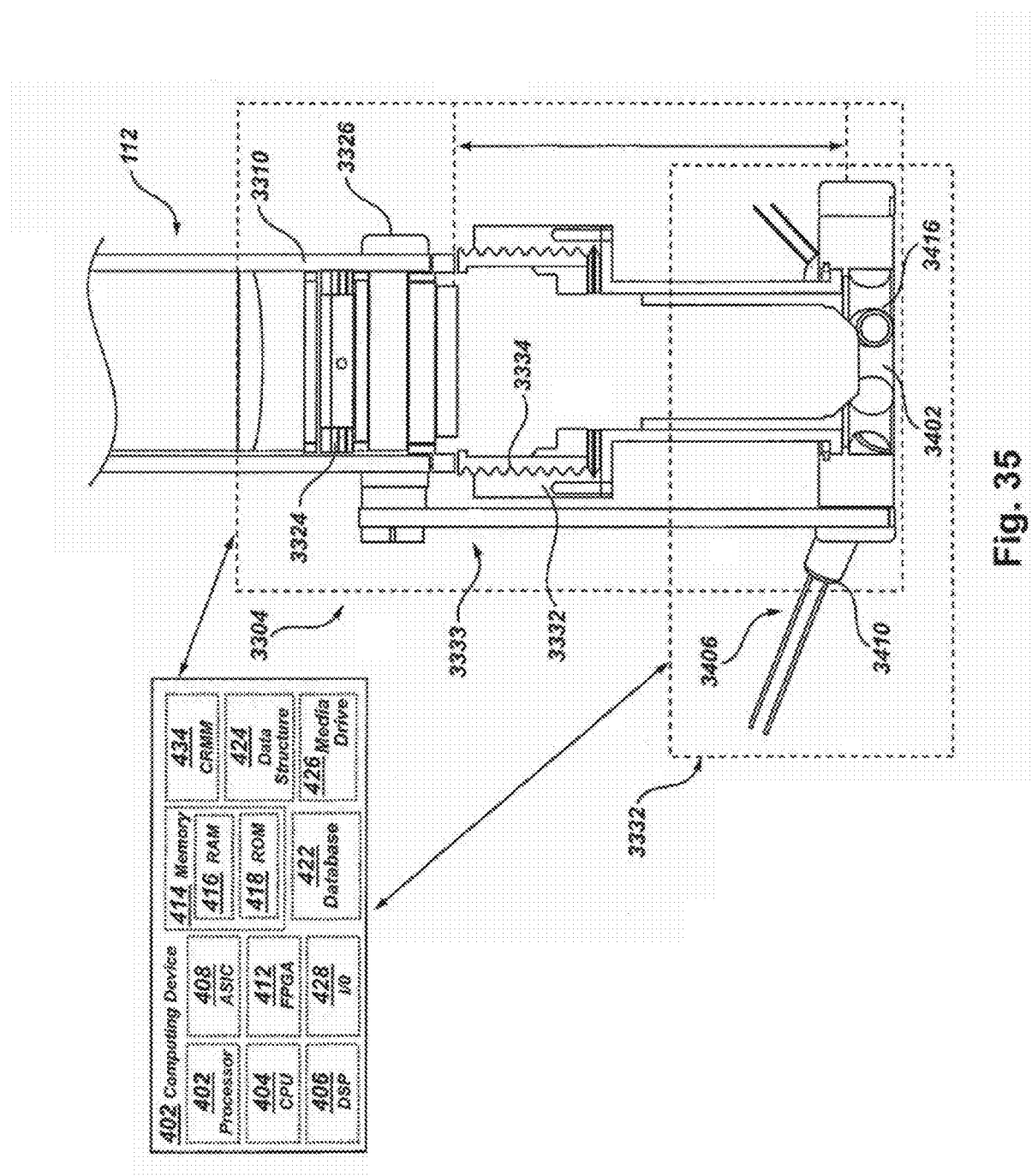
FIG. 35 is cross-sectional view of a monitor or treatment device using Dark field detection according to one embodiment.
Figure 36:
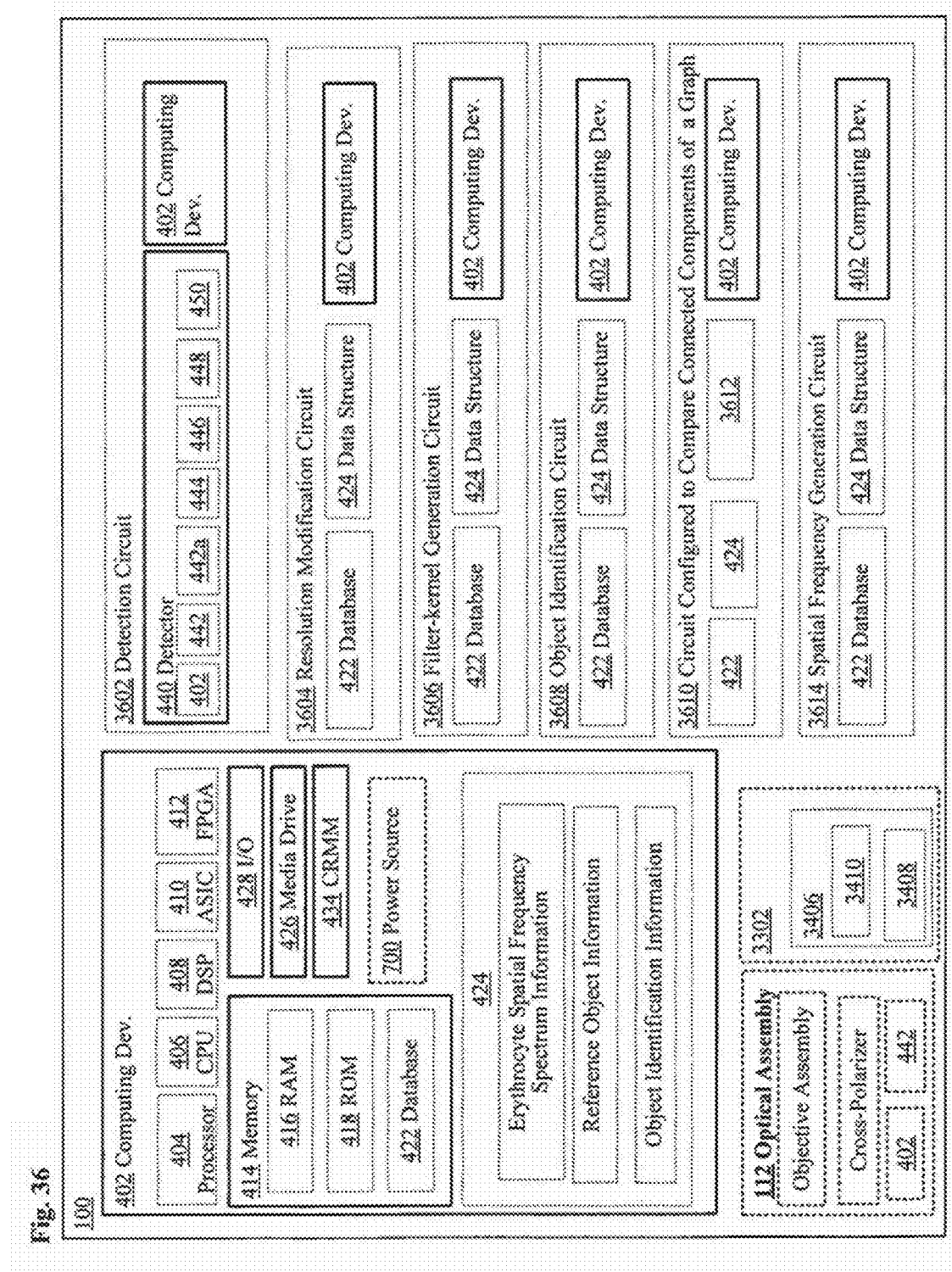
FIG. 36 is a perspective view of a system according to one embodiment.

Referring to FIG. 35, in an embodiment, the means 3304 for adjusting the dark-field illuminator distance relative to an optical assembly 112 includes a computing device 402 operably coupled to at least one of a rotatable-adjustment structure, a threaded adjustment structure, or a slidable-adjustment structure. In an embodiment, the computing device 402 is configured to actuate a displacement via at least one of a one of the rotatable-adjustment structure, the threaded adjustment structure, or the slidable-adjustment structure, of the dark-field illuminator relative to an optical assembly 112, along an axis substantially parallel to an optical axis of the optical assembly 112.

In an embodiment, the means 3304 for adjusting the dark-field illuminator distance relative to an optical assembly 112 includes at least one externally threaded annular structure configure to threadedly engage an internally threaded annular structure that when actuated to rotated relative to the externally threaded annular structure, causes the dark-field illuminator 3302 to displace relative to an optical assembly 112 along an axis substantially parallel to an optical axis of the optical assembly 112.

In an embodiment, the dark-field reflected-illumination apparatus 3300 includes means 3502 for adjusting an angle of incidence of electromagnetic energy emitted by the plurality of electromagnetic energy waveguide assemblies 3406. In an embodiment, the means 3502 for adjusting the angle of incidence of electromagnetic energy emitted by the plurality of electromagnetic energy waveguide assemblies includes at least one computing device 402 operably coupled to at least one of an electro-mechanical component, an opto-mechanical component, an electro-optic component, or an acousto-optic component. In an embodiment, the means 3502 for adjusting the angle of incidence of electromagnetic energy emitted by the plurality of electromagnetic energy waveguide assemblies includes at least one computing device 402 operably coupled to an electro-optic lens system.

In an embodiment, the means 3502 for adjusting the angle of incidence of electromagnetic energy emitted by the plurality of electromagnetic energy waveguide assemblies includes at least one computing device 402 operably coupled to one or more tunable optic components. In an embodiment, the means 3502 for adjusting the angle of incidence of electromagnetic energy emitted by the plurality of electromagnetic energy waveguide assemblies includes a computing device 402 operably coupled to at least one of an optical waveguide configure to change an angle of incidence of electromagnetic energy delivered by one or more of the plurality of waveguide assemblies 3406. In an embodiment, the means 3502 for adjusting the angle of incidence of electromagnetic energy emitted by the plurality of electromagnetic energy waveguide assemblies includes a computing device 402 operably coupled to at least one tunable liquid lens. In an embodiment, the means 3502 for adjusting the angle of incidence of electromagnetic energy emitted by the plurality of electromagnetic energy waveguide assemblies includes a computing device 402 operably coupled to at least one optical micro-prism. In an embodiment, the means 3502 for adjusting the angle of incidence of electromagnetic energy emitted by the plurality of electromagnetic energy waveguide assemblies includes a computing device 402 operably coupled to one or more micro-lens-arrays.

In an embodiment, the dark-field reflected-illumination apparatus 3300 includes means for adjusting an angle of incidence of electromagnetic energy delivered by the dark-field illuminator 3302. In an embodiment, the means 3502 for adjusting the angle of incidence of electromagnetic energy delivered by the dark-field illuminator 3302 includes a computing device 402 operably coupled to at least one of a mechanical-optic component, an electro-optic component, or an acousto-optic component. In an embodiment, the means 3502 for adjusting the angle of incidence of electromagnetic energy delivered by the dark-field illuminator 3302 includes a computing device 402 operably coupled to at least one of an optical waveguide configured to change an angle of incidence of electromagnetic energy delivered by one or more of the plurality of waveguide assemblies 3406. In an embodiment, the means 3502 for adjusting the angle of incidence of electromagnetic energy delivered by the dark-field illuminator 3302 includes a computing device 402 operably coupled to at least one tunable liquid lens. In an embodiment, the means 3502 for adjusting the angle of incidence of electromagnetic energy delivered by the dark-field illuminator 3302 includes a computing device 402 operably coupled to at least one optical micro-prism. In an embodiment, the means 3502 for adjusting the angle of incidence of electromagnetic energy delivered by the dark-field illuminator 3302 includes a computing device 402 operably coupled to one or more micro-lens-arrays.

In an embodiment, a malaria detection apparatus 102c is configured to detect and count of malaria infected erythrocytes. In an embodiment, a malaria detection apparatus 102c employs spectral learning in diagnosing to improve sensitivity and specificity of a diagnosis.

In an embodiment, a malaria detection apparatus 102c includes an optical assembly 112 having a sample side, a detector side, and an optical axis therethrough; a dark-field illuminator 3302 proximate the sample side of the optical assembly 112; and means 3304 for adjusting a dark-field illuminator distance relative to an optical assembly 112 along an axis substantially parallel to an optical axis of the optical assembly 112. In an embodiment, a malaria detection apparatus 102c includes a detector 440 configured to capture one or more micrographs associated with the scattered electromagnetic energy from the sample interrogated by the dark-field illuminator. In an embodiment, a malaria detection apparatus 102c includes a stage assembly configured to secure a sample for analysis. In an embodiment, the dark-field illuminator 3302 includes a plurality of waveguide assemblies 3406, and a body structure 3402 having an aperture 3404 aligned along an axis substantially parallel to an optical axis. In an embodiment, the optical assembly 112 is configured to receive scattered electromagnetic energy from a sample interrogated by the dark-field illuminator 3302. In an embodiment, a malaria detection apparatus 102c includes sample stage assembly configured to receive a biological sample chamber during operation. In an embodiment, the sample stage assembly is configured to position a biological sample along an x, y, or z direction. In an embodiment, the sample stage assembly includes a stepper motor operably coupled to a computing device 402 and is configured to positioning a biological sample chamber based on a tiling protocol.

Referring to FIG. 35, in an embodiment, a system 100 includes, among other things, a detection circuit 3602 configured to acquire one or more micrographs of a biological sample at one or more fields of view. In an embodiment, the detection circuit 3602 includes one or more detectors 440 configured to acquire one or more micrographs of a biological sample at one or more fields of view and at one or more focal depths.

In an embodiment, the system 100 includes a resolution modification circuit 3604 configured to modify a pixel count of at least one micrograph and to generate at least a first modified micrograph. In an embodiment, the resolution modification circuit 3604 includes one or more computing devices 402 configured to modify a micrograph pixel resolution. In an embodiment, the resolution modification circuit 3604 includes at least one computing device 402, and one or more data structures 424 operable to generate and store a threshold comparison value, and to generate and store a kernel for filtering a plurality of pixels forming a micrograph based on the threshold comparison value.

In an embodiment, the system 100 includes a filter-kernel generation circuit 3606 configured to generate a kernel for filtering a plurality of pixels forming the first modified micrograph based on a filtering characteristic, and to generate at least a first significance image representative of the at least one modified micrograph.

In an embodiment, the system 100 includes an object identification circuit 3608 configured to identify groups of pixels in the first significance image indicative of one or more objects imaged in the at least one micrograph, and to generate one or more connected components of a graph representative of groups of pixels indicative of the one or more objects imaged in the at least one micrograph. In an embodiment, the object identification circuit 3608 includes a circuit configured to identify groups of pixels in the first significance image indicative of at least one of a hemozoin nanoparticle, a malaria-infected erythrocyte, or a non-infected erythrocyte in the at least one micrograph. In an embodiment, the object identification circuit 3608 is configure to determine a probability that the biological sample is infected with malaria, and to determine a confidence level associated with the determined probability that the biological sample is infected with malaria.

In an embodiment, the system 100 includes a circuit 3610 configured to compare the generated one or more connected components of the graph to reference object information stored in one or more data structures 424, and to generate a response based on the comparison of the generated one or more connected components of the graph to the reference object information. In an embodiment, the circuit 3610 configured to compare the generated one or more connected components of the graph includes one or more data structures 424 having reference object information stored thereon, the reference object information including at least one of erythrocyte graph information, malaria-infected erythrocyte graph information, or hemozoin graph information. In an embodiment, the circuit 3610 configured to compare the generated one or more connected components of the graph includes a circuit 3612 configured to generate a response including at least one of object identification information, a disease state, a parasitemia level, a erythrocyte count, a ratio of malaria-infected erythrocytes to total erythrocyte present in the at least one micrograph, or probability and confidence level information associated with an identified object.

In an embodiment, the system 100 includes a spatial frequency generation circuit 3614 configured to determine a spatial frequency spectrum of at least a first subset of pixels of the at least one micrograph, compare the spatial frequency spectrum of the first subset of pixels to reference spatial frequency spectrum information, and generate a response based on the comparison of the spatial frequency spectrum of the first subset of pixels to the reference spatial frequency spectrum information. In an embodiment, the spatial frequency generation circuit 3614 includes one or more data structures 424 having at least one of reference erythrocyte spatial frequency spectrum information, reference malaria-infected erythrocyte spatial frequency spectrum information, or reference hemozoin spatial frequency spectrum information. In an embodiment, the spatial frequency generation circuit 3614 is further configured to partition the spatial frequency spectrum of the at least first subset of pixels into one or more information subsets using at least one of a Clustering protocol or a Learning protocol. In an embodiment, the spatial frequency generation circuit 3614 further is configured to partition the spatial frequency spectrum of the at least first subset of pixels into one or information subsets using at least one of a Fuzzy C-Means Clustering protocol, a Graph-Theoretic protocol, a Hierarchical Clustering protocol, a K-Means Clustering protocol, a Locality-Sensitive Hashing protocol, a Mixture of Gaussians protocol, a Model-Based Clustering protocol, a Cluster-Weighted Modeling protocol, an Expectations-Maximization protocol, a Principal Components Analysis protocol, or a Partitioning protocol.

Figure 37A:
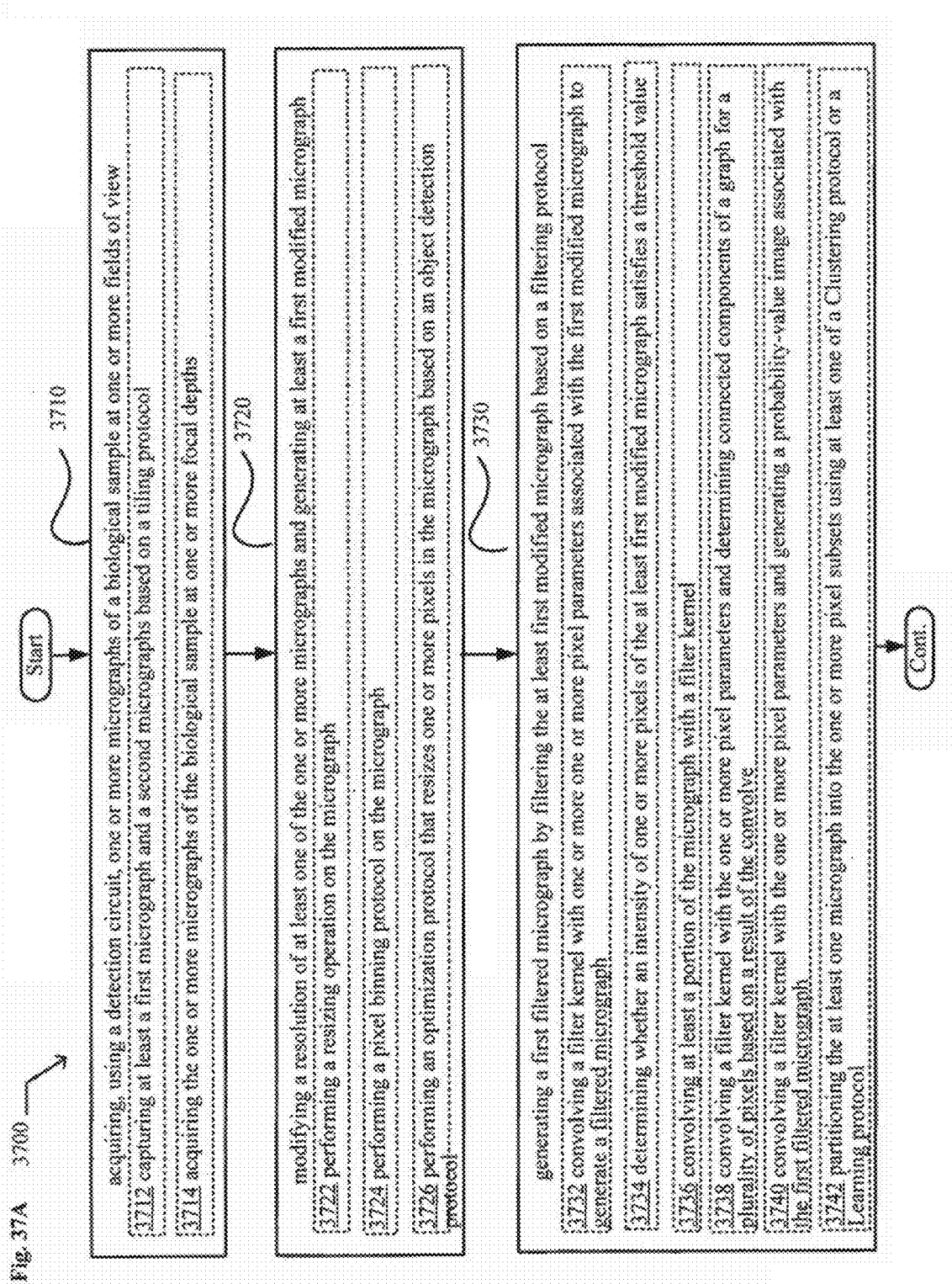

FIG. 37 shows an example of a method 3700. At 3710, the method 3700 includes acquiring, using a detection circuit, one or more micrographs of a biological sample at one or more fields of view. At 3712, acquiring the one or more micrographs of the biological sample includes capturing at least a first micrograph and a second micrographs based on a tiling protocol. At 3714, acquiring the one or more micrographs of the biological sample includes acquiring the one or more micrographs of the biological sample at one or more focal depths.

At 3720, the method 3700 includes modifying a resolution of at least one of the one or more micrographs and generating at least a first modified micrograph. At 3722, modifying the micrograph resolution includes performing a resizing operation on the micrograph. At 3724, modifying the micrograph resolution includes performing a pixel binning protocol on the micrograph. At 3726, modifying the micrograph resolution includes performing an optimization protocol that resizes one or more pixels in the micrograph based on an object detection protocol.

At 3730, the method 3700 includes generating a first filtered micrograph by filtering the at least first modified micrograph based on a filtering protocol. At 3732, generating the first filtered micrograph includes convolving a filter kernel with one or more one or more pixie parameters associated with the first modified micrograph to generate a filtered micrograph. At 3734, generating the first filtered micrograph includes determining whether an intensity of one or more pixels of the at least first modified micrograph satisfies a threshold value. At 3736, generating the first filtered micrograph includes convolving at least a portion of the micrograph with a filter kernel. At 3738, generating the first filtered micrograph includes convolving a filter kernel with the one or more pixel parameters and determining connected components of a graph for a plurality of pixels based on a result of the convolve. At 3740, generating the first filtered micrograph includes convolving a filter kernel with the one or more pixie parameters and generating a probability-value image associated with the first filtered micrograph.

At 3742, generating the first filtered micrograph includes partitioning the at least one micrograph into the one or more pixel subsets using at least one of a Clustering protocol or a Learning protocol. At 3744, generating the first filtered micrograph includes partitioning the at least one micrograph into the one or more pixel subsets using at least one of a Fuzzy C-Means Clustering protocol, a Graph-Theoretic protocol, a Hierarchical Clustering protocol, a K-Means Clustering protocol, a Locality-Sensitive Hashing protocol, a Mixture of Gaussians protocol, a Model-Based Clustering protocol, a Cluster-Weighted Modeling protocol, an Expectations-Maximization protocol, a Principal Components Analysis protocol, or a Partitioning protocol.

At 3750, the method 3700 includes determining a disease state by identifying objects of the biological sample in the filtered micrograph. At 3752, determining the disease state includes comparing the probability-value to threshold criteria to identify objects in the micrograph. At 3754, determining the disease state includes determining connected components of a graph representative of the object content in the first modified micrograph based on the comparing of a probability-value image to threshold criteria. At 3756, determining the disease state includes determining a probability that the biological sample is infected with malaria. At 3758, determining the disease state includes determining a confidence level associated with a determined probability that the biological sample is infected with malaria. At 3760, determining the disease state includes applying a Dulmage-Mendelsohn decomposition protocol to at least a portion of the micrograph to identify connected components.

At 3770, the method 3700 includes acquiring one or more micrographs of a biological sample at one or more focal depths. At 3780, the method 3700 includes causing the storage of the acquired one or more micrographs one or more micrographs of the biological sample on to a physical data structure 424.

EXAMPLE 2

Detecting Malaria in a Biological Sample

Image Acquisition

Figure 38:
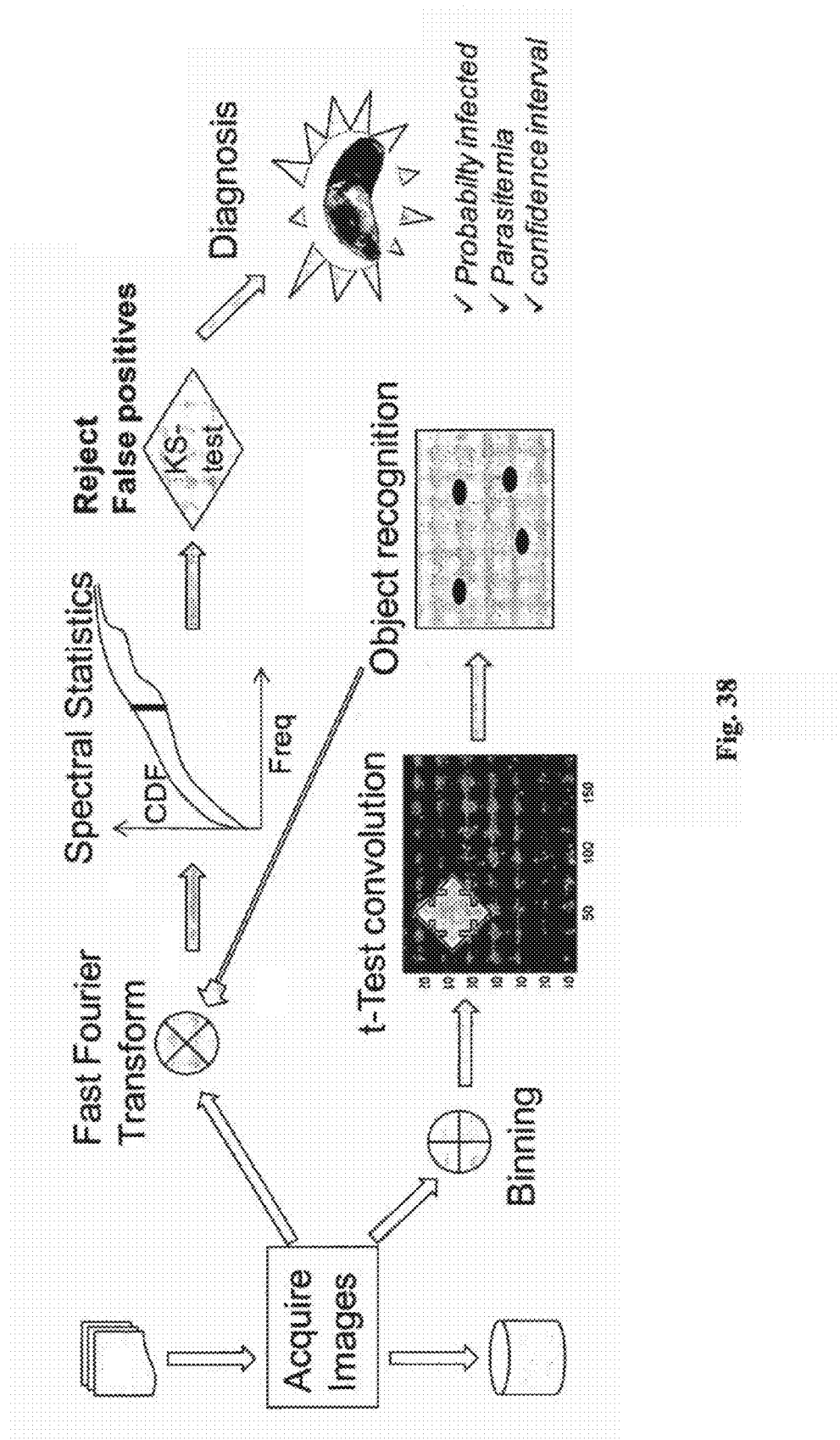
FIG. 38 is a schematic view of a system according to an embodiment.

Referring to FIG. 38, In an embodiment, a malaria detection apparatus 102c takes micrographs from many fields of view on a biological sample (e.g., blood sample). In an embodiment, micrographs are streamed from a sensor component 440 to one or more computing device 402 as they are acquired until a defined pattern of micrograph tiling over the biological sample has been completed by a scanning stage. Each micrograph is stored to a storage device (e.g., a data structure 424) for archiving and processing for disease diagnosis while a sample stage is moves a sample to its next imaging target on a biological sample.

Automated Detection

In an embodiment, automated detection and counting of infected cells is accomplished by a combination of statistical methods that quantify the probability that an individual is infected and the confidence interval on parasitemia (fraction of blood cells with a parasite).

Finding Significant Objects

In an embodiment, a micrograph is first adjusted in resolution by binning pixels or applying another resize operation to optimize the size of each pixel in the micrograph for object detection. In an embodiment, objects infected with malaria are detected by measuring how bright they are: infected cells appearing brighter than non-infected cells. In one embodiment, a t-test filter is applied to the resized micrograph to measure the probability that a pixel is not any brighter than the background (the null hypothesis). A threshold is specified for the null hypothesis, (e.g., 0.01) such that any pixel with a p-value less than the null hypothesis threshold is counted as being an object significantly brighter than the background pixels. In an embodiment, background pixels are defined by a filter kernel as a region of some size surrounding the pixel under test. This kernel is convolved over the entire micrograph, and the filter may be embodied as a nonlinear filter, a linear filter on nonlinear image intermediates, or a linear filter of the micrograph. In an embodiment, a t-test is implemented as a linear filter on nonlinear image intermediates to increase the speed of the computation.

In an embodiment, pixels may be compared to the entire micrograph as the background distribution. However, there is a distinct advantage to filtering with a kernel some fraction of the micrograph size: lateral brightness adaptation is inherent to small kernels. The significance test with such a kernel is insensitive to variations in illumination intensity across the field of view and also ignores many objects larger than the desired target.

Object Identification

In an embodiment, multiple pixels may be significant for one erythrocyte in the micrograph and they need to be identified as a single object. In embodiment, objects (e.g., malaria-infected cells, etc.) are identified by determining the connected components of the graph of significant pixels. For example, a Dulmage-Mendelsohn decomposition of the adjacency matrix is determined to identify distinct groups of significant pixels. In an embodiment, each connected component found is likely to be a malaria-infected cell (with a p-value returned by the t-test).

Spectral Screen for Specificity

To improve the specificity of diagnosis, in an embodiment, false positives are minimized by performing a spectral (e.g., spatial frequency) analysis of the micrographs.

For example, in an embodiment, for each significant object, multiple windows of different sized pixel regions are selected from the original (unresized) micrograph and fast Fourier transform is determined to generate the spectral signature of each object. In an embodiment, the object spectrum is compared to templates a stored library of spectra from previously-analyzed objects. In an embodiment, the library includes many samples of known infected cells, autodetected infected cells, and a multitude of controls such as dust, scratches, fingerprints, healthy blood, out of focus, defective illumination, etc. The spectrum of each object is compared to one or more of the reference spectra from the library using statistical tests to calculate the probability that the spectral signatures are the same. In an embodiment, thresholds of the null hypothesis (two spectra have the same distribution) are applied to screen objects and select those that are consistent with the characteristics of an infected cell. In one embodiment of the spectral screen, the 2D FFT is integrated in various coordinate systems to obtain the power spectra of the object in the x-, y-, radial-, and angular-directions. These power spectra are in fact probability density functions for the distribution of energy across spatial frequency in the micrograph. The Komolgorov-Smirnov test is applied to calculate the null hypothesis for each power spectrum compared to reference spectra in the library. In another embodiment, template matching is performed by cross-correlation of the 2D object spectrum with 2D reference spectra in the library. Again, significance tests are applied to measure the probability that the object spectrum matches a spectrum from the library.

Diagnosis

In an embodiment, following object identification and spectral screens, only objects satisfying a threshold probability of being infected cells are counted, along with the associated p-value for each object. In an embodiment, a diagnosis infected/not infected is generated along with the calculated probability that the individual is in fact infected. In an embodiment, a generate response includes reporting the number of infected cells, as a ratio of infected cells to total cells along with the 95% confidence interval on that ratio.

Spectral Learning in the Template Library

In an embodiment, an object recognition circuit includes a library of objects with known identity under controlled conditions. In an embodiment, micrographs of infected cells are processed and the spectra saved to the library to confirm the identity of significant objects. In an embodiment, micrographs of non-infected samples are processed and saved to the library for the purpose of rejecting false positives before they are counted in the diagnosis report. In an embodiment, spectral information from processed micrographs are stored in a data structure library with its associated p-value. The variance and mean of library spectra are calculated with weights according to the probability that an object spectrum belongs in the library category to which it was assigned (e.g., dust particle, etc.) by the template matching process.

Multidimensional Object Identification

In an embodiment, by using a stage that scans in 3 dimensions, with the addition of z-axis for focus, more spatial information may be obtained about an object. For example, a very flat object can be distinguished from a more spherical object of the same radius by moving the plan of focus and taking another micrograph. An additional embodiment of object recognition is to take 2 or more micrographs at different focal planes in the sample from the same field of view. In an embodiment, deconvolution of the micrograph stack is performed with or without knowledge of the point spread function to reconstruct the 3-dimensional shape of the object. Again, template matching to a library is applied, but now in more dimensions. In an embodiment, approaches associated with monochromatic micrographs can be applied to color micrographs by addition of a dimension for optical wavelength. Spectral analysis can then be performed in the spatial dimensions and the optical wavelength dimension in combination.

In an embodiment, one or more components may be referred to herein as "configured to," "configurable to," "operable/operative to," "adapted/adaptable," "able to," "conformable/conformed to," etc. Such terms (e.g., "configured to") can generally encompass active-state components and/or inactive-state components and/or standby-state components, unless context requires otherwise.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by the reader that each function and/or operation within such block diagrams, flowcharts, or examples can be implemented, individually and/or collectively, by a wide range of hardware, software, firmware, or virtually any combination thereof. Further, the use of "Start," "End" or "Stop" blocks in the block diagrams is not intended to indicate a limitation on the beginning or end of any functions in the diagram. Such flowcharts or diagrams may be incorporated into other flowcharts or diagrams where additional functions are performed before or after the functions shown in the diagrams of this application. In an embodiment, several portions of the subject matter described herein may be implemented via Application Specific Integrated Circuits (ASICs), Field Programmable Gate Arrays (FPGAs), digital signal processors (DSPs), or other integrated formats. However, some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors 404 (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, the mechanisms of the subject matter described herein are capable of being distributed as a program product in a variety of forms, and that an illustrative embodiment of the subject matter described herein applies regardless of the particular type of signal-bearing medium used to actually carry out the distribution. Non-limiting examples of a signal-bearing medium include the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link (e.g., transmitter, receiver, transceiver, transmission logic, reception logic, etc.), etc.).

While particular aspects of the present subject matter described herein have been shown and described, it will be apparent to the reader that, based upon the teachings herein, changes and modifications may be made without departing from the subject matter described herein and its broader aspects and, therefore, the appended claims are to encompass within their scope all such changes and modifications as are within the true spirit and scope of the subject matter described herein. In general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). Further, if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense of the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense of the convention (e.g., "a system having at least one of A, B, or C" would include but not be limited to systems that have A alone, B alone, C alone, A and B together, A and C together, B and C together, and/or A, B, and C together, etc.). Typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, the operations recited therein generally may be performed in any order. Also, although various operational flows are presented in a sequence(s), it should be understood that the various operations may be performed in orders other than those that are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

While various aspects and embodiments have been disclosed herein, other aspects and embodiments are contemplated. The various aspects and embodiments disclosed herein are for purposes of illustration and are not intended to be limiting, with the true scope and spirit being indicated by the following claims.

What is claimed is:

1. A system, comprising:
  a resolution modification circuit configured to modify a pixel count of at least one micrograph of a biological sample acquired at one or more fields of view and to generate at least a first modified micrograph;
  a filter-kernel generation circuit configured to generate a kernel for filtering a plurality of pixels forming the first modified micrograph based on a filtering characteristic, and to generate at least a first significance image representative of the at least one modified micrograph; and
  an object identification circuit configured to identify groups of pixels in the first significance image indicative of one or more objects imaged in the at least one micrograph, and to generate one or more connected components of a graph representative of groups of pixels indicative of the one or more objects imaged in the at least one micrograph,
  wherein the object identification circuit is configured to determine a probability that the biological sample is infected with malaria, and to determine a confidence level associated with the determined probability that the biological sample is infected with malaria.

2. The system of claim 1, further comprising:
  a circuit configured to compare the generated one or more connected components of the graph to reference object information stored in one or more data structures, and to generate a response based on the comparison of the generated one or more connected components of the graph to the reference object information.

3. The system of claim 2, wherein the circuit configured to compare the generated one or more connected components of the graph includes one or more data structures having reference object information stored thereon, the reference object information including at least one of erythrocyte graph information, malaria-infected erythrocyte graph information, or hemozoin graph information.

4. The system of claim 2, wherein the circuit configured to compare the generated one or more connected components of the graph includes a circuit configured to generate a response including at least one of object identification information, a disease state, a parasitemia level, an erythrocyte count, a ratio of malaria-infected erythrocytes to total erythrocyte present in the at least one micrograph, or probability and confidence level information associated with an identified object.

5. The system of claim 1, wherein the object identification circuit includes a circuit configured to identify groups of pixels in the first significance image indicative of at least one of a hemozoin nanoparticle, a malaria-infected erythrocyte, or a non-infected erythrocyte in the at least one micrograph.

6. The system according to claim 1, wherein the resolution modification circuit includes one or more computing devices configured to modify a micrograph pixel resolution.

7. The system according to claim 1, wherein the resolution modification circuit includes at least one computing device, and one or more data structures operable to generate and store a threshold comparison value, and to generate and store a kernel for filtering a plurality of pixels forming a micrograph based on the threshold comparison value.

8. A system comprising:
a resolution modification circuit configured to modify a pixel count of at least one micrograph of a biological sample acquired at one or more fields of view and to generate at least a first modified micrograph;
a filter-kernel generation circuit configured to generate a kernel for filtering a plurality of pixels forming the first modified micrograph based on a filtering characteristic, and to generate at least a first significance image representative of the at least one modified micrograph;
an object identification circuit configured to identify groups of pixels in the first significance image indicative of one or more objects imaged in the at least one micrograph, and to generate one or more connected components of a graph representative of groups of pixels indicative of the one or more objects imaged in the at least one micrograph; and
a spatial frequency generation circuit configured to
determine a spatial frequency spectrum of at least a first subset of pixels of the at least one micrograph,
compare the spatial frequency spectrum of the first subset of pixels to reference spatial frequency spectrum information, and
generate a response based on the comparison of the spatial frequency spectrum of the first subset of pixels to the reference spatial frequency spectrum information.

9. The system of claim 8, wherein the spatial frequency generation circuit includes one or more data structures having at least one of reference erythrocyte spatial frequency spectrum information, reference malaria-infected erythrocyte spatial frequency spectrum information, or reference hemozoin spatial frequency spectrum information.

10. The system of claim 8, wherein the spatial frequency generation circuit is further configured to partition the spatial frequency spectrum of the at least first subset of pixels into one or more information subsets using at least one of a Clustering protocol or a Learning protocol.

11. The system of claim 8, wherein the spatial frequency generation circuit is further configured to partition the spatial frequency spectrum of the at least first subset of pixels into one or more information subsets using at least one of a Fuzzy C-Means Clustering protocol, a Graph-Theoretic protocol, a Hierarchical Clustering protocol, a K-Means Clustering protocol, a Locality-Sensitive Hashing protocol, a Mixture of Gaussians protocol, a Model-Based Clustering protocol, a Cluster-Weighted Modeling protocol, an Expectations-Maximization protocol, a Principal Components Analysis protocol, or a Partitioning protocol.

12. A method, comprising:
modifying a resolution of one or more micrographs of a biological sample acquired at one or more fields of view and generating at least a first modified micrograph;
generating a first filtered micrograph by filtering the at least first modified micrograph based on a filtering protocol; and
determining a disease state by identifying objects of the biological sample in the filtered micrograph, wherein determining the disease state includes determining a probability that the biological sample is infected with malaria.

13. The method of claim 12, wherein modifying the micrograph resolution includes performing a resizing operation on the micrograph.

14. The method of claim 12, wherein modifying the micrograph resolution includes performing a pixel binning protocol on the micrograph.

15. The method of claim 12, wherein modifying the micrograph resolution includes performing an optimization protocol that resizes one or more pixels in the micrograph based on an object detection protocol.

16. The method of claim 12, wherein generating the first filtered micrograph includes convolving a filter kernel with one or more pixel parameters associated with the first modified micrograph to generate a filtered micrograph.

17. The method of claim 12, wherein generating the first filtered micrograph includes determining whether an intensity of one or more pixels of the at least first modified micrograph satisfies a threshold value.

18. The method of claim 12, wherein generating the first filtered micrograph includes convolving at least a portion of the micrograph with a filter kernel.

19. The method of claim 12, wherein generating the first filtered micrograph includes convolving a filter kernel with the one or more pixel parameters and determining connected components of a graph for a plurality of pixels based on a result of the convolve.

20. The method of claim 12, wherein generating the first filtered micrograph includes convolving a filter kernel with the one or more pixel parameters and generating a probability-value image associated with the first filtered micrograph.

21. The method of claim 20, wherein determining the disease state includes comparing the probability-value to threshold criteria to identify objects in the micrograph.

22. The method of claim 20, wherein determining the disease state includes determining connected components of a graph representative of the object content in the first modified micrograph based on the comparing of a probability-value image to threshold criteria.

23. The method of claim 12, wherein determining the disease state further includes determining a confidence level associated with a determined probability that the biological sample is infected with malaria.

24. The method of claim 12, wherein determining the disease state further includes applying a Dulmage-Mendelsohn decomposition protocol to at least a portion of the micrograph to identify connected components.

25. The method of claim 12, wherein generating the first filtered micrograph includes partitioning the at least one micrograph into the one or more pixel subsets using at least one of a Clustering protocol or a Learning protocol.

26. The method of claim 12, wherein generating the first filtered micrograph includes partitioning the at least one micrograph into the one or more pixel subsets using at least one of a Fuzzy C-Means Clustering protocol, a Graph-Theoretic protocol, a Hierarchical Clustering protocol, a K-Means Clustering protocol, a Locality-Sensitive Hashing protocol, a Mixture of Gaussians protocol, a Model-Based Clustering protocol, a Cluster-Weighted Modeling protocol, an Expectations-Maximization protocol, a Principal Components Analysis protocol, or a Partitioning protocol.

27. The method of claim 12, further comprising:
acquiring one or more micrographs of a biological sample at one or more focal depths.

28. The method of claim 12, further comprising:
causing the storage of the acquired one or more micrographs of the biological sample on to a physical data structure.

* * * * *